United States Patent
Judd et al.

(10) Patent No.: US 10,923,662 B2
(45) Date of Patent: *Feb. 16, 2021

(54) FLUOROALKYLFLUORENE DERIVATIVES

(71) Applicant: LOMOX LIMITED, Congleton (GB)

(72) Inventors: Luke William Judd, Congleton (GB); Matthew Phillip Aldred, Congleton (GB); Gene Carl Koch, Congleton (GB)

(73) Assignee: Lomox Limited, Congleton (GB)

( * ) Notice: Subject to any disclaimer, the term of this patent is extended or adjusted under 35 U.S.C. 154(b) by 319 days.

This patent is subject to a terminal disclaimer.

(21) Appl. No.: 15/975,224

(22) Filed: May 9, 2018

(65) Prior Publication Data

US 2018/0261771 A1 Sep. 13, 2018

Related U.S. Application Data

(63) Continuation of application No. 15/301,598, filed as application No. PCT/GB2015/051164 on Apr. 17, 2015, now Pat. No. 10,084,137.

(30) Foreign Application Priority Data

Apr. 17, 2014 (GB) .................................. 1406977.7

(51) Int. Cl.
    *H01L 51/50* (2006.01)
    *H01L 51/00* (2006.01)
    (Continued)

(52) U.S. Cl.
    CPC ........ *H01L 51/0039* (2013.01); *C07C 43/225* (2013.01); *C07C 65/21* (2013.01);
    (Continued)

(58) Field of Classification Search
None
See application file for complete search history.

(56) References Cited

U.S. PATENT DOCUMENTS 9,761,804 B2    9/2017   Koch
2002/0106531 A1   8/2002   Naito
(Continued)

FOREIGN PATENT DOCUMENTS

GB       2424881 A     10/2006
WO    2015159098 A1   10/2015

OTHER PUBLICATIONS

Aldred et al., "Synthesis and mesomorphic behaviour of novel light-emitting liquid crystals," Liquid Crystals, 2005, vol. 32, Issue 10, pp. 1251-1264.
(Continued)

*Primary Examiner* — Gregory D Clark
(74) *Attorney, Agent, or Firm* — Stinson LLP

(57) ABSTRACT

Compounds of the formula $D-S^1-A-S^2-B^1$ wherein A comprises a 2,7-disubstituted 9,9-fluoroalkyl fluorene diradical of the formula

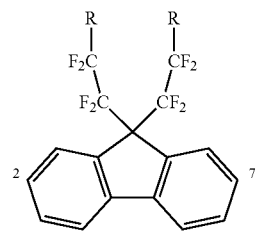

wherein $S^1$, $S^2$, D and $B^1$ have meanings given in the description that are useful as charge transport and
(Continued)

emissive materials for the fabrication of electronic devices such as diodes, transistors, and photovoltaic devices.

20 Claims, 5 Drawing Sheets

(51) Int. Cl.
| | |
|---|---|
| C07C 43/225 | (2006.01) |
| C07D 417/14 | (2006.01) |
| C07D 207/452 | (2006.01) |
| C07D 285/14 | (2006.01) |
| C07C 69/60 | (2006.01) |
| C07C 65/21 | (2006.01) |
| C07C 69/593 | (2006.01) |
| C07C 69/92 | (2006.01) |
| C07D 207/46 | (2006.01) |
| C08G 61/12 | (2006.01) |
| C09K 11/02 | (2006.01) |
| C09K 19/32 | (2006.01) |
| H01L 51/42 | (2006.01) |
| H01L 51/05 | (2006.01) |

(52) U.S. Cl.
CPC ............ *C07C 69/593* (2013.01); *C07C 69/60* (2013.01); *C07C 69/92* (2013.01); *C07D 207/452* (2013.01); *C07D 207/46* (2013.01); *C07D 285/14* (2013.01); *C07D 417/14* (2013.01); *C08G 61/121* (2013.01); *C09K 11/025* (2013.01); *C09K 19/32* (2013.01); *H01L 51/005* (2013.01); *H01L 51/0035* (2013.01); *H01L 51/0036* (2013.01); *H01L 51/0052* (2013.01); *H01L 51/0068* (2013.01); *H01L 51/0071* (2013.01); *H01L 51/0076* (2013.01); *C07C 2603/18* (2017.05); *C08G 2261/146* (2013.01); *C08G 2261/228* (2013.01); *C08G 2261/312* (2013.01); *C08G 2261/3142* (2013.01); *C08G 2261/3221* (2013.01); *C08G 2261/3223* (2013.01); *C08G 2261/3246* (2013.01); *C08G 2261/512* (2013.01); *C08G 2261/53* (2013.01); *C08G 2261/76* (2013.01); *C08G 2261/91* (2013.01); *C08G 2261/92* (2013.01); *C08G 2261/95* (2013.01); *H01L 51/0512* (2013.01); *H01L 51/42* (2013.01); *H01L 51/5012* (2013.01); *H01L 51/5056* (2013.01); *Y02E 10/549* (2013.01)

(56) References Cited

U.S. PATENT DOCUMENTS

| | | | |
|---|---|---|---|
| 2005/0031801 A1 | 2/2005 | Shundo et al. | |
| 2005/0089716 A1 | 4/2005 | Nakaya et al. | |
| 2005/0189873 A1* | 9/2005 | Kelly | C07D 333/18 313/504 |
| 2006/0163562 A1 | 7/2006 | Boerner | |
| 2010/0143612 A1 | 6/2010 | Hirai | |

OTHER PUBLICATIONS

International Search Report, PCT/GB2015/051164, dated Aug. 5, 2015, 4 pages.
Written Opinion, PCT/GB2015/051164, dated Aug. 5, 2015, 7 pages.
Great Britain Search Report, GB Application No. 1406977.7, dated Dec. 5, 2014, 2 pages.
Aldred et al., "Light-Emitting Fluorene Photoreactive Liquid Crystals for Organic Electroluminescence," Chem. Mater. 2004, 16, pp. 4928-4936.
Contoret et al, "The Photopolymerization and Cross-Linking of Electroluminescent Liquid Crystals Containing Methacrylate and Diene Photopolymerizable End Groups for Multilayer Organic Light-Emitting Diodes," Chem. Mater. 2002, 14, pp. 1477-1487.

* cited by examiner

A

B

FLUOROALKYLFLUORENE DERIVATIVES

REFERENCED TO RELATED APPLICATIONS

This application is a continuation of U.S. national stage application Ser. No. 15/301,598 filed Oct. 3, 2016, which is a national stage application based on International Patent Application No. PCT/GB2015/051164, filed Apr. 17, 2015, and claims the benefit of priority of that national stage application, the PCT application, and Great Britain Application No. 1406977.7, filed Apr. 17, 2014, the entire disclosures of which are incorporated herein by reference.

FIELD OF THE INVENTION

The present invention relates to novel compounds with electronic and photoelectronic properties that render them useful for the production of electrical devices. The invention further relates to electronic devices that incorporate layers comprising these compounds wherein these compounds function as charge transport materials or photoluminescent materials.

BACKGROUND OF THE INVENTION

Organic light emitting diodes (OLED) are light emitting diodes in which the emissive electroluminescent material is a film of organic material which emits light in response to an electrical current. The emissive organic layer of an OLED is sandwiched between two electrical contact layers. For enhanced efficiency, in addition to a light emitting layer, the OLED device may incorporate layers of charge transporting material between the emissive layer and the electrical contact layer. These charge transporting layers may comprise either hole or electron transporting materials. These charge transport materials can allow the charge-carrying holes and electrons to migrate through to the emissive layer, thereby facilitating their combination to form a bound state called an exciton. The electrons in the excitons in due course relax into a lower energy state by emitting radiation which, for an OLED device, is of a frequency most often in the visible region.

There is considerable ongoing interest in the development of new materials with improved properties that are suitable for use in the fabrication of OLED devices. Materials that, for example, function as emitters, electron transporters and hole transporters are of particular interest. Many materials have been developed over the years in the attempt to produce improved OLED devices and in particular devices with optimal light output, energy efficiency and life time. In addition, a further notable goal is the realisation of materials that allow the device fabrication process to be simplified. Notwithstanding existing materials, there is a continuing need for materials that have properties such as those identified above that possess superior combination of properties for the fabrication of OLED devices and other electronic devices.

It is known that some reactive mesogens (liquid crystalline materials capable of being chemically crosslinked into a polymer matrix) of the general formula:

where A represents a linear aromatic molecular core comprising a fluorene substituted with two alkyl groups at C-9, S represents flexible spacer units and B represents crosslinking groups such as methacrylate groups, may be useful in the fabrication of organic electronic devices. This is particularly the case if B represents a photo-crosslinkable group, since then the materials function essentially as photoresists, which is to say, thin layers of these materials may be patterned into useful electronic structures by patterned exposure to light, particularly UV light.

Further, if the linear aromatic core A is luminescent in nature, these reactive mesogen materials may be patterned into the active light emitting layers in electroluminescent devices such as organic light emitting diodes (OLEDS) and organic diode lasers. However, working OLED devices of the B—S-A-S—B structure have exhibited disappointingly low lifetimes.

It is an object of the present invention to provide new fluorene containing materials for use in electronic devices which overcome, or substantially reduce, problems associated with existing fluorene derivatives.

SUMMARY OF THE INVENTION

In a first aspect of the present invention, there is provided a compound of Formula (I)

wherein:

A represents —$Ar^1$—(FL-$Ar^2$)$_n$— and comprises from 1 to 8 FL groups;

$Ar^1$ and $Ar^2$ in each occurrence are independently selected from the group comprising $Ar^a$ and a bond;

$Ar^a$ represents a diradical comprising 1 aromatic, heteroaromatic or FL moiety, or 2, 3, 4 or 5 aromatic, heteroaromatic and/or FL moieties mutually connected by a single bond;

n is an integer from 1 to 8;

FL is a fluorene moiety of the structure

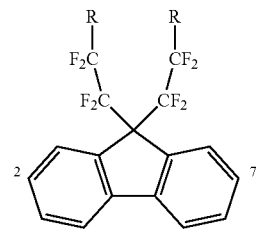

incorporated into the chain through covalent bonds at C-2 and C-7;

the R groups of each FL moiety are identical and are selected from the group consisting of straight chain or branched achiral $C_1$-$C_{14}$ alkyl, $C_1$-$C_{14}$ haloalkyl, $C_1$-$C_{14}$ fluoroalkyl, $C_2$-$C_{14}$ alkenyl group, optionally wherein 1, 2, 3, 4 or 5 $CH_2$ groups are replaced by an oxygen provided that no acetal, ketal, peroxide or vinyl ether is present in the R group;

D represents a cross linkable group or, when $B^1$ represents a hydrogen, D represents —$B^2$—$S^3$—$B^3$—$S^{1a}$-A-$S^{2a}$—$B^{1a}$, —$S^3(B^2)$—$B^3$—$S^{1a}$-A-$S^{2a}$—$B^{1a}$, —$S^3(B^2)(B^3)$—$S^{1a}$-A-$S^{2a}$—$B^{1a}$, —$S^3(B^2)(B^3)$, or a cross linkable group wherein the dash at the left-hand end of the chain represents the point of attachment to $S^1$;

$B^1$ represents a cross linkable group or a hydrogen atom;

$B^{1a}$ represents a cross linkable group or a hydrogen atom;

$B^2$ and $B^3$ each represents a cross linkable group;

$S^1$, $S^2$, $S^{1a}$ and $S^{2a}$ are flexible linker groups; and $S^3$ is a spacer group.

In one embodiment there is provided a compound of the formula Ia wherein the R groups of each FL moiety are identical and are selected from the group consisting of straight chain or branched achiral $C_2$-$C_{10}$ alkyl, $C_2$-$C_{10}$ haloalkyl, $C_2$-$C_{10}$ fluoroalkyl, $C_2$-$C_{10}$ alkenyl group, optionally wherein 1, 2, or 3 $CH_2$ groups are replaced an oxygen no acetal, ketal, peroxide or vinyl ether is present in the R group, further wherein D, $B^1$, $B^2$, $B^3$, $S^1$, $S^{1a}$, $S^2$, $S^{2a}$, $S^3$, $Ar^1$, $Ar^2$, FL and n are defined as above for compounds of formula (I).

In one embodiment there is provided a compound of the formula Ib wherein the R groups of each FL moiety are identical and are selected from the group consisting of straight chain $C_2$-$C_{10}$ alkyl, $C_2$-$C_{10}$ haloalkyl, $C_2$-$C_{10}$ fluoroalkyl, $C_2$-$C_{10}$ alkenyl group, optionally wherein 1, 2, or 3 $CH_2$ groups are replaced an oxygen no acetal, ketal, peroxide or vinyl ether is present in the R group, further wherein D, $B^1$, $B^2$, $B^3$, $S^1$, $S^{1a}$, $S^2$, $S^{2a}$, $S^3$, $Ar^1$, $Ar^2$, FL and n are defined as above for compounds of formula (I).

In one embodiment there is provided a compound of the formula Ic wherein the R groups of each FL moiety are identical and are selected from the group consisting of straight chain or branched achiral $C_2$-$C_{10}$ alkyl and $C_2$-$C_{10}$ fluoroalkyl, further wherein D, $B^1$, $B^2$, $B^3$, $S^1$, $S^{1a}$, $S^2$, $S^{2a}$, $S^3$, $Ar^1$, $Ar^2$, FL and n are defined as above for compounds of formula (I).

In one embodiment there is provided a compound of the formula Id wherein the R groups of each FL moiety are identical and are selected from the group consisting of straight chain or branched achiral $C_1$-$C_{14}$ alkyl, $C_2$-$C_{10}$ alkyl, $C_3$-$C_8$ alkyl, methyl, ethyl, propyl, butyl, pentyl, hexyl, heptyl, octyl, nonyl, decyl, further wherein D, $B^1$, $B^2$, $B^3$, $S^1$, $S^{1a}$, $S^2$, $S^{2a}$, $S^3$, $Ar^1$, $Ar^2$, FL and n are defined as above for compounds of formula (I).

In one embodiment there is provided a compound of the formula Ie wherein the R groups of each FL moiety are identical and are selected from the group consisting of straight chain alkyl, $C_2$-$C_{10}$ alkyl, $C_3$-$C_8$ alkyl, methyl, ethyl, propyl, butyl, pentyl, hexyl, heptyl, octyl, nonyl, decyl, further wherein D, $B^1$, $B^2$, $B^3$, $S^1$, $S^{1a}$, $S^2$, $S^{2a}$, $S^3$, $Ar^1$, $Ar^2$, FL and n are defined as above for compounds of formula (I).

In one embodiment there is provided a compound of formula If wherein n is an integer from 1 to 6, optionally from 3 to 6, further wherein D, $B^1$, $B^2$, $B^3$, $S^1$, $S^{1a}$, $S^2$, $S^{2a}$, $S^3$, $Ar^1$, $Ar^2$, FL and R are defined as above for compounds of formula (I), (Ia), (Ib), (Ic), (Id) or (Ie).

In one embodiment there is provided a compound of formula Ig wherein n is an integer from 3 to 6, further wherein D, $B^1$, $B^2$, $B^3$, $S^1$, $S^{1a}$, $S^2$, $S^{2a}$, $S^3$, $Ar^1$, $Ar^2$, FL and R are defined as above for compounds of formula (I), (Ia), (Ib), (Ic), (Id) or (Ie).

In one embodiment there is provided a compound of formula Ih wherein $Ar^1$ and $Ar^2$ in each occurrence are independently selected from the group comprising $Ar^a$ and a bond, wherein $Ar^a$ represents a diradical comprising 1 aromatic, heteroaromatic or FL moiety, or 2 or 3 aromatic, heteroaromatic and/or FL moieties mutually connected by a single bond, further wherein D, $B^1$, $B^2$, $B^3$, $S^1$, $S^{1a}$, $S^2$, $S^{2a}$, $S^3$, FL, R and n are defined as above for compounds of formula (I), (Ia), (Ib), (Ic), (Id), (Ie), (If) or (Ig).

In one embodiment there is provided a compound of formula Ii wherein $Ar^1$ and $Ar^2$ in each occurrence are independently selected from the group comprising $Ar^a$ and a bond, wherein $Ar^a$ represents a diradical comprising 1 aromatic, heteroaromatic or FL moiety, or 2 or 3 aromatic, heteroaromatic and/or FL moieties mutually connected by single bonds, and wherein the aromatic and heteroaromatic moieties are in each occurrence independently selected from the group consisting of 1,4-phenylene, biphenyl-4,4'-diyl, terphenyl-4,4"-diyl, naphthalene-1,4-diyl, naphthalene-2,6-diyl, thiophene-2,5-diyl, pyrimidine-2,5-diyl, pyridine-2,5-diyl, perylene-3,10-diyl, pyrene-2,7-diyl, 2,2'-dithiophene-5,5'-diyl, oxazole-2,5-diyl, 1,3,4-oxadiazole-2,5-diyl, thieno[3,2-b]thiophene-2,5-diyl, dithieno[3,2-b:2',3'-d]thiophene-2,6-diyl, dibenzothiophene-3,7-diyl, benzo[1,2-b:4,5-b']bis[1]benzothiophene-3,9-diyl, thiazolo[5,4-d]thiazole-2,5-diyl, oxazolo[5,4-d]oxazole-2,5-diyl, thiazolo[5,4-d]oxazole-2,5-diyl, thiazolo[4,5-d]thiazole-2,5-diyl, oxazolo[4,5-d]oxazole-2,5-diyl, thiazolo[4,5-d]oxazole-2,5-diyl, 2,1,3-benzothiadiazole-4,7-diyl, 4-thien-2-yl-2,1,3-benzothiazole-7,5'-diyl, 4,7-dithien-2-yl-2,1,3-benzothiazole-5',5"-diyl, imidazo[4,5-d]imidazole-2,5-diyl, 4-alkyl-1,2,4-triazole-3,5-diyl, 4-aryl-1,2,4-triazole-3,5-diyl, 4-phenyl-1,2,4-triazole-3,5-diyl, 4-(p-tert-butylphenyl)-1,2,4-triazole-3,5-diyl, di-1,2,4-triazolo[4,5-f:4,5-q]-5,6,12,13-tetrahydro-5,12-diazadibenz[a,h]anthracene-5,13-diyl, 9-alkylcarbazole-2,7-diyl, 6,12-dialkylindolo[2,3-b]carbazole-2,8-diyl, benzo[1,2-b:4,5-b']dithiophene-2,6-diyl, benzo[1,2-b:5,4-bi]dithiophene-2,6-diyl, [1]benzothieno[3,2-b][1]benzothiophene-2,7-diyl, benzo[1,2-d:4,5-d']bisoxazole-2,6-diyl, benzo[1,2-d:5,4-d]bisoxazole-2,6-diyl, 5,5-dioxodibenzothiophene-3,7-diyl, or 6,12-dialkyl-5,5-11,11-tetraoxobenzo[1,2-b:4,5-b']bis[1]benzothiophene-3,9-diyl diradicals, further wherein D, $B^1$, $B^2$, $B^3$, $S^1$, $S^{1a}$, $S^2$, $S^{2a}$, $S^3$, FL, R and n are defined as above for compounds of formula (I), (Ia), (Ib), (Ic), (Id), (Ie), (If) or (Ig).

In one embodiment (e.g. an embodiment in which the compounds are to be used as hole transporting materials) there is provided a compound of formula Ij wherein $Ar^1$ and $Ar^2$ in each occurrence are independently selected from the group comprising $Ar^a$ and a bond, wherein and $Ar^a$ represents a diradical comprising 1 aromatic, heteroaromatic or FL moiety, or 2 or 3 aromatic, heteroaromatic and/or FL moieties mutually connected by single bonds, and wherein the aromatic and heteroaromatic moieties are in each occurrence independently selected from the group consisting of 1,4-phenylene, biphenyl-4,4'-diyl, terphenyl-4,4"-diyl, naphthalene-1,4-diyl, naphthalene-2,6-diyl, thiophene-2,5-diyl, perylene-3,10-diyl, pyrene-2,7-diyl, 2,2'-dithiophene-5,5'-diyl, thieno[3,2-b]thiophene-2,5-diyl, dithieno[3,2-b:2',3'-d]thiophene-2,6-diyl, dibenzothiophene-3,7-diyl, benzo[1,2-b:4,5-b']bis[1]benzothiophene-3,9-diyl, 9-alkylcarbazole-2,7-diyl, 6,12-dialkylindolo[2,3-b]carbazole-2,8-diyl, benzo[1,2-b:4,5-b]dithiophene-2,6-diyl, benzo[1,2-b:5,4-b']dithiophene-2,6-diyl, or [1]benzothieno[3,2-b][1]benzothiophene-2,7-diyl diradicals, further wherein D, $B^1$, $B^2$, $B^3$, $S^1$, $S^{1a}$, $S^2$, $S^{2a}$, $S^3$, FL, R and n are defined as above for compounds of formula (I), (Ia), (Ib), (Ic), (Id), (Ie), (If) or (Ig).

In one embodiment (e.g. an embodiment in which the compounds are to be used as electron transporting materials) there is provided a compound of formula Ik wherein $Ar^1$ and $Ar^2$ in each occurrence are independently selected from the group comprising $Ar^a$ and a bond, wherein and $Ar^a$ represents a diradical comprising 1 aromatic, heteroaromatic or FL moiety, or 2 or 3 aromatic, heteroaromatic and/or FL moieties mutually connected by single bonds, and wherein the aromatic and heteroaromatic moieties are in each occurrence independently selected from the group consisting of 1,4-phenylene, biphenyl-4,4'-diyl, terphenyl-4,4"-diyl, naphthalene-1,4-diyl, naphthalene-2,6-diyl, pyrimidine-2,5-diyl, perylene-3,10-diyl, pyrene-2,7-diyl, oxazole-2,5-diyl, 1,3,4-oxadiazole-2,5-diyl, oxazolo[4,5-d]oxazole-2,5-diyl, oxazolo[5,4-d]oxazole-2,5-diyl, 4-alkyl-1,2,4-triazole-3,5- diyl, 4-aryl-1,2,4-triazole-3,5-diyl, 4-phenyl-1,2,4-triazole-3,5-diyl, 4-(p-tert-butylphenyl)-1,2,4-triazole-3,5-diyl, di-1,2,4-triazolo[4,5-f:4,5-q]-5,6,12,13-tetrahydro-5,12-diazadibenz[a,h]anthracene-5,13-diyl, imidazo[4,5-d]imidazole-2,5-diyl, benzo[1,2-d:4,5-d']bisoxazole-2,6-diyl, benzo[1,2-d:5,4-d']bisoxazole-2,6-diyl, 5,5-dioxodibenzothiophene-3,7-diyl, or 6,12-dialkyl-5,5-11,11-tetraoxobenzo[1,2-b:4,5-b']bis[1]benzothiophene-3,9-diyl diradicals and further wherein D, $B^1$, $B^2$, $B^3$, $S^1$, $S^{1a}$, $S^2$, $S^{2a}$, $S^3$, FL, R and n are defined as above for compounds of formula (I), (Ia), (Ib), (Ic), (Id), (Ie), (If) or (Ig).

In one embodiment there is provided a compound of formula IL wherein $S^1$, $S^{1a}$, $S^2$ and $S^{2a}$ in each occurrence are independently selected from straight chain or branched achiral $C_5$-$C_{14}$ alkyl groups, optionally wherein 1, 2, 3, 4 or 5 methylene groups are substituted for an oxygen atom provided that no acetal, ketal or peroxide is present, that is connected to A through either a bond or an ether, ester, carbonate, thioether, amine or amide linkage and that is connected through either a bond or an ether, ester, carbonate, thioether, amine or amide linkage to D, $B^1$, $B^2$, $B^3$ or $S^3$ as determined by the nature of D, further wherein D, $B^1$, $B^2$, $B^3$, $S^3$, $Ar^1$, $Ar^2$, FL, R and n are defined as above for compounds of formula (I), (Ia), (Ib), (Ic), (Id), (Ie), (If), (Ig), (Ih), (Ii), (Ij) or (Ik).

In one embodiment there is provided a compound of formula Im wherein $S^1$, $S^{1a}$, $S^2$ and $S^{2a}$ in each occurrence are independently selected from straight chain or branched achiral $C_5$-$C_{14}$ alkyl groups, optionally wherein 1, 2, 3, 4 or 5 methylene groups are substituted for an oxygen atom provided that no acetal, ketal or peroxide is present, that is connected to A through either a bond or an ether, ester or carbonate linkage and that is connected through a bond, an ether, ester or carbonate linkage to D, $B^1$, $B^2$, $B^3$ or $S^3$ as determined by the nature of D, further wherein D, $B^1$, $B^2$, $B^3$, $S^3$, $Ar^1$, $Ar^2$, FL, R and n are defined as above for compounds of formula (I), (Ia), (Ib), (Ic), (Id), (Ie), (If), (Ig), (Ih), (Ii), (Ij) or (Ik).

In one embodiment there is provided a compound of formula In wherein $S^1$, $S^{1a}$, $S^2$, and $S^{2a}$ in each occurrence are independently selected from straight chain or branched achiral $C_7$-$C_{12}$ alkyl groups, optionally wherein 1, 2, 3 or 4 methylene groups are substituted for an oxygen atom provided that no acetal, ketal or peroxide is produced, that is connected to A through either a bond or an ether, ester, carbonate, thioether, amine or amide linkage and that is connected through a bond, an ether, ester, carbonate, thioether, amine or amide linkage to D, $B^1$, $B^2$, $B^3$ or $S^3$ as determined by the nature of D, further wherein D, $B^2$, $B^3$, $S^3$, $Ar^1$, $Ar^2$, FL, R and n are defined as above for compounds of formula (I), (Ia), (Ib), (Ic), (Id), (Ie), (If), (Ig), (Ih), (Ii), (Ij) or (Ik).

In one embodiment there is provided a compound of formula Io wherein $S^1$, $S^{1a}$, $S^2$ and $S^{2a}$ in each occurrence are independently selected from straight chain or branched achiral $C_7$-$C_{12}$ alkyl groups, optionally wherein 1, 2, 3 or 4 methylene groups are substituted for an oxygen atom provided that no acetal, ketal or peroxide is produced, that is connected to A through either a bond or an ether, ester or carbonate linkage and that is connected through a bond, an ether, ester or carbonate linkage to D, $B^1$, $B^2$, $B^3$ or $S^3$ as determined by the nature of D, further wherein D, $B^1$, $B^2$, $B^3$, $S^3$, $Ar^1$, $Ar^2$, FL, R and n are defined as above for compounds of formula (I), (Ia), (Ib), (Ic), (Id), (Ie), (If), (Ig), (Ih), (Ii), (Ij) or (Ik).

In one embodiment there is provided a compound of formula Ip wherein $B^1$, $B^2$, $B^3$, and D when it represents a crosslinking group in each occurrence independently represents a radiation activated cross linking group, optionally a photopolymerisable cross linking group, further wherein $S^1$, $S^{1a}$, $S^2$, $S^{2a}$, $S^3$, $Ar^1$, $Ar^2$, R and n are defined as above for compounds of formula (I), (Ia), (Ib), (Ic), (Id), (Ie), (If), (Ig), (Ih), (Ii), (Ij), (Ik), (IL), (Im), (In), or (Io).

In one embodiment there is provided a compound of formula Iq wherein $B^1$, $B^2$, $B^3$, and D when it represents a crosslinking group in each occurrence is selected from the group comprising alkene cross linking groups, further wherein $S^1$, $S^{1a}$, $S^2$, $S^{2a}$, $S^3$, $Ar^1$, $Ar^2$, FL, R and n are defined as above for compounds of formula (I), (Ia), (Ib), (Ic), (Id), (Ie), (If), (Ig), (Ih), (Ii), (Ij), (Ik), (IL), (Im), (In), or (Io).

In one embodiment there is provided a compound of formula Ir wherein $B^1$, $B^2$, $B^3$, and D when it represents a crosslinking group in each occurrence independently represents an electron rich or electron poor alkene cross linking group, further wherein $S^1$, $S^{1a}$, $S^2$, $S^{2a}$, $S^3$, $Ar^1$, $Ar^2$, FL, R and n are defined as above for compounds of formula (I), (Ia), (Ib), (Ic), (Id), (Ie), (If), (Ig), (Ih), (Ii), (Ij), (Ik), (IL), (Im), (In), or (Io).

In one embodiment there is provided a compound of formula Is wherein $B^1$, $B^2$, $B^3$, and D when it represents a crosslinking group in each occurrence independently represents a photopolymerisable alkene cross linking group, further wherein $S^1$, $S^{1a}$, $S^2$, $S^{2a}$, $S^3$, $Ar^1$, $Ar^2$, FL, R and n are defined as above for compounds of formula (I), (Ia), (Ib), (Ic), (Id), (Ie), (If), (Ig), (Ih), (Ii), (Ij), (Ik), (IL), (Im), (In), or (Io).

In one embodiment there is provided a compound of formula It wherein $B^1$, $B^2$, $B^3$, and D when it represents a crosslinking group in each occurrence independently represents an alkene cross linking group selected from the group consisting of straight chain and cyclic α,β-unsaturated esters, α,β-unsaturated amides, vinyl ethers, non-conjugated dienes further wherein $S^1$, $S^{1a}$, $S^2$, $S^{2a}$, $S^3$, $Ar^1$, $Ar^2$, FL, R and n are defined as above for compounds of formula (I), (Ia), (Ib), (Ic), (Id), (Ie), (If), (Ig), (Ih), (Ii), (Ij), (Ik), (IL), (Im), (In), or (Io).

In one embodiment there is provided a compound of formula Iu wherein $B^1$, $B^2$, $B^3$, and D when it represents a crosslinking group in each occurrence independently represents an alkene cross linking group selected from the group consisting of methacrylate, ethacrylate, ethylmaleato, ethylfumarato, N-maleimido, vinyloxy, alkylvinyloxy, vinylmaleato, vinylfumarato, N-(2-vinyloxymaleimido), 1,4-pentadien-3-yl and 1,4-cyclohexadienyl groups further wherein $S^1$, $S^{1a}$, $S^2$, $S^{2a}$, $S^3$, $Ar^1$, $Ar^2$, FL, R and n are defined as above for compounds of formula (I), (Ia), (Ib), (Ic), (Id), (Ie), (If), (Ig), (Ih), (Ii), (Ij), (Ik), (IL), (Im), (In), or (Io).

In one embodiment there is provided a compound of formula Iv wherein $S^3$ represents a $C_1$-$C_{20}$ alkyl group, $C_1$-$C_{20}$ haloalkyl group, a $C_3$-$C_8$ cycloalkyl group, a $C_6$-$C_{16}$ aryl group or a $C_4$-$C_{15}$ heteroaryl group or a chain consisting of 1, 2, 3, 4 or 5 $C_1$-$C_{20}$ alkyl, $C_1$-$C_{20}$ haloalkyl, $C_3$-$C_8$ cycloalkyl, $C_6$-$C_{16}$ aryl and/or $C_4$-$C_{15}$ heteroaryl moieties each independently connected by a bond, an ether linkage or an ester linkage and wherein $S^1$, $S^{1a}$, $S^2$, $S^{2a}$, D, $B^1$, $B^2$, $B^3$, $Ar^1$, $Ar^2$, FL, R and n are defined as above for compounds of formula (I), (Ia), (Ib), (Ic), (Id), (Ie), (If), (Ig), (Ih), (Ii), (Ij), (Ik), (IL), (Im), (In), (Io), (Ip), (Iq), (Ir), (Is), (It) or (Iu).

In one embodiment there is provided a compound of formula Iw wherein $S^3$ represents a $C_1$-$C_{14}$ alkyl group, $C_1$-$C_{14}$ haloalkyl group, a $C_5$-$C_6$ cycloalkyl group, a $C_6$-$C_{14}$ aryl group or a chain consisting of 1, 2, 3, 4 or 5 $C_1$-$C_{14}$ alkyl, $C_1$-$C_{14}$ haloalkyl, $C_3$-$C_8$ cycloalkyl and/or $C_6$-$C_{14}$ aryl moieties each independently connected by a bond, an ether linkage or an ester linkage wherein $S^1$, $S^{1a}$, $S^2$, $S^{2a}$, D, $B^1$, $B^2$, $B^3$, $Ar^1$, $Ar^2$, FL, R and n are defined as above for compounds of formula (I), (Ia), (Ib), (Ic), (Id), (Ie), (If), (Ig), (Ih), (Ii), (Ij), (Ik), (IL), (Im), (In), (Io), (Ip), (Iq), (Ir), (Is), (It) or (Iu).

In one embodiment there is provided a compound of formula Ix wherein $S^3$ represents a $C_2$-$C_{10}$ alkyl group, $C_2$-$C_{10}$ haloalkyl group, a $C_5$-$C_6$ cycloalkyl group, a $C_6$-$C_{14}$ aryl group or a chain consisting of 1, 2, 3, 4 or 5 $C_1$-$C_{14}$ alkyl, $C_2$-$C_{10}$ haloalkyl, $C_3$-$C_8$ cycloalkyl and/or $C_6$-$C_{14}$ aryl moieties each independently connected by a bond, an ether linkage or an ester linkage wherein $S^1$, $S^{1a}$, $S^2$, $S^{2a}$, D, $B^1$, $B^2$, $B^3$, $Ar^1$, $Ar^2$, FL, R and n are defined as above for compounds of formula (I), (Ia), (Ib), (Ic), (Id), (Ie), (If), (Ig), (Ih), (Ii), (Ij), (Ik), (IL), (Im), (In), (Io), (Ip), (Iq), (Ir), (Is), (It) or (Iu).

In one embodiment there is provided a compound of formula Iy wherein $S^3$ represents a group consisting of three $C_2$-$C_{12}$ alkyl groups and two $C_6$-$C_{16}$ aryl groups mutually connected to each other by a bond, an ether linkage or an ester linkage; wherein each $C_6$-$C_{16}$ aryl group is connected i) to the second $C_6$-$C_{16}$ aryl group by a $C_2$-$C_{12}$ alkyl group, ii) to a cross linker $B^2$ or $B^3$ by a $C_2$-$C_{12}$ alkyl group and iii) directly to $S^1$ and $S^{1a}$ and wherein $S^1$, $S^{1a}$, $S^2$, $S^{2a}$, D, $B^1$, $B^2$, $B^3$, $Ar^1$, $Ar^2$, FL, R and n are defined as above for compounds of formula (I), (Ia), (Ib), (Ic), (Id), (Ie), (If), (Ig), (Ih), (Ii), (Ij), (Ik), (IL), (Im), (In), (Io), (Ip), (Iq), (Ir), (Is), (It) or (Iu).

In one embodiment there is provided a compound of formula Iz wherein $S^3$ represents a group consisting of four $C_2$-$C_{12}$ alkyl groups connected to a central $C_6$-$C_{16}$ aryl group mutually connected to each other by a bond, an ether linkage or an ester linkage wherein the end of each independent $C_2$-$C_{12}$ alkyl group not attached to the central $C_6$-$C_{16}$ aryl group terminates in a connection to $B^2$, $B^3$, $S^1$ and $S^{1a}$ and wherein $S^1$, $S^{1a}$, $S^2$, $S^{2a}$, D, $B^1$, $B^2$, $B^3$, $Ar^1$, $Ar^2$, FL, R and n are defined as above for compounds of formula (I), (Ia), (Ib), (Ic), (Id), (Ie), (If), (Ig), (Ih), (Ii), (Ij), (Ik), (IL), (Im), (In), (Io), (Ip), (Iq), (Ir), (Is), (It) or (Iu).

In one embodiment there is provided a network polymer formed by crosslinking a plurality of monomers of the formula (I), (Ia), (Ib), (Ic), (Id), (Ie), (If), (Ig), (Ih), (Ii), (Ij), (Ik), (IL), (Im), (In), (Io), (Ip), (Iq), (Ir), (Is), (It), (Iu). (Iv), (Iw), (Ix), (Iy) or (Iz).

In one embodiment there is provided a compound with a structure according formula (I), (Ia), (Ib), (Ic), (Id), (Ie), (If), (Ig), (Ih), (Ii), (Ij), (Ik), (IL), (Im), (In), (Io), (Ip), (Iq), (Ir), (Is), (It), (Iu). (Iv), (Iw), (Ix), (Iy) or (Iz) for use in the fabrication of an OLED device.

In one embodiment there is provided an OLED device with an emissive layer that contains 2,7-disubstituted 9,9-fluoroalkyl fluorene diradicals of the formula

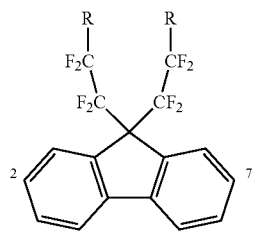

wherein R represents a straight chain or branched achiral $C_1$-$C_{14}$ alkyl, $C_1$-$C_{14}$ haloalkyl or $C_2$-$C_{14}$ alkenyl group, optionally wherein 1, 2, 3, 4 or 5 of the methylene groups of R are replaced by an oxygen atom provided that no acetal, ketal, peroxide or vinyl ether is present, and partially or fully fluorinated derivatives of these groups.

In one embodiment there is provided an OLED device with an emissive layer containing i) a plurality of compounds of the formula (I), (Ia), (Ib), (Ic), (Id), (Ie), (If), (Ig), (Ih), (Ii), (Ij), (Ik), (IL), (Im), (In), (Io), (Ip), (Iq), (Ir), (Is), (It), (Iu). (Iv), (Iw), (Ix), (Iy) or (Iz); or ii) a network polymer formed (or obtainable) by crosslinking a plurality of monomers of the formula (I), (Ia), (Ib), (Ic), (Id), (Ie), (If), (Ig), (Ih), (Ii), (Ij), (Ik), (IL), (Im), (In), (Io), (Ip), (Iq), (Ir), (Is), (It), (Iu). (Iv), (Iw), (Ix), (Iy) or (Iz).

In one embodiment there is provided an OLED device with a polymeric emissive layer that contains 2,7-disubstituted 9,9-fluoroalkyl fluorene diradicals of the formula

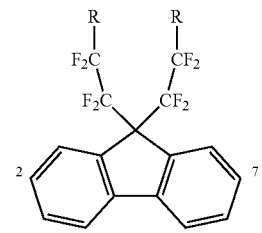

wherein R represents a straight chain or branched achiral $C_1$-$C_{14}$ alkyl, $C_1$-$C_{14}$ haloalkyl or $C_2$-$C_{14}$ alkenyl group, optionally wherein 1, 2, 3, 4 or 5 of the methylene groups of R are replaced by an oxygen atom provided that no acetal, ketal, peroxide or vinyl ether is present, and partially or fully fluorinated derivatives of these groups, further wherein the polymeric emissive layer is formed (or is obtainable) by exposing a plurality of monomers to radiation, optionally wherein the radiation is ultraviolet light.

In one embodiment there is provided an OLED device containing a polymeric emissive layer formed (or obtainable) by exposing a plurality of monomers of the formula (I), (Ia), (Ib), (Ic), (Id), (Ie), (If), (Ig), (Ih), (Ii), (Ij), (Ik), (IL), (Im), (In), (Io), (Ip), (Iq), (Ir), (Is), (It), (Iu). (Iv), (Iw), (Ix), (Iy) or (Iz) to radiation, optionally wherein the radiation is ultraviolet light.

In one embodiment there is provided a device with a charge transport layer that contains 2,7-disubstituted 9,9-fluoroalkyl fluorene diradicals of the formula

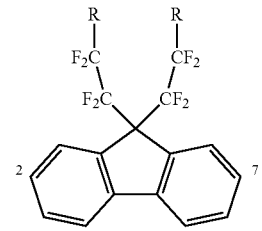

wherein R represents a straight chain or branched achiral $C_1$-$C_{14}$ alkyl, $C_1$-$C_{14}$ haloalkyl or $C_2$-$C_{14}$ alkenyl group, optionally wherein 1, 2, 3, 4 or 5 of the methylene groups of R are replaced by an oxygen atom provided that no acetal, ketal, peroxide or vinyl ether is present, and partially or fully fluorinated derivatives of these groups.

In one embodiment here is provided a device containing a charge transport layer containing i) a plurality of compounds of the formula (I), (Ia), (Ib), (Ic), (Id), (Ie), (If), (Ig), (Ih), (Ii), (Ij), (Ik), (IL), (Im), (In), (Io), (Ip), (Iq), (Ir), (Is), (It), (Iu). (Iv), (Iw), (Ix), (Iy) or (Iz); or ii) a network polymer formed (or obtainable) by crosslinking a plurality of monomers of the formula (I), (Ia), (Ib), (Ic), (Id), (Ie), (If), (Ig), (Ih), (Ii), (Ij), (Ik), (IL), (Im), (In), (Io), (Ip), (Iq), (Ir), (Is), (It), (Iu). (Iv), (Iw), (Ix), (Iy) or (Iz).

In one embodiment there is provided a device with a polymeric charge transport layer that contains 2,7-disubstituted 9,9-fluoroalkyl fluorene diradicals of the formula

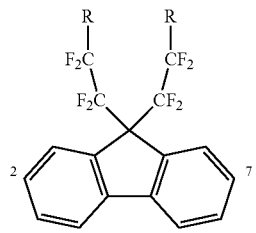

wherein R represents a straight chain or branched achiral $C_1$-$C_{14}$ alkyl, $C_1$-$C_{14}$ haloalkyl or $C_2$-$C_{14}$ alkenyl group, optionally wherein 1, 2, 3, 4 or 5 of the methylene groups of R are replaced by an oxygen atom provided that no acetal, ketal, peroxide or vinyl ether is present, and partially or fully fluorinated derivatives of these groups, further wherein the polymeric emissive layer is formed (or is obtainable) by exposing the monomers to radiation, optionally wherein the radiation is ultraviolet light.

In one embodiment there is provided a device containing a polymeric charge transport layer formed (or obtainable) by exposing a plurality of monomers of the formula (I), (Ia), (Ib), (Ic), (Id), (Ie), (If), (Ig), (Ih), (Ii), (Ij), (Ik), (IL), (Im), (In), (Io), (Ip), (Iq), (Ir), (Is), (It), (Iu). (Iv), (Iw), (Ix), (Iy) or (Iz) to radiation, optionally wherein the radiation is ultraviolet light.

In one embodiment there is provided a device comprising a charge transporting layer that contains 2,7-disubstituted 9,9-fluoroalkyl fluorene diradicals of the formula

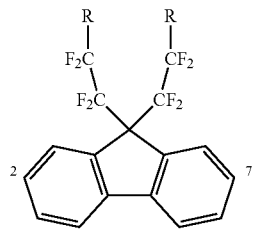

wherein R represents a straight chain or branched achiral $C_1$-$C_{14}$ alkyl, $C_1$-$C_{14}$ haloalkyl or $C_2$-$C_{14}$ alkenyl group, optionally wherein 1, 2, 3, 4 or 5 of the methylene groups of R are replaced by an oxygen atom provided that no acetal, ketal, peroxide or vinyl ether is present, and partially or fully fluorinated derivatives of these groups.

In one embodiment there is provided a device comprising an interface between a hole transporting layer and an electron transporting layer, wherein either or both of said layers is a layer that contains 2,7-disubstituted 9,9-fluoroalkyl fluorene diradicals of the formula

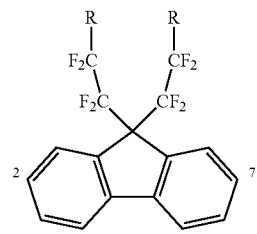

wherein R represents a straight chain or branched achiral $C_1$-$C_{14}$ alkyl, $C_1$-$C_{14}$ haloalkyl or $C_2$-$C_{14}$ alkenyl group, optionally wherein 1, 2, 3, 4 or 5 of the methylene groups of R are replaced by an oxygen atom provided that no acetal, ketal, peroxide or vinyl ether is present, and partially or fully fluorinated derivatives of these groups.

In one embodiment there is provided a device comprising an interface between a hole transporting layer and an electron transporting layer as described above, further wherein the device is a photovoltaic device or a thin film transistor (TFT) device.

In one embodiment there is provided a device containing a plurality of layers that comprise 2,7-disubstituted 9,9-fluoroalkyl fluorene diradicals of the formula

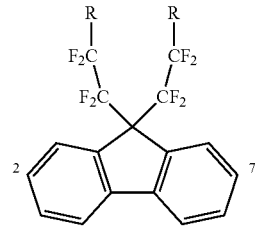

wherein R represents a straight chain or branched achiral $C_1$-$C_{14}$ alkyl, $C_1$-$C_{14}$ haloalkyl or $C_2$-$C_{14}$ alkenyl group, optionally wherein 1, 2, 3, 4 or 5 of the methylene groups of R are replaced by an oxygen atom provided that no acetal, ketal, peroxide or vinyl ether is present, and partially or fully fluorinated derivatives of these groups, further wherein each layer is formed (or is obtainable) by an iterative sequential deposition and in situ polymerisation process.

In one embodiment there is provided a device containing a plurality of patterned structures produced (or obtainable) by exposing a plurality of layers of material comprising 2,7-disubstituted 9,9-fluoroalkyl fluorene diradicals of the formula

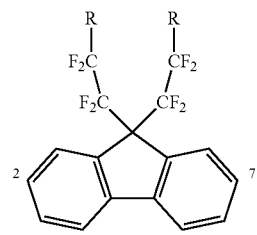

wherein R represents a straight chain or branched achiral $C_1$-$C_{14}$ alkyl, $C_1$-$C_{14}$ haloalkyl or $C_2$-$C_{14}$ alkenyl group, optionally wherein 1, 2, 3, 4 or 5 of the methylene groups of R are replaced by an oxygen atom provided that no acetal, ketal, peroxide or vinyl ether is present, and partially or fully fluorinated derivatives of these groups, to a patterned area of radiation, such as ultraviolet light, that causes said layer of material to polymerise and then washing away the unexposed and unpolymerised material.

In one embodiment there is provided a device that contains two or more of the aforementioned patterned structures, said structures being comprised of materials that are electroluminescent in nature, wherein the wavelength of electroluminescence emitted by one patterned structure is different to the wavelength of electroluminescence emitted by at least one other patterned structure.

In one embodiment there is provided a multicolour, dot-matrix display comprising a multiplicity of pixels of multiple colours each pixel comprising one or more of the aforementioned patterned structures.

In one embodiment there is provided a device that contains two or more of the aforementioned patterned structures, said structures being comprised of materials that are electroluminescent in nature, wherein two or more of the aforementioned patterned structures are overlayed in a stack, further wherein the electroluminescent wavelength of two or more of the patterned structures in each stack is different.

In one embodiment there is provided a device containing a polymerised liquid crystalline material that comprises 2,7-disubstituted 9,9-fluoroalkyl fluorene diradicals of the formula

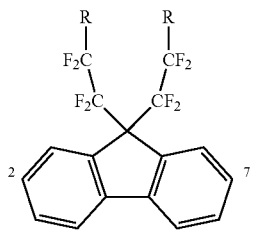

wherein R represents a straight chain or branched achiral $C_1$-$C_{14}$ alkyl, $C_1$-$C_{14}$ haloalkyl or $C_2$-$C_{14}$ alkenyl group, optionally wherein 1, 2, 3, 4 or 5 of the methylene groups of R are replaced by an oxygen atom provided that no acetal, ketal, peroxide or vinyl ether is present, and partially or fully fluorinated derivatives of these groups.

In one embodiment there is provided a device containing a glass formed (or obtainable) by cooling a liquid crystalline material that comprises 2,7-disubstituted 9,9-fluoroalkyl fluorene diradicals of the formula

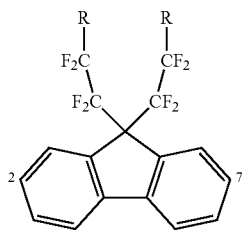

wherein R represents a straight chain or branched achiral $C_1$-$C_{14}$ alkyl, $C_1$-$C_{14}$ haloalkyl or $C_2$-$C_{14}$ alkenyl group, optionally wherein 1, 2, 3, 4 or 5 of the methylene groups of R are replaced by an oxygen atom provided that no acetal, ketal, peroxide or vinyl ether is present, and partially or fully fluorinated derivatives of these groups.

In one embodiment there is provided a device containing a polymerised nematic liquid crystalline material that comprises 2,7-disubstituted 9,9-fluoroalkyl fluorene diradicals of the formula

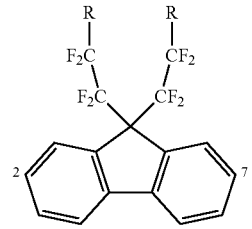

wherein R represents a straight chain or branched achiral $C_1$-$C_{14}$ alkyl, $C_1$-$C_{14}$ haloalkyl or $C_2$-$C_{14}$ alkenyl group, optionally wherein 1, 2, 3, 4 or 5 of the methylene groups of R are replaced by an oxygen atom provided that no acetal, ketal, peroxide or vinyl ether is present, and partially or fully fluorinated derivatives of these groups.

In one embodiment there is provided an device containing a polymeric matrix, formed (or obtainable) by exposing a liquid crystalline fluid containing molecules comprising 2,7-disubstituted 9,9-fluoroalkyl fluorene diradicals of the formula

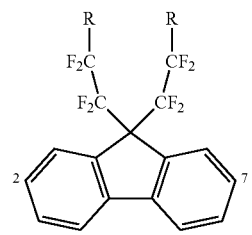

wherein R represents a straight chain or branched achiral $C_1$-$C_{14}$ alkyl, $C_1$-$C_{14}$ haloalkyl or $C_2$-$C_{14}$ alkenyl group, optionally wherein 1, 2, 3, 4 or 5 of the methylene groups of R are replaced by an oxygen atom provided that no acetal, ketal, peroxide or vinyl ether is present, and partially or fully fluorinated derivatives of these groups, to radiation, optionally wherein the radiation is ultraviolet light.

In one embodiment the OLED device containing a polymeric matrix described above is characterised in that the matrix comprises a nematic liquid crystalline structure which has been locked in place.

In one embodiment there is provided an OLED device containing a light emitting layer which comprises a material with a uniformly aligned liquid crystalline structure containing molecules comprising 2,7-disubstituted 9,9-fluoroalkyl fluorene diradicals of the formula

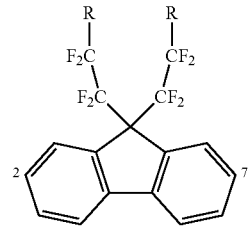

wherein R represents a straight chain or branched achiral $C_1$-$C_{14}$ alkyl, $C_1$-$C_{14}$ haloalkyl or $C_2$-$C_{14}$ alkenyl group, optionally wherein 1, 2, 3, 4 or 5 of the methylene groups of R are replaced by an oxygen atom provided that no acetal, ketal, peroxide or vinyl ether is present, and partially or fully fluorinated derivatives of these groups such that said light emitting layer emits linearly polarised light.

In one embodiment there is provided a method for forming a device containing a plurality of patterned structures, said method comprising exposing a plurality of layers of material comprising 2,7-disubstituted 9,9-fluoroalkyl fluorene diradicals of the formula

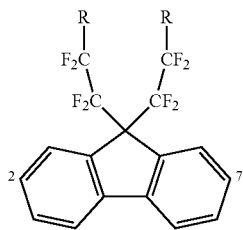

wherein R represents a straight chain or branched achiral $C_1$-$C_{14}$ alkyl, $C_1$-$C_{14}$ haloalkyl or $C_2$-$C_{14}$ alkenyl group, optionally wherein 1, 2, 3, 4 or 5 of the methylene groups of R are replaced by an oxygen atom provided that no acetal, ketal, peroxide or vinyl ether is present, and partially or fully fluorinated derivatives of these groups, to a patterned area of radiation, such as ultraviolet light, that causes said layer of material to polymerise and then washing away the unexposed and unpolymerised material.

In one embodiment there is provided a structure that is fabricated (or obtainable) by exposing a layer of uniformly aligned liquid crystalline fluid or a glass formed (or obtainable) by cooling a uniformly aligned liquid crystalline fluid that contains cross linkable molecules comprising 2,7-disubstituted 9,9-fluoroalkyl fluorene diradicals of the formula

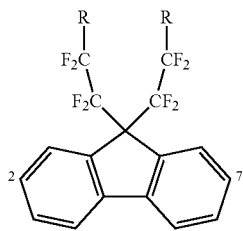

wherein R represents a straight chain or branched achiral $C_1$-$C_{14}$ alkyl, $C_1$-$C_{14}$ haloalkyl or $C_2$-$C_{14}$ alkenyl group, optionally wherein 1, 2, 3, 4 or 5 of the methylene groups of R are replaced by an oxygen atom provided that no acetal, ketal, peroxide or vinyl ether is present, and partially or fully fluorinated derivatives of these groups, to a patterned area of radiation, such as ultraviolet light, wherein said exposure to radiation causes said exposed layer of material to polymerise, and then washing away the unexposed and unpolymerised material.

In one embodiment there is provided a polarised light emitting structure that is fabricated (or obtainable) by exposing a layer of uniformly aligned liquid crystalline fluid or a glass formed (or obtainable) by cooling a uniformly aligned liquid crystalline fluid that contains cross linkable molecules comprising 2,7-disubstituted 9,9-fluoroalkyl fluorene diradicals of the formula

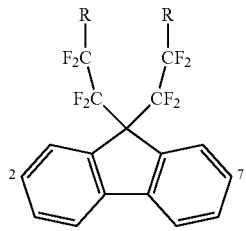

wherein R represents a straight chain or branched achiral $C_1$-$C_{14}$ alkyl, $C_1$-$C_{14}$ haloalkyl or $C_2$-$C_{14}$ alkenyl group, optionally wherein 1, 2, 3, 4 or 5 of the methylene groups of R are replaced by an oxygen atom provided that no acetal, ketal, peroxide or vinyl ether is present, and partially or fully fluorinated derivatives of these groups, to a patterned area of radiation, optionally ultraviolet light, wherein said exposure to radiation causes said exposed layer of material to polymerise, and then washing away the unexposed and unpolymerised material.

In one embodiment there is provided a device comprising two or more of the above described patterned polarised light emitting structures wherein at least a first polarised light emitting structure has a polarisation axis of light emission that is not aligned with that of at least a second polarised light emitting structure.

In one embodiment there is provided a 3D display produced (or obtainable) by sequential deposition of aligned layers of uniformly aligned liquid crystalline fluid or a glass formed (or obtainable) by cooling a uniformly aligned liquid crystalline fluid that contains cross linkable molecules comprising 2,7-disubstituted 9,9-fluoroalkyl fluorene diradicals of the formula

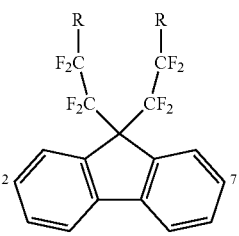

wherein R represents a straight chain or branched achiral $C_1$-$C_{14}$ alkyl, $C_1$-$C_{14}$ haloalkyl or $C_2$-$C_{14}$ alkenyl group, optionally wherein 1, 2, 3, 4 or 5 of the methylene groups of R are replaced by an oxygen atom provided that no acetal, ketal, peroxide or vinyl ether is present, and partially or fully fluorinated derivatives of these groups, sequential polymerisation of patterned areas of each layer in turn, and sequentially washing away unpolymerised areas of each layer in turn so as to provide light emitting structures such that the liquid crystalline alignment and thus the polarisation axis of light emission of each respective layer is in a different direction to that of the polarisation axis of light emission in the respective adjacent layers.

In one embodiment there is provided a device comprising a polymer comprising 2,7-disubstituted 9,9-fluoroalkyl fluorene repeat units

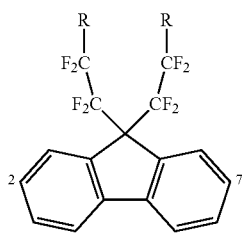

wherein R represents a straight chain or branched achiral $C_1$-$C_{14}$ alkyl, $C_1$-$C_{14}$ haloalkyl or $C_2$-$C_{14}$ alkenyl group, optionally wherein 1, 2, 3, 4 or 5 of the methylene groups of R are replaced by an oxygen atom provided that no acetal, ketal, peroxide or vinyl ether is present, and partially or fully fluorinated derivatives of these groups.

In one embodiment there is provided an OLED device comprising a light emitting polymer comprising the 2,7-disubstituted 9,9-fluoroalkyl fluorene repeat unit

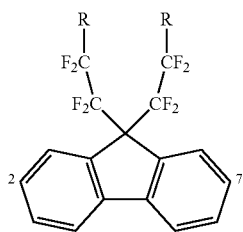

wherein R represents a straight chain or branched achiral $C_1$-$C_{14}$ alkyl, $C_1$-$C_{14}$ haloalkyl or $C_2$-$C_{14}$ alkenyl group, optionally wherein 1, 2, 3, 4 or 5 of the methylene groups of R are replaced by an oxygen atom provided that no acetal, ketal, peroxide or vinyl ether is present, and partially or fully fluorinated derivatives of these groups.

In one embodiment there is provided a OLED device containing a polymer comprising 2,7-disubstituted 9,9-fluoroalkyl fluorene repeat units

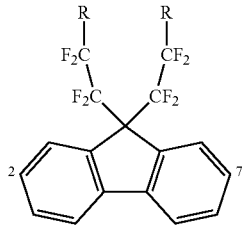

wherein R represents a straight chain or branched achiral $C_1$-$C_{14}$ alkyl, $C_1$-$C_{14}$ haloalkyl or $C_2$-$C_{14}$ alkenyl group, optionally wherein 1, 2, 3, 4 or 5 of the methylene groups of R are replaced by an oxygen atom provided that no acetal, ketal, peroxide or vinyl ether is present, and partially or fully fluorinated derivatives of these groups and in which this polymer is utilised as a light emitting dopant in a host material that has a liquid crystalline structure.

In one aspect the invention relates to the compound

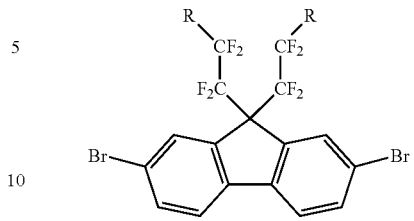

wherein R in each case is a straight chain or branched achiral $C_1$-$C_{14}$ alkyl, $C_1$-$C_{14}$ haloalkyl, $C_1$-$C_{14}$ fluoroalkyl, $C_2$-$C_{14}$ alkenyl group, optionally wherein 1, 2, 3, 4 or 5 $CH_2$ groups are replaced by an oxygen provided that no acetal, ketal, peroxide or vinyl ether is present in the R group. In a preferred embodiment R in each case is a straight or branched achiral $C_{2-10}$ alkyl group. In a preferred embodiment R in each case is a straight chain $C_{2-10}$ alkyl group. In a preferred embodiment of these compounds the R groups are identical.

In one aspect the invention relates to a process for making a material of structure $B^1$—$S^2$-A-$S^1$—$S^3(B^2)(B^3)$—$S^{a1}$-A-$S^{2a}$—$B^{1a}$ involving the step of alkylating a phenolic oxygen with a compound of structure

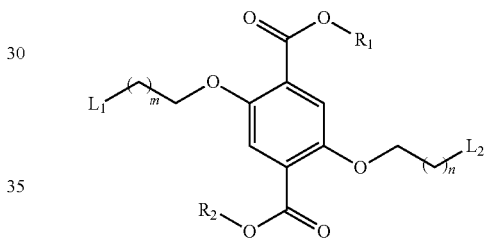

wherein $R_1$ and $R_2$ are independently $C_{1-12}$ alkyl, $C_{6-10}$ aryl or $C_{5-9}$ heteroaryl;

$L_1$ and $L_2$ are independently selected leaving groups, optionally selected from Cl, Br, I, O-Tosyl, O-Mesyl or O-Triflyl; and m and n are an integer from 1 to 10.

In one aspect the invention relates to diethyl-2,5-di(bromohexyl)oxyterephthalate, diethyl-2,5-di(chlorohexyl)oxyterephthalate, diethyl-2,5-di(iodohexyl)oxyterephthalate and analogous compounds with $C_{1-12}$ alkyl, $C_{6-10}$ aryl or $C_{5-9}$ heteroaryl ester groups. In one aspect the invention relates to the use of diethyl-2,5-di(bromohexyl)oxyterephthalate, diethyl-2,5-di(chlorohexyl)oxyterephthalate and diethyl-2,5-di(iodohexyl)oxyterephthalate and analogous compounds with methyl, propyl, butyl, pentyl and hexyl ester groups as intermediates for the elaboration of cross linkable materials with the general structure $S^3$ as defined for compound (I), (Iv), (Iw), (Ix) and (Iz) above.

DETAILED DESCRIPTION OF THE INVENTION

Figure 1:
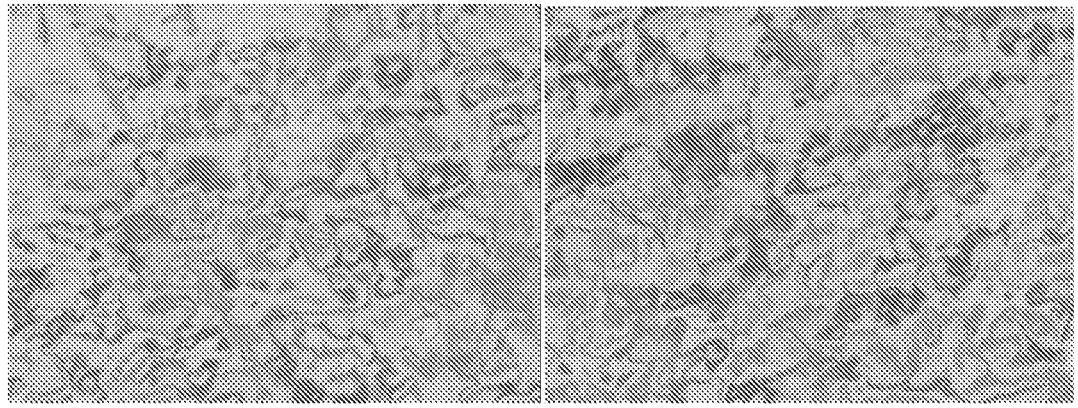
FIG. 1 is an optical microscopy image of a compound of the invention.

According to one aspect of the invention there is provided a compound of the D-$S^1$-A-$S^2$—$B^1$ wherein the groups D, $B^1$, $S^1$, $S^2$ and A are the chemical groups defined herein. A represents a group of the formula —$Ar^1$—(FL-$Ar^2$)$_n$—. The component parts of the system are connected to each other through covalent bonds.

This group may also be presented as a compound of formula 1

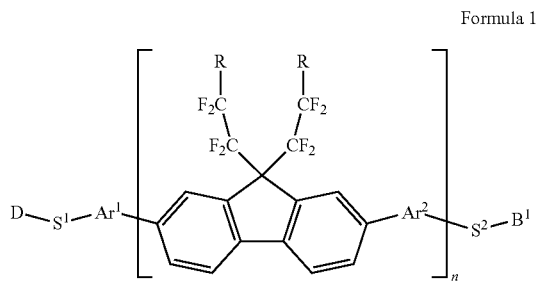

Formula 1

So that the invention may be better understood the nature of the constituent groups and their function is defined herein.

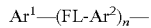

The compounds of the invention comprise a —$Ar^1$—(FL-$Ar^2$)$_n$— group, abbreviated as A, that forms a "substantially linear", or "lathe like", aromatic core of the compound. In this structure FL is a fluorene diradical of the structure below

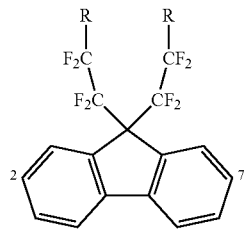

that is incorporated into the chain through covalent bonds at C-2 and C-7.

The integer n in —$Ar^1$—(FL-$Ar^2$)$_n$— is from 1 to 8. In total each —$Ar^1$—(FL-$Ar^2$)$_n$— group comprises from 1 to 8 FL groups. In certain preferred aspects, the number of FL each —$Ar^1$—(FL-$Ar^2$)$_n$— group is selected from 1 to 6, 1 to 3, 3 to 6, or 5, or 6.

In the preferred aspect where the compounds of the present invention are suitable for use as light emitters each —$Ar^1$—(FL-$Ar^2$)$_n$— group comprises between 3 and 6 FL groups. This is because lower n values lead to molecules with lower light emission efficiency. In embodiments where the compounds of the present invention are suitable for use as a hole transporter, an electron transporter, or a host for a light emitting dopant, —$Ar^1$—(FL-$Ar^2$)$_n$— groups with 1 to 3 FL groups are preferred because of their ease of synthesis, lower melting points and higher solubilities.

In this —$Ar^1$—(FL-$Ar^2$)$_n$— or A structure the R groups of each individual FL are identical when n is greater than 1 because of the potential for multiple isomers of the material that make purification challenging. For materials with n=1 having different R groups in different FL groups can be advantageous because this may cause the melting points to be lowered. The R groups are selected from straight chain or branched achiral $C_1$-$C_{14}$ alkyl, $C_1$-$C_{14}$ haloalkyl, fluoroalkyl, alkenyl group, optionally wherein 1, 2, 3, 4 or 5 $CH_2$ groups are replaced an oxygen so that no acetal, ketal, peroxide or vinyl ether is present. In other words, if more than one methylene group is replaced by an oxygen atom it will be separated from the next oxygen atom in the chain by at least three covalent bonds. When the R groups are alkenyl groups it is preferred that the alkene is a terminal alkene because the viscosity of the product can be lowered by incorporating a terminal alkene in the R group.

$Ar^1$ and $Ar^2$ in each occurrence are independently selected from the group comprising $Ar^a$ and a bond. $Ar^a$ represents a diradical comprising 1 aromatic, heteroaromatic or FL moiety, or 2, 3, 4 or 5 aromatic, heteroaromatic and/or FL moieties mutually connected by a single bond.

The overall $Ar^1$—(FL-$Ar^2$)$_n$ chain is "substantially linear" and is devoid of significant branching that would destroy its linearity, its ability to align with adjacent molecules and favours liquid crystallinity. Certain elements of the chain may project from the linear structure. For example, when $Ar^1$ is a naphthalene-1,4-diyl, carbons 5 to 8 project from the side of the chain even though the naphthyl structure is integral to the chain. It can be appreciated that although the chain as a whole is described as linear the nature of the chemical bonds that connect the component parts of the chain dictates that all the chemical bonds in the chain will not be exactly aligned. So long as any curvature in the backbone of the molecular core of the materials molecules does not destroy the liquid crystalline nature of the material or at least its ability to be aligned by liquid crystalline molecules said curvature is allowed. Similarly, branching that preserves the liquid crystalline nature of the material is also allowed.

R

R groups are selected from straight chain or branched achiral $C_1$-$C_{14}$ alkyl, $C_1$-$C_{14}$ haloalkyl, $C_1$-$C_{14}$ fluoroalkyl, $C_2$-$C_{14}$ alkenyl group, optionally wherein 1, 2, 3, 4 or 5 methylene ($CH_2$) groups are replaced an oxygen so that no acetal, ketal, peroxide or vinyl ether is present. In other words, if more than one methylene group is replaced by an oxygen atom it will be separated from the next oxygen atom in the chain by at least three covalent bonds and no oxygen atom is connected through a single bond to a carbon-carbon double bond. In some aspects the R groups of each individual fluorene are identical. In another aspect the R groups on every fluorene in the chain are identical.

In a preferred aspect the R groups of each FL moiety are identical and are selected from the group consisting of straight chain or branched achiral $C_2$-$C_{10}$ alkyl, $C_2$-$C_{10}$ haloalkyl, $C_2$-$C_{10}$ fluoroalkyl, $C_2$-$C_{10}$ alkenyl group, optionally wherein 1, 2, or 3 $CH_2$ groups are replaced an oxygen provided that no acetal, ketal or peroxide is present.

In a preferred aspect each hydrogen atom of each R group may be independently substituted by a fluorine atom. When an R group contains at least one fluorine substituent it can be referred to as a fluoroalkyl group. In a preferred aspect the fluoroalkyl group comprises at least one hydrogen atom. Haloalkyl groups include groups substituted by Fl, Cl, Br and I. Preferred haloalkyl groups are fluoroalkyl, chloroalkyl and fluorochloroalkyl groups.

In a preferred aspect the R group is an alkenyl group. Alkenyl groups contain a carbon-carbon double bond. Preferred alkenyl groups contain only one carbon carbon double bond. In a preferred aspect, where the R group is an alkenyl group it is a terminal carbon-carbon double bond. In a preferred aspect the terminal alkene is of the formula CH=CH$_2$.

As stated above, in some cases one or two or three or four or five methylene groups in the R group may be substituted for an oxygen atom. When this is the case the R group is an ether or polyether. The methylene group is a CH$_2$ group. When two or more methylene groups are replaced by an oxygen atom there are at least two carbon atoms in the chain between them. This is because peroxide, ketal, acetal and vinyl ether units are potentially unstable and are therefore not included in the structure of the compounds of the invention.

Variation of the length of the R group is useful because the melting point of the compound can be modulated. For example, when liquid crystalline compounds are required it can be advantageous to use R groups with from 2 to 14 carbon and oxygen atoms in the chain because $C_1$-hydrocarbyl derivatives often exhibit elevated melting points. In preferred aspects the R groups contain between 2 and 10 carbon and oxygen atoms in the chain.

Introduction of oxygen atoms into the R group can advantageously be used to modulate the temperature at which the compound undergoes its glass transition and this can be an advantage for applications when glassy materials are required.

Introduction of a carbon-carbon double can be advantageously used to reduce the viscosity of the material and this is especially interesting for compounds that are to be solution processed. Introduction of a carbon-carbon double bond at the chain terminus is especially advantageous for modulation of the viscosity of the material.

For application in electronic devices high purity material is required and the presence of any asymmetric centres in the hydrocarbyl group is disfavoured. For this reason, in the compounds of the invention wherein the R group is branched, the branching does not introduce a chiral centre. This achiral branching advantageously circumvents problems with purification that can be associated with diastereoisomeric mixtures of chemicals. Introduction of branching in the group R can advantageously be used to modulate the melting point of the compounds of the invention.

Selected examples of FL structure with the R group drawn out in full are presented below.

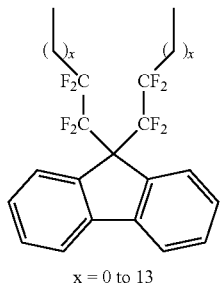

x = 0 to 13

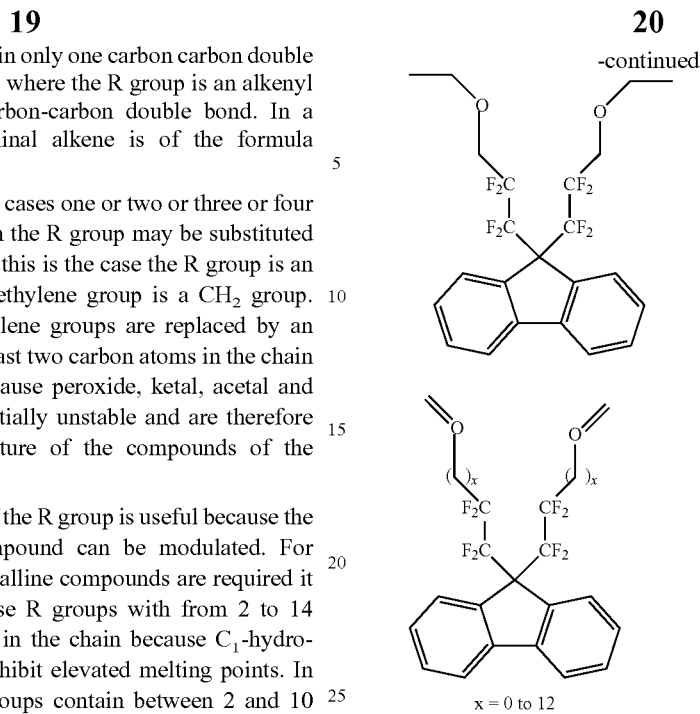

x = 0 to 12

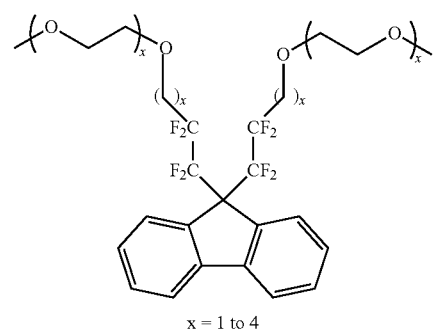

x = 1 to 4

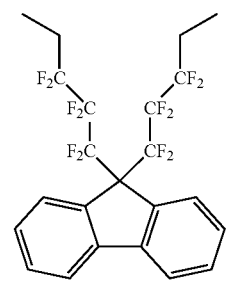

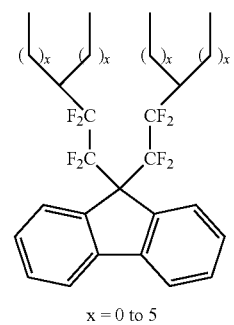

x = 0 to 5

Compounds of the Structure

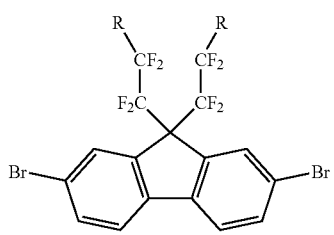

are preferred intermediates for the synthesis of compounds containing these fluoroalkyl fluorene derivative emitter cores due to their synthetic utility.

$Ar^1$ and $Ar^2$ $Ar^1$ and $Ar^2$ in each occurrence are independently selected from the group comprising $Ar^a$ and a bond. $Ar^a$ represents a diradical comprising 1 aromatic, heteroaromatic or FL moiety, or 2, 3, 4 or 5 aromatic, heteroaromatic and/or FL moieties mutually connected by single bonds. Diradicals are groups that are covalently bound to two other moieties within the overall structure of the compound, some typical examples are presented below, * denotes the typical site of attachment.

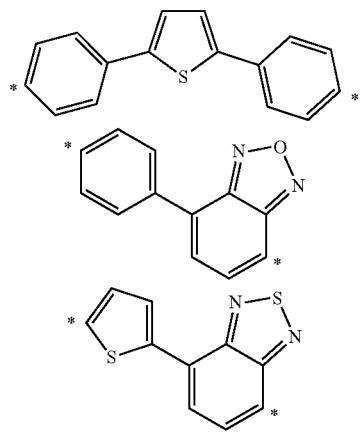

The precise nature of the $Ar^a$ groups selected is dependent on the properties desired in the system. For example, if a light emitting compound is required two, three, four, five or six contiguous FL groups may feature in the structure. Alternatively, a high proportion of $Ar^a$ groups, for example 50% or more, may be FL groups.

The constituent aromatic and heteroaromatic group comprised by $Ar^a$ can be selected from the group of $C_6$-$C_{16}$ aromatic group and $C_4$-$C_{12}$ heteroaromatics that are optionally substituted. The optional substituents may be selected from the group of $C_1$-$C_{10}$ alkyl or ether groups which are optionally achirally branched.

Aromatic diradicals that are useful as $Ar^a$ structural units in the materials of the invention include, but are not limited to, 1,4-phenylene, biphenyl-4,4'-diyl, terphenyl-4,4''-diyl, naphthalene-1,4-diyl, naphthalene-2,6-diyl, thiophene-2,5-diyl, pyrimidine-2,5-diyl, pyridine-2,5-diyl, perylene-3,10-diyl, pyrene-2,7-diyl, 2,2'-dithiophene-5,5'-diyl, oxazole-2,5-diyl, 1,3,4-oxadiazole-2,5-diyl, thieno[3,2-b]thiophene-2,5-diyl, dithieno[3,2-b:2',3'-d]thiophene-2,6-diyl, dibenzothiophene-3,7-diyl, benzo[1,2-b:4,5-b']bis[1]benzothiophene-3,9-diyl, thiazolo[5,4-d]thiazole-2,5-diyl, oxazolo[5,4-d]oxazole-2,5-diyl, thiazolo[5,4-d]oxazole-2,5-diyl, thiazolo[4,5-d]thiazole-2,5-diyl, oxazolo[4,5-d]oxazole-2,5-diyl, thiazolo[4,5-d]oxazole-2,5-diyl, 2,1,3-benzothiadiazole-4,7-diyl, 4-thien-2-yl-2,1,3-benzothiazole-7,5'-diyl, 4,7-dithien-2-yl-2,1,3-benzothiazole-5',5''-diyl, imidazo[4,5-d]imidazole-2,5-diyl, 4-alkyl-1,2,4-triazole-3,5-diyl, 4-aryl-1,2,4-triazole-3,5-diyl, 4-phenyl-1,2,4-triazole-3,5-diyl, 4-(p-tertbutylphenyl)-1,2,4-triazole-3,5-diyl, di-1,2,4-triazolo[4,5-f:4,5-q]-5,6,12,13-tetrahydro-5,12-diazadibenz[a,h]anthracene-5,13-diyl, 9-alkylcarbazole-2,7-diyl, 6,12-dialkylindolo[2,3-b]carbazole-2,8-diyl, benzo[1,2-b:4,5-b']dithiophene-2,6-diyl, benzo[1,2-b:5,4-bi]dithiophene-2,6-diyl, [1]benzothieno[3,2-b][1]benzothiophene-2,7-diyl, benzo[1,2-d:4,5-d']bisoxazole-2,6-diyl, benzo[1,2-d:5,4-d]bisoxazole-2,6-diyl, 5,5-dioxodibenzothiophene-3,7-diyl, or 6,12-dialkyl-5,5-11,11-tetraoxobenzo[1,2-b:4,5-b']bis[1]benzothiophene-3,9-diyl diradicals, If hole transporting properties are desired then indole and thiophene containing moieties such as those presented below may be preferred, * denotes the typical site of attachment.

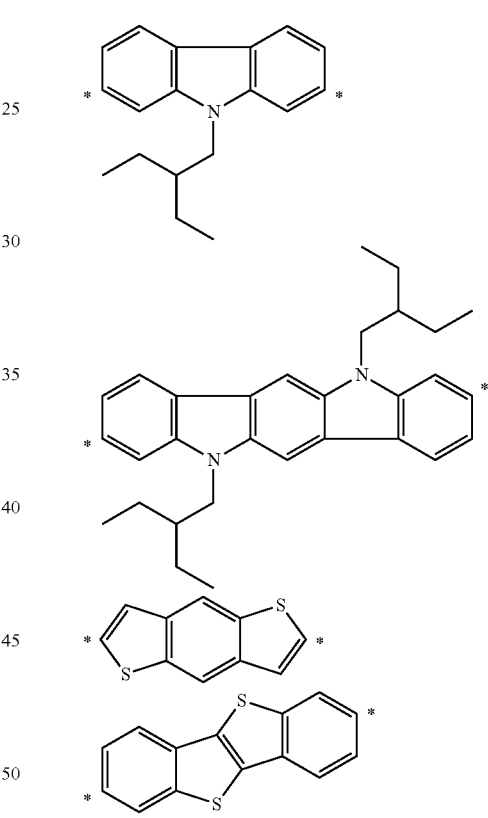

If electron transporting properties are desired then oxazole containing moieties such as those presented below may be preferred, * denotes the typical site of attachment.

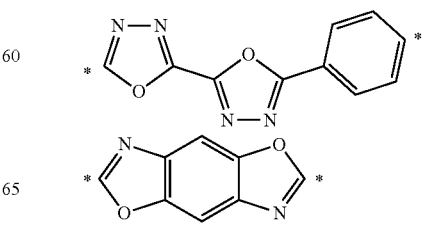

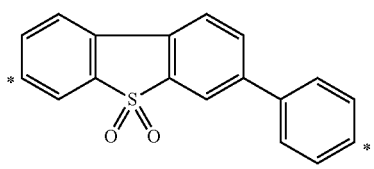

In a preferred aspect the compound is an emitter material and n is from 1 to 6. In a further preferred aspect n is 3 to 6. In a preferred aspect n is 5 or 6. In a preferred aspect n is 5. In a further preferred aspect n is 6. Longer molecules are preferred because device energy efficiency increases with increasing length of the aromatic core of the molecule. There is evidence from luminescence decay time measurements that the increase in energy efficiency is due to triplet-triplet exciton annihilation that occurs in the longer molecular cores, but is less likely to occur in shorter molecular cores. Further small increases in energy efficiency can be achieved by lengthening the molecular cores even further to n=7 or 8, but increases in efficiency has to be balanced with the increased cost of synthesising such molecules.

A further preferred aspect of the invention is that emitter materials of the invention comprise molecular core structures, A, are terminated with FL units. In charge transporting or host material molecules the termination of the molecular cores with Ar units such as biphenyl-4,4'-diyl can be advantageous because the liquid crystalline properties of the materials can be enhanced and charge carrier transport can be enhanced by strong intermolecular interactions mediated by π-π interactions between the terminal Ar groups. However, in the case of emitter materials, these same interactions can lead to quenching of the exciton energy and terminal FL groups with relative bulky substituents at the 9-positions are therefore preferred.

Flexible Linker Groups $S^1$, $S^{1a}$, $S^2$ and $S^{2a}$

When D represents a cross linkable group the compounds of the invention contain two flexible linker groups $S^1$ and $S^2$. As discussed herein, D can also represent a more complex structure containing additional flexible linker groups $S^{1a}$ and $S^{2a}$ that are analogous to the $S^1$ and $S^2$ groups. In each occurrence $S^1$, $S^{1a}$, $S^2$ and $S^{2a}$ are independently selected from straight chain or branched achiral $C_5$-$C_{14}$ alkyl groups, optionally wherein 1, 2, 3, 4 or 5 methylene groups are substituted for an oxygen atom, provided that R contains no peroxide, ketal or acetal groups, that is connected to A through either a bond or an ether, ester, carbonate, thioether, amine or amide linkage and that is connected through either a bond or an ether, ester, carbonate, thioether, amine or amide linkage to D, $B^1$, $B^2$, $B^3$ or $S^3$ as determined by the nature of D.

The flexible linker groups $S^1$, $S^{1a}$, $S^2$ and $S^{2a}$ serve to separate the fluorophore system within A from the cross linkable groups. When the material is cross linked into a network polymer matrix, the flexible linker mechanically and electronically isolates the fluorophore from the polymeric matrix. Thus when the material is cross linked into a polymer matrix, the flexible linker serves to reduce non-emissive exciton quenching thereby favouring efficient light emission.

D, $B^1$, $B^2$ and $B^3$

D represents a cross linkable group or, when $B^1$ represents a hydrogen, D represents —$B^2$—$S^3$—$B^3$—$S^{1a}$-A-$S^{2a}$—$B^{1a}$, —$S^3(B^2)$—$B^3$—$S^{1a}$-A-$S^{2a}$—$B^{1a}$, —$S^3(B^2)(B^3)$—$S^{1a}$-A-$S^{2a}$—$B^{1a}$—$S^3(B^2)(B^3)$ or a cross linkable group wherein the dash at the left-hand end of the chain represents the point of attachment to $S^1$. $B^1$, $B^2$ and $B^3$ each independently represent a cross linking group or a hydrogen.

The compounds of the invention therefore comprises cross linking group and form, when cross linked, network polymers. This is because preferred cross linking groups react with two other cross linking groups to yield a chain reaction and a polymer matrix.

In a preferred aspect, cross linking groups are selected from the group of ethylenic, diene, thiol and oxetane cross linkable groups. Ethylenic cross linkable groups are cross linkable groups containing a carbon-carbon double bond. In a preferred aspect, all of the cross linking groups independently represent an ethylenic cross linking group. Favoured ethylenic cross linking groups include electron rich and electron poor ethylenic cross linking groups.

In a preferred aspect the cross linkable groups undergo cross linking reaction on exposure to radiation. In a preferred aspect the cross linkable groups undergo cross linking reaction on exposure to ultra-violet (UV) light.

Examples of preferred cross linking groups are straight chain and cyclic α,β-unsaturated esters, α,β-unsaturated amides, vinyl ethers and non-conjugated diene cross linking groups. Favoured cross linking groups therefore include methacrylate, ethacrylate, ethylmaleato, ethylfumarato, N-maleimido, vinyloxy, alkylvinyloxy, vinylmaleato, vinylfumarato, N-(2-vinyloxymaleimido), 1,4-pentadien-3-yl and 1,4-cyclohexadienyl groups.

In a preferred aspect the cross linking groups are electron-rich ethylenic cross linkable groups. Electron rich ethylenic cross linkable groups contain an ethylene group substituted with one or more electron donating groups. The electron donating group can comprise a heteroatom such as O, N or S. In a preferred aspect the electron rich cross linkable group is a vinyloxy group. Other electron donating group substituted crosslinking groups are 1-alkenyl ethers such as propen-1-yloxy groups and buten-1-yloxy groups; cyclic vinyl ethers such as cyclohexen-1-yloxy and cyclopentene-1-yloxy; bicyclic vinyl ethers such as 2-norbornen-2-yloxy groups and groups in which the vinyl ether function is connected to the flexible linker or spacer ($S^1$, $S^{1a}$, $S^2$, $S^{1a}$ or $S^3$) through an intervening hydrocarbyl structure such as 4-vinyloxyphenyloxy and 2-vinyloxyethyl groups.

In a preferred aspect the cross linking groups are electron-poor ethylenic cross linkable groups. Electron deficient ethylenic cross linkable groups contain an ethylene group substituted with one or more electron withdrawing groups. The electron withdrawing group may comprise a carbonyl group and may for example be an ester or an amide. In a preferred aspect the electron deficient cross linkable group comprises a monoalkylmaleate group, a monoalkylfumarate group, a monoarylmaleate group, a monoarylfumarate group or a maleimide group. Other examples of electron deficient crosslinking groups are 4,4,4-trifluorocrotonate groups, Z-4,4,4-trifluorobutenoate groups, 3-trifluoromethyl-4,4,4-trifluorocrotonate groups, Z- and E-3-cyanoacrylates, Z- and E-3-cyanomethacrylates, monoalkyl cyclohexene-1,2-dicarboxylates, and monoalkyl cyclopentene-1,2-dicarboxylates.

As stated above, D represents a cross linkable group or, when $B^1$ represents a hydrogen, D can represent —$B^2$—$S^3$—$B^3$—$S^{1a}$-A-$S^{2a}$—$B^{1a}$, —$S^3(B^2)$—$B^3$—$S^{1a}$-A-$S^{2a}$—$B_{1a}$, —$S^3(B^2)(B^3)$—$S^{1a}$-A-$S^{2a}$—$B^{1a}$, or —$S^3(B^2)(B^3)$ or a crosslinking group wherein the dash at the left-hand end of the chain represents the point of attachment to $S^1$.

Thus, in one aspect, D is of the structure $—B^2—S^3—B^3—S^{1a}\text{-}A\text{-}S^{2a}—B^{1a}$ and all elements of D are connected in a linear chain. An example of this arrangement, wherein for the purposes of illustration the cross linkable groups $B^2$ and $B^3$ are monomethyl maleate groups and $B^1$ and $B^{1a}$ represent hydrogen, the overall structure is the "type 1" $S^3$ spacer presented below.

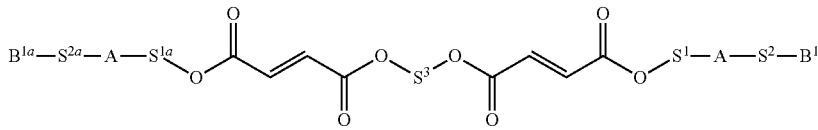

"Type 1" $S^3$ Spacer

In a second aspect, D is of the structure $—S^3(B^2)—B^3—S^{2a}—B^{1a}$ and one cross linkable group, $B^2$, forms a side chain branching from and attached to $S^3$. An example of this arrangement, wherein for the purposes of illustration the cross linkable groups $B^2$ and $B^3$ are monomethyl maleate groups and $B^1$ and $B^{1a}$ represent hydrogen, the overall structure is the "type 2" $S^3$ spacer presented below.

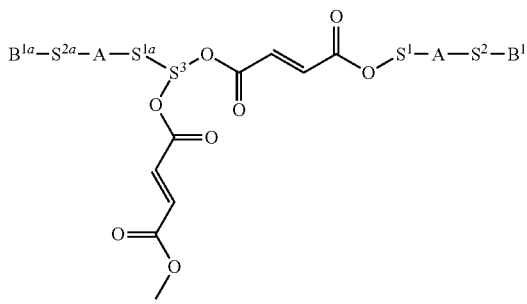

Type 2 $S^3$ Spacer

In a third aspect, D is of the structure $S^3(B^2)(B^3)—S^1\text{-}A\text{-}S^{2a}—B^{1a}$ both $S^1$ groups within the structure are bridged by the linker $S^3$ to which two cross linkable groups are attached and projects from. An example of this arrangement, wherein for the purposes of illustration the cross linkable groups $B^2$ and $B^3$ are monomethyl maleate groups and $B^{1a}$ and $B^1$ represent hydrogens, the overall structure is the "type 3" $S^3$ spacer presented below

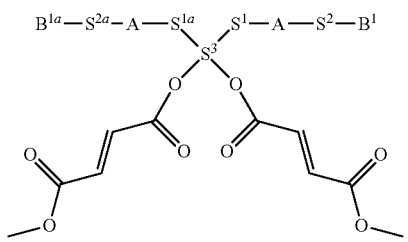

Type 3 $S^3$ Spacer

In a fourth aspect, D is of the structure $—S^3(B^2)(B^3)$. In this structure the spacer group $S^3$ is decorated with two cross linking groups. An example of this arrangement, wherein for the purposes of illustration the cross linkable groups $B^2$ and $B^3$ are monomethyl maleate groups and $B^1$ represents a hydrogen, the overall structure is the "type 4" $S^3$ spacer presented below.

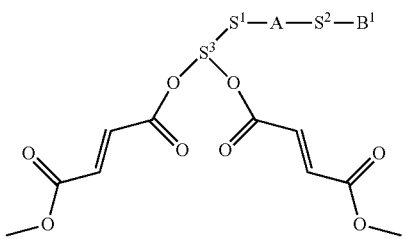

Type 4 $S^3$ Spacer $S^3$

D represents a cross linkable group or, when $B^1$ represents a hydrogen, D can represent $—B^2—S^3—B^3—S^{1a}\text{-}A\text{-}S^{2a}—B^{1a}$, $—S^3(B^2)—B^3—S^{1a}\text{-}A\text{-}S^{2a}—B^{1a}$, $—S^3(B^2)(B^3)—S^{1a}\text{-}A\text{-}S^{2a}—B^{1a}$, or $—S^3(B^2)(B^3)$ or a crosslinking group wherein the dash at the left-hand end of the chain represents the point of attachment to $S^1$ and where $B^{1a}$ represents a hydrogen. In this structure a further spacer $S^3$ is present.

$S^3$ represents a non-chromophoric spacer group that may be rigid or flexible. $S^3$ may comprise a $C_1$-$C_{20}$ alkyl group, $C_1$-$C_{20}$ haloalkyl group, a $C_3$-$C_8$ cycloalkyl group, a $C_6$-$C_{16}$ aryl group or a $C_4$-$C_{15}$ heteroaryl group or a chain consisting of 1, 2, 3, 4 or 5 $C_1$-$C_{20}$ alkyl, $C_1$-$C_{20}$ haloalkyl, $C_3$-$C_8$ cycloalkyl, $C_6$-$C_{16}$ aryl and/or $C_4$-$C_{15}$ heteroaryl moieties each independently connected by a bond, an ether linkage or an ester linkage. $S^3$ is connected to $B^2$ and/or $B^3$ through a bond, an ether, ester or carbonate linkage.

Preferred examples of the spacer $S^3$ comprise a $C_2$-$C_{12}$ alkyl group, a $C_3$-$C_8$ cycloalkyl group or a $C_6$-$C_{16}$ aryl group or a chain consisting of 1, 2, 3, 4 or 5 $C_1$-$C_{20}$ alkyl, $C_1$-$C_{20}$ haloalkyl, $C_3$-$C_8$ cycloalkyl, $C_6$-$C_{16}$ aryl and/or $C_4$-$C_{15}$ heteroaryl moieties each independently connected by a bond, an ether linkage or an ester linkage.

Examples of Type 1 $S^3$ spacer groups with $B^2$ and $B^3$ crosslinking groups presented for clarity are presented below (the wavy line indicates the point of attachment to $S^1$ and $S^{1a}$):

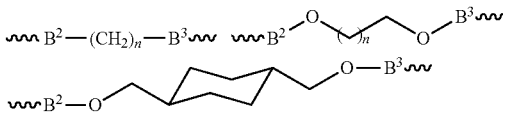

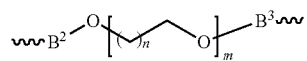
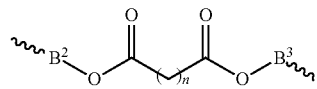
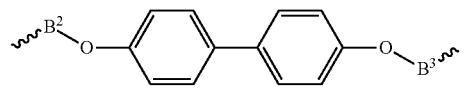
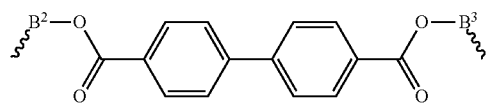
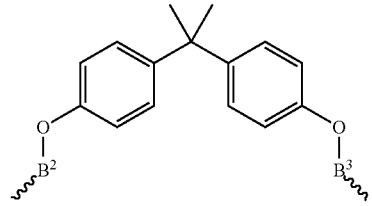
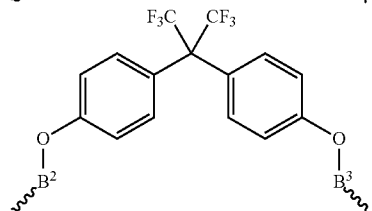
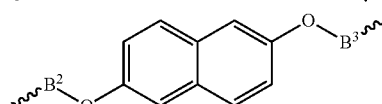
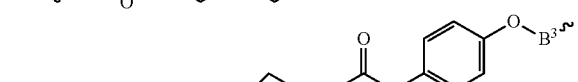
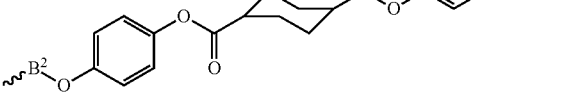
Examples of Type 2 $S^3$ spacer groups with $B^2$ and $B^3$ crosslinking groups presented for clarity are (the wavy line indicates the point of attachment to other chain components):
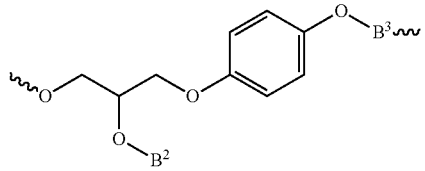
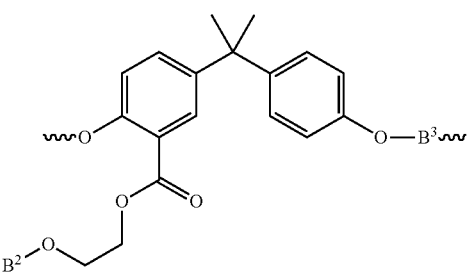
Examples of Type 3 $S^3$ spacer groups with $B^2$ and $B^3$ crosslinking groups presented for clarity are (the wavy line indicates the point of attachment to other chain components):
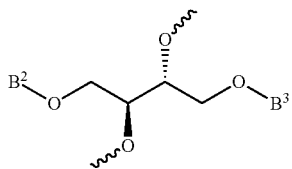
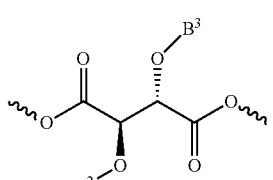
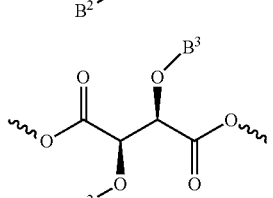
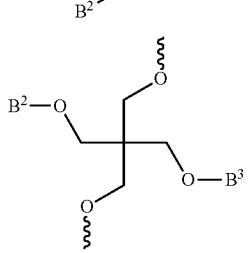
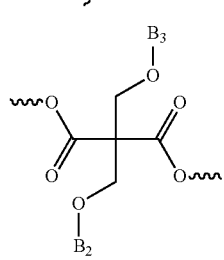

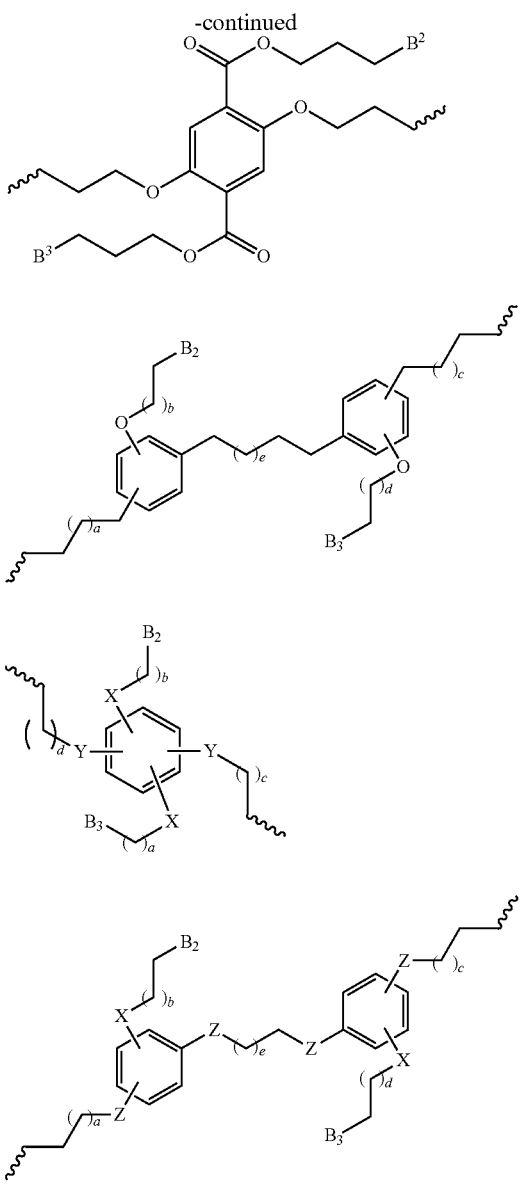

X, Y and Z are independently selected from bond, ether (O) or ester linkage (—CO₂)

a,b,c,d and e are integers that provide for a $C_1$ to $C_{20}$ linkage (alkyl, haloalkyl)

Type 3 $S^3$ spacer groups are of particular interest, as are the chemical intermediates for incorporating these groups into the overall $B_1$—$S^2$-A-$S^1$—$S^3(B^2)(B^3)$—$S^{1a}$-A-$S^{2a}$—$B^{1a}$ structure. Preferred examples of Type 3 $S^3$ spacer groups comprise a $C_2$-$C_{12}$ alkyl group, a $C_3$-$C_8$ cycloalkyl group or a $C_6$-$C_{16}$ aryl group or a chain consisting of 1, 2, 3, 4 or 5 $C_1$-$C_{20}$ alkyl, $C_1$-$C_{20}$ haloalkyl, $C_3$-$C_8$ cycloalkyl, $C_6$-$C_{16}$ aryl and/or $C_4$-$C_{15}$ heteroaryl moieties each independently connected by a bond, an ether linkage or an ester linkage. In a preferred example the Type 3 $S^3$ spacer group comprises a $C_2$-$C_{12}$ alkyl group, or a $C_6$-$C_{16}$ aryl group or a chain consisting of 1, 2, 3, 4 or 5 $C_2$-$C_{12}$ alkyl groups and/or $C_6$-$C_{16}$ aryl groups each independently connected by a bond, an ether linkage or an ester linkage. In a preferred example the Type 3 $S^3$ spacer group comprises 3, 4 or 5 $C_2$-$C_{12}$ alkyl groups and/or $C_6$-$C_{16}$ aryl groups each independently connected by a bond, an ether linkage or an ester linkage.

In a preferred example, the Type 3 $S^3$ spacer group comprises 5 groups selected from $C_2$-$C_{12}$ alkyl and $C_6$-$C_{16}$ aryl groups that are each independently connected by a bond, an ether linkage or an ester linkage. In Type 3 $S^3$ spacer groups it is preferred that the cross linking groups $B^2$ and $B^3$ are connected to $C_3$-$C_{12}$ alkyl groups, optionally $C_4$-$C_{10}$ alkyl groups, because this configuration provides greater structural flexibility and facilitates eventual cross linking reaction of $B^2$ and $B^3$ with the cross linking groups present in adjacent molecules. This affords the potential for cross linking under mild conditions and minimises and possible degradation.

In a preferred example, the Type 3 $S^3$ spacer group comprises four $C_2$-$C_{12}$ alkyl groups connected to a central $C_6$-$C_{16}$ aryl group by either a bond, an ether linkage or an ester linkage. In such Type 3 $S^3$ spacer groups the other end of each independent $C_2$-$C_{12}$ alkyl groups terminates in a connection to $B^2$, $B^3$, $S^1$ and $S^{1a}$, respectively. Examples of Type 3 $S^3$ spacer groups of this preferred variety are presented below wherein the wavy line indicates the point of attachment to other chain components, $S^1$ and $S^{1a}$, the groups X, Y and Z independently represent a bond, an ether linkage or an ester linkage, a and d is in each case an integer from 2 to 12 and a and c is in each case an integer from 1 to 11.

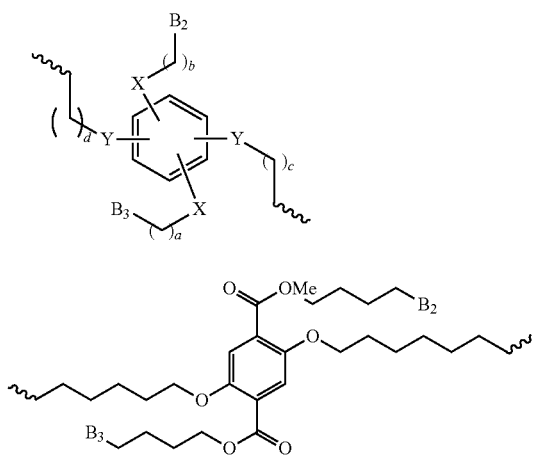

In a further preferred example, the Type 3 $S^3$ spacer group comprises three $C_2$-$C_{12}$ alkyl groups and two $C_6$-$C_{16}$ aryl groups connected to each other by either a bond, an ether linkage or an ester linkage. In such structures the each $C_6$-$C_{16}$ aryl groups is connected i) to the second $C_6$-$C_{16}$ aryl group by a $C_2$-$C_{12}$ alkyl group, ii) to a cross linker $B^2$ or $B^3$ by a $C_2$-$C_{12}$ alkyl group and iii) directly to $S^1$ and $S^{1a}$. Examples of Type 3 $S^3$ spacer groups of this preferred variety are presented below wherein the wavy line indicates the point of attachment to other chain components, $S^1$ and $S^{1a}$, the groups X, Y and Z independently represent a bond, an ether linkage or an ester linkage, b and d is an integer from 1 to 11 and a and c is an integer from 0 to 10.

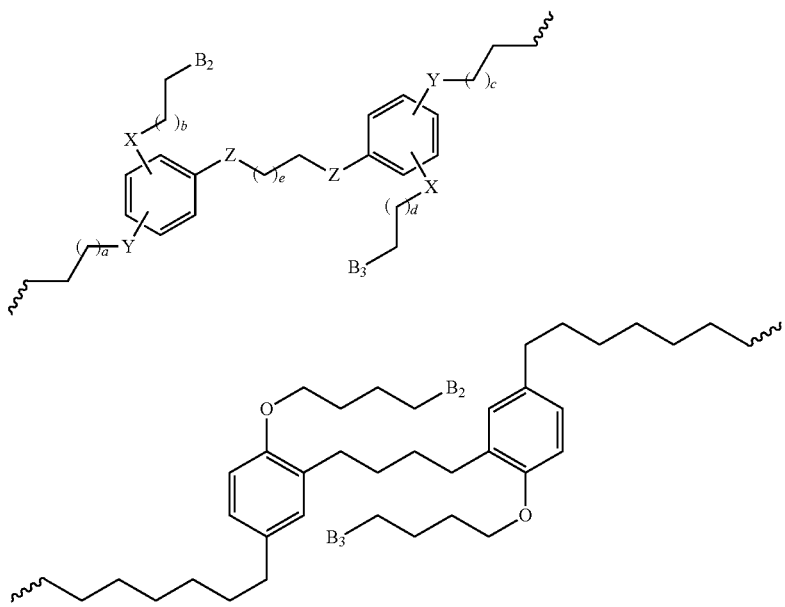
Examples of structures incorporating preferred Type 3 $S^3$ spacer group are presented below.
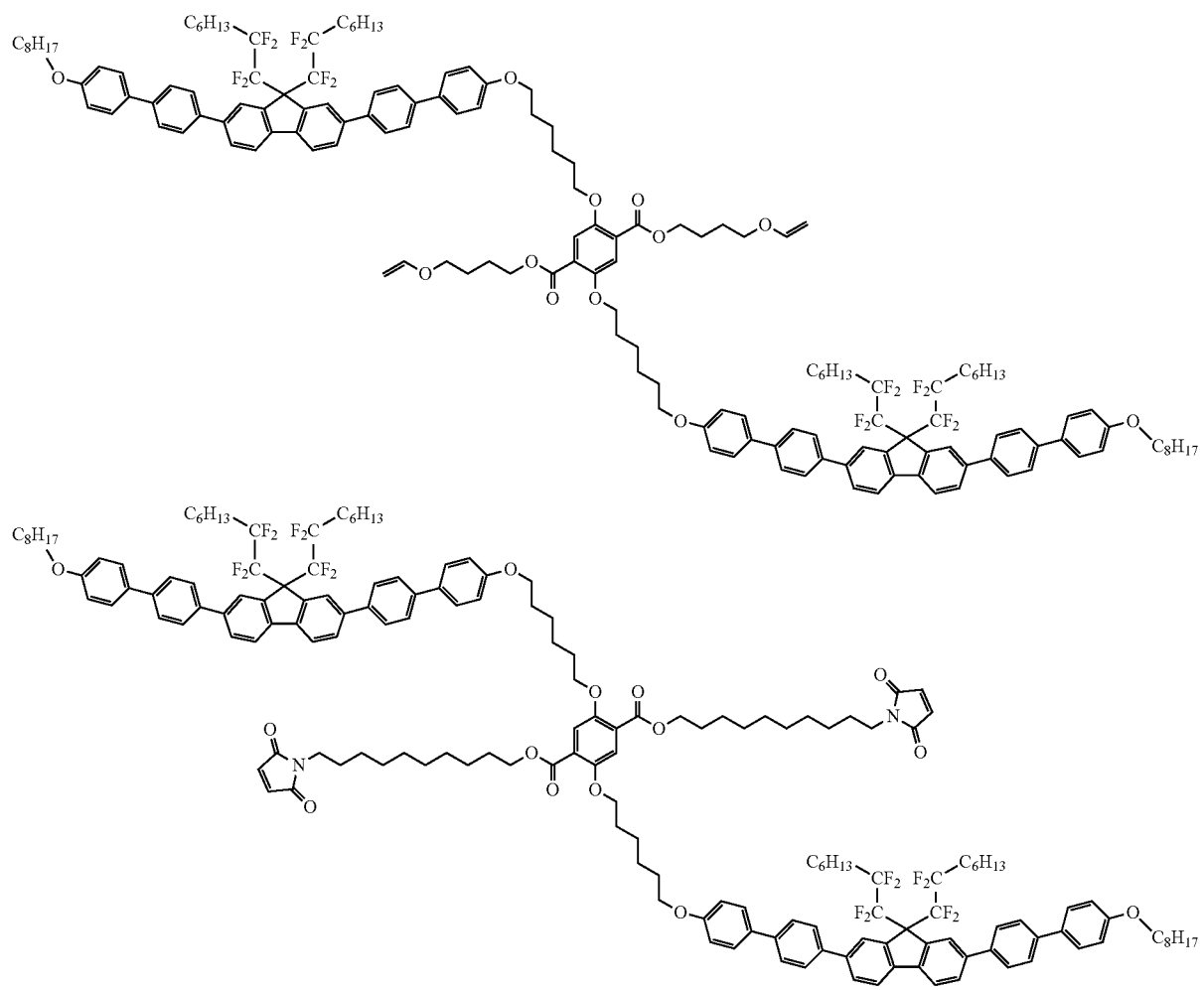

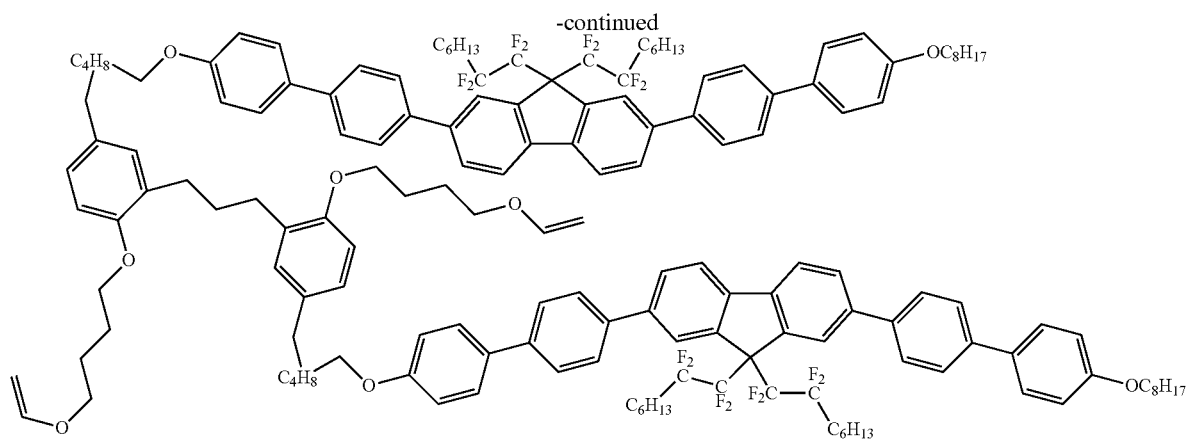

Examples of Type 4 $S^3$ spacer groups with $B^2$ and $B^3$ crosslinking groups presented for clarity are (the wavy line indicates the point of attachment to $S^1$):

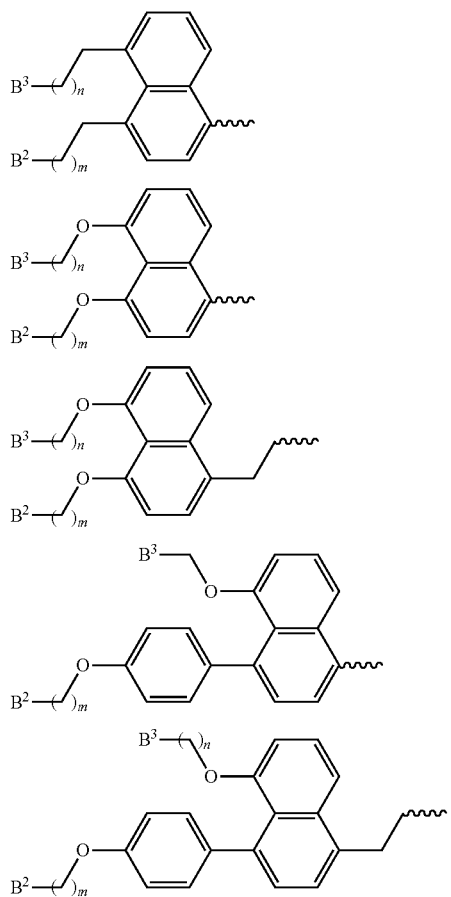

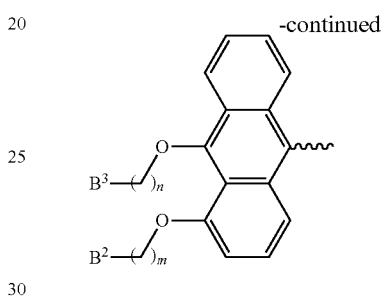

The group D in some instances can therefore be appreciated to be of the general structural types presented below.

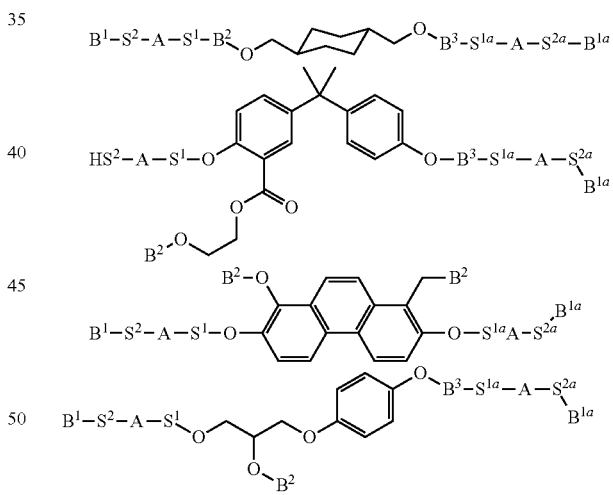

wherein $B^1$ and $B^{1a}$ represent hydrogens.

Further examples of structures D of the materials of the invention are provided below for illustration. Branching in the R group can be used to modulate the melting point of the material.

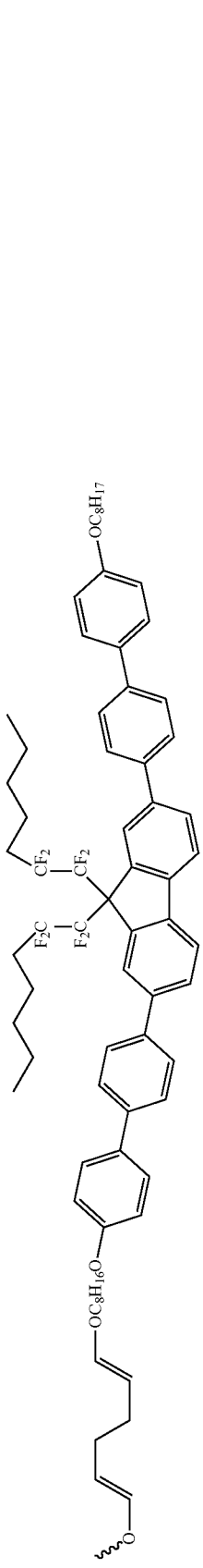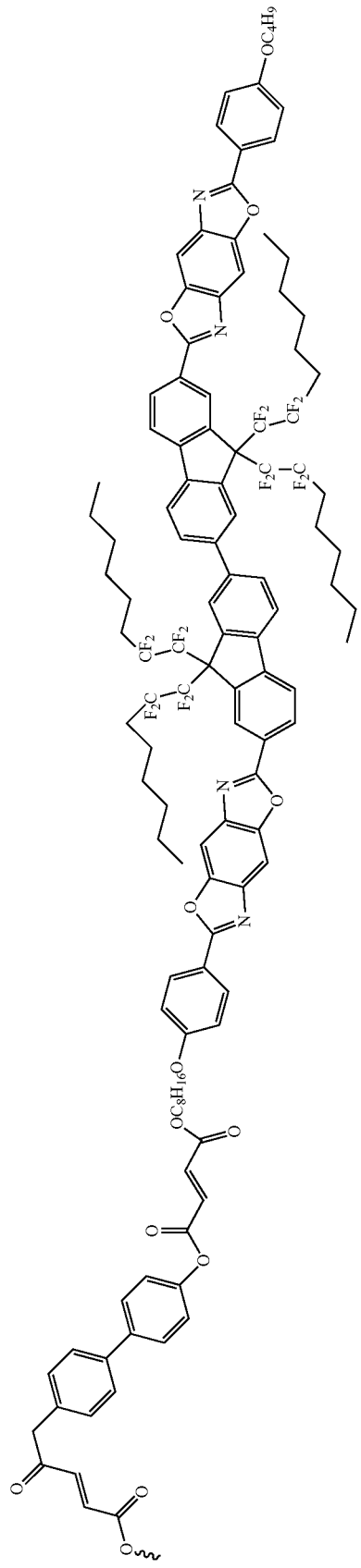

-continued
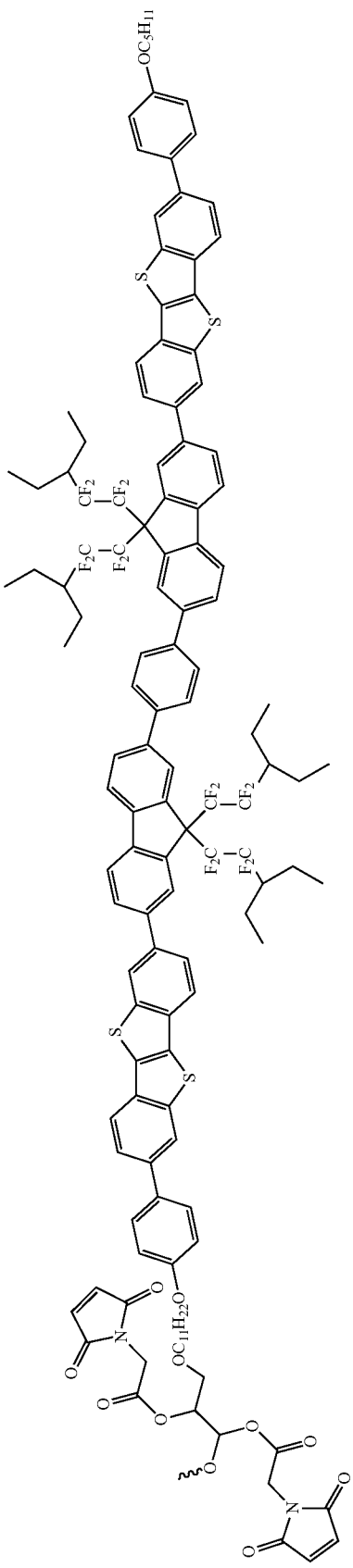
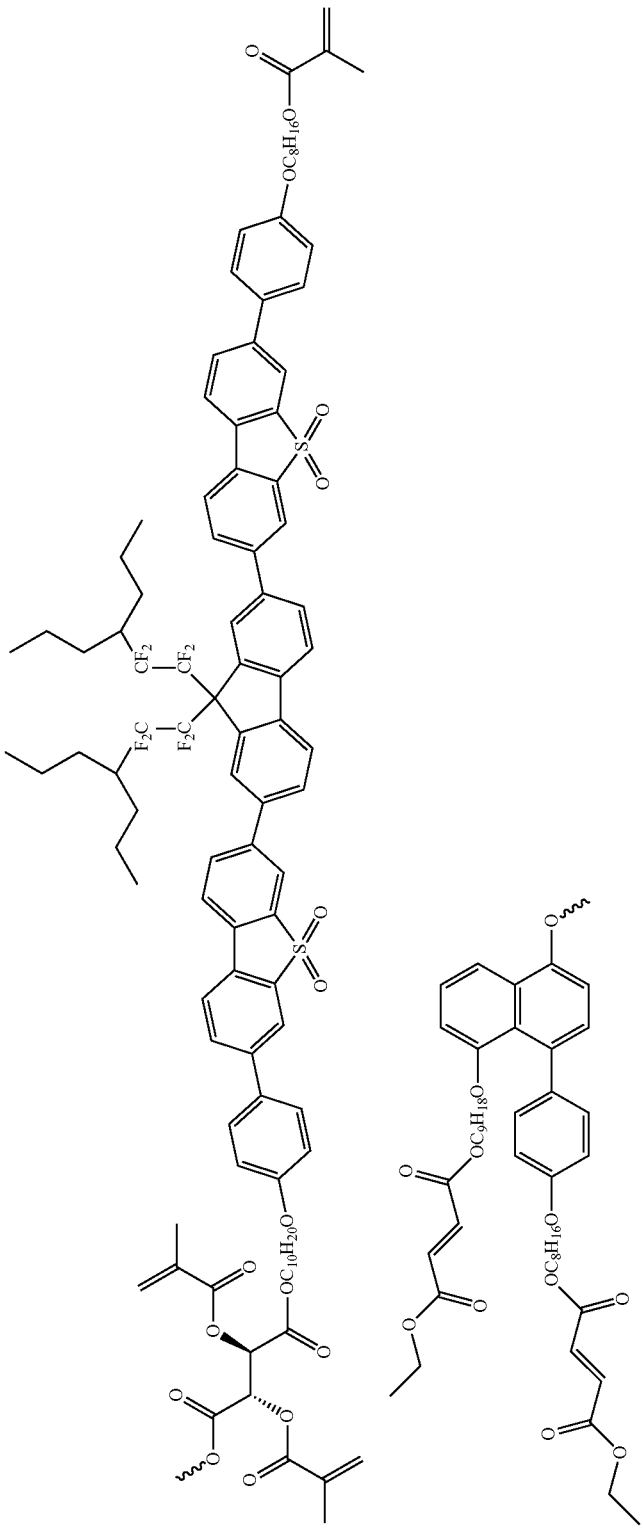

Material Properties

The materials of the present invention are particularly useful for both their charge transport and light emitting properties. As such the materials described herein are useful in the fabrication of electronic devices, for example organic light emitting diodes and photovoltaic devices.

One advantageous property of the oligomeric materials of the present invention is that they are soluble in common organic solvents. This is significant as the solubility properties of the oligomers provides a distinct advantage in terms of device fabrication relative to e.g. polymeric materials. In more detail, these oligomeric material may be used to fabricate devices via a solution processing approach. In outline, this involves first dissolving the material, applying this solution to a substrate and then evaporating to generate a film coating on the substrate. Once the material is deposited as a film the material can be polymerised in situ. This polymerisation may be initiated by exposure to radiation, for instance ultraviolet light, which causes the cross linkable groups of one molecule to cross link with those in an adjacent molecule to form a network polymer. Regions of the deposited film can be masked from the initiating radiation to give zones of non cross-linked material while zones exposed to radiation undergo polymerisation. If desired the unexposed, non-cross linked material can be washed off to leave behind a patterned structure of cross linked material due to the cross linked material having negligible or reduced solubility relative to that of the monomer. Iterative cycles of solution deposition and polymerisation can be used to generate structures with complex architectures.

Sequentially deposited polymerised structures can be assembled in a side by side or stacked/layered manner. In one example, sequential deposition and polymerisation of red, green and blue emitting material in a side by side manner can be used to generate pixels for colour displays. In another example, a stack of red, green and blue emitter materials can be used to give a white light source. In another example, two or more emitter structures can be arranged in a stack to give a coloured light source.

The ability to cheaply and economically produce multi-layer devices in which adjoining layers have different highest occupied or lowest unoccupied molecular orbital (HOMO and LUMO) energy levels as well as different charge carrier mobilities is of general utility in plastic electronics. For instance, the equivalent of p-n junctions may be formed using the materials and processes of this invention and these may find utility in diodes, transistors, and photovoltaic devices. The propensity of the materials of the invention to be photo lithographically patterned allows large arrays of plastic electronic devices of virtually any size and description to be fabricated.

Materials according to this invention may be mixed together to form liquid crystalline mixtures. This can be very advantageous from the standpoint of optimising the material properties for the intended application. For instance, individual compounds of the invention may have liquid crystal to isotropic liquid transition temperature far below their melting points (monotropic liquid crystalline phases). In device fabrication applications this can lead to glassy or supercooled liquid films of the materials that are sufficiently thermodynamically unstable so as to lead to the danger of crystallisation within the film and subsequent destruction of useful electronic properties. Mixing multiple component compounds together can depress the melting point of the resulting mixtures below the liquid crystal to isotropic liquid transition temperatures or at least sufficiently suppress crystallisation so as to eliminate this problem.

Another advantage associated with using mixtures of the materials of the invention is that it may allow materials with otherwise highly useful device application properties to be used even though they a have a particular property that renders them unusable as a pure material. For instance it may be desired to prepare a light emitting polymer film having a nematic liquid crystalline structure. A compound of the invention may be a light emitting material of very high efficiency and possess other useful properties, but at the same time may be found to possess a smectic rather than a nematic liquid crystalline phase. By dissolving said desirable compound into a mixture of other compounds of the invention that have nematic phases, a mixture having the light emission properties of the first highly desirable material combined with a nematic phase structure may result.

A further advantage associated with using liquid crystalline materials or mixtures of material is that directional organised or anisotropic structures can be formed. This directional order can be fixed in place by cross linking the components of the deposited films, for example by exposing the deposited film to radiation such as ultraviolet light.

In one preferred instance, a liquid crystalline film can be deposited onto a substrate that is coated with an alignment layer such as a photoalignment layer. The components of a photoalignment layer form directionally ordered structures on exposure to light. This directional order in the alignment layer can then transfer into the deposited liquid crystalline film formed on its surface leading to a highly ordered device structure which can be locked in place by polymerising the component oligomer by exposing the deposited ordered film to radiation such as ultraviolet light.

The potential to obtain highly ordered device structures can be exploited to generate polarised light emitting structures in which the emitter cores are aligned in the same direction and therefore emit light in the same direction. Ultimately, the properties of the materials described herein afford the possibility to fabricate 3D-displays through sequential deposition of aligned layers of uniformly aligned liquid crystalline fluid or glass, sequential polymerisation of patterned areas of each layer in turn, and sequentially washing away unpolymerised areas of each layer in turn so as to provide light emitting structures such that the liquid crystalline alignment and thus the polarisation axis of light emission of each respective layer is in a different direction.

The materials of the present invention also possess a number of additional desirable properties that render them useful for the production of electronic devices such as OLEDs. In organic light emitting devices it is often also desirable to reduce the self-absorption of emitted light by organic luminescent materials. This self-absorption occurs because the spectral absorbance and emission bands of organic luminescent materials overlap to a greater or lesser extent in various materials. A solution to this problem well known, for instance, in the field of dye lasers is to dissolve the luminescent material in a host with that absorbs light at a shorter wavelength than the luminescent solute. If the solution is dilute, for instance one to two percent, the self-absorption of the luminescent solute is nearly completely suppressed. The facile mutual miscibility of the various compounds of this invention makes the preparation of solutions of this type very easy. The materials of the present invention therefore are useful as host materials as well as light emitting materials.

In organic light emitting device applications it is necessary that there be facile excitation energy transfer from the host material to the solute luminescent material. This is because charge carriers (electrons and holes) must be transported through the host medium to recombine to form the excitons (electrically excited molecular orbital states) that radiate light. In a mixture composed mainly of component host molecules this recombination and exciton formation will mainly occur in the host molecules. The excitation energy then needs to be transferred from the host molecules into the luminescent solute molecules. It is a requirement for this energy transfer that the spectral luminescent emission band(s) of the host material overlap the absorption band of the luminescent solute. Thus an important aspect of the invention is the preparation of mixtures of the compounds of the invention that have this spectral relationship between the constituent components. For instance, a compound which emits in the blue region of the spectrum can serve as a host for a compound which is a green light emitter. A polymer film prepared by the UV induced crosslinking of a solution of 5% blue emitter compound in green emitter compound will exhibit considerably less self-absorption of the green light emitted by the green emitter than will a film prepared by UV crosslinking of pure green emitter.

To demonstrate the utility of the material of the invention exemplary blue and green emitters ("Lomox Blue" and "Lomox Green" as presented below) were incorporated into simple unoptimised OLED devices without crosslinking. In these devices the emissive layer consists of one of the selected fluoroalkyl fluorene based emitters doped into poly (vinyl carbazole) (PVK), a standard host material. The overall structure of the devices was ITO (125 nm)/PEDOT:PSS (50 nm)/PVK:Emitter (70 nm)/TPBI (30 nm)/LiF (1 nm)/Al (100 nm). PEDOT:PSS is a standard hole injection material, and TPBI is a standard electron transport material. Indium Tin Oxide (ITO) was used as the anode, while the cathode consists of lithium fluoride and aluminium. PEDOT:PSS and emissive layers were deposited on a pre-patterned glass/ITO substrate by spin coating, while the TPBI electron transport layer and cathode layers were subsequently deposited by thermal evaporation.

Figure 2:
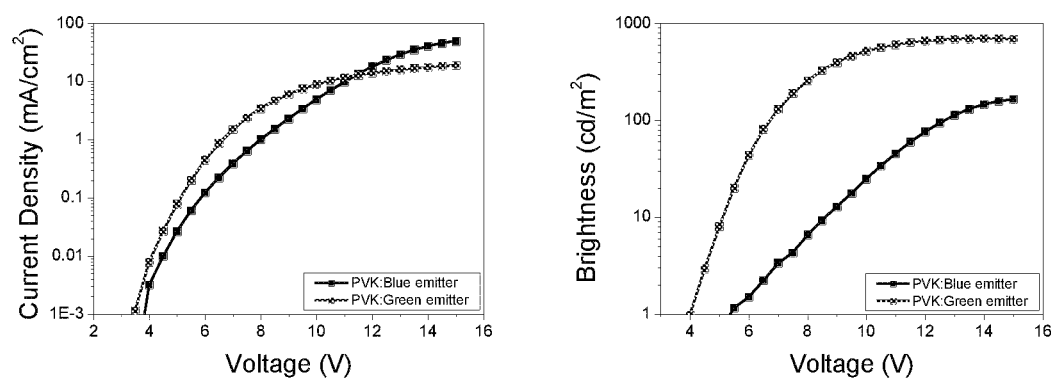
FIG. 2 is a graph of luminance data.

Current voltage and luminance data for these devices are shown in FIG. 2 which shows in the first graph: J-V (left) and in the second L-V (right) data of devices incorporating the emitters of the present invention as dopants in a PVK host.

For a device of the present invention with a blue emitter shown here, the doping ratio was 100:5 PVK:Emitter, while for the green device the ratio was 100:15. Devices incorporating the blue emitter reached a peak luminance of 165 cd m$^{-2}$ at a voltage of 15 V, while for the green emitter the peak luminance was 700 cd m$^{-2}$ at a voltage of 14 V.

Additionally, devices using the blue emitter as a host material for the green emitter have been fabricated, demonstrating that this material can be used as a host as well. This device incorporated a layer of PVK as a hole transport/electron blocking interlayer, for an overall device structure of ITO (125 nm)/PEDOT:PSS (50 nm)/PVK (30 nm)/Lomox Blue:Lomox Green (50 nm)/TPBI (30 nm)/LiF (1 nm)/Al (100 nm). The ratio of Lomox blue host to Lomox green emitter in the device shown was 85:15.

Figure 3:
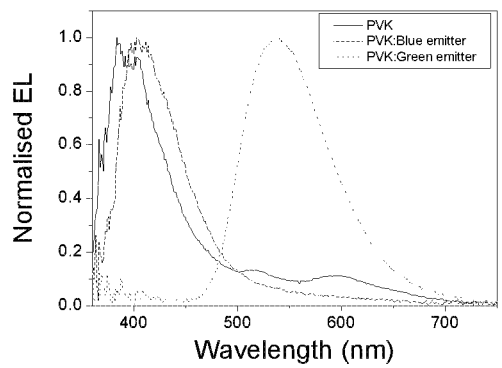
FIG. 3 is an electroluminescence spectra graph.

Current voltage and luminance data for this device are shown in FIG. 3. The peak luminance attained for this device was 595 cd m$^{-2}$ at a voltage of 14.5 V.

Figure 4:
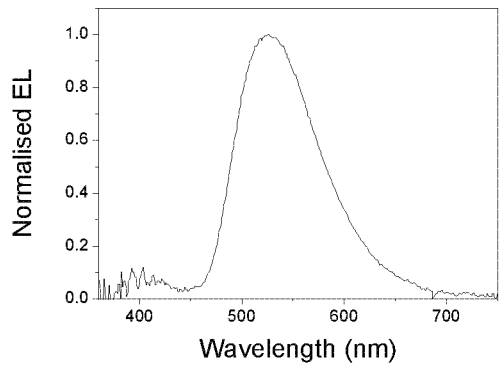
FIG. 4 is an electroluminescence spectra graph.

The electroluminescence spectrum of this device is shown in FIG. 4, showing predominantly green emission from the dopant emitter while a weaker peak of blue emission from the host material can be seen between 350 and 450 nm.

Yet another advantage of using mixtures of the materials of the invention is that it allows the use of mixtures of reactive mesogen materials in which photoinitiated electron donor/acceptor interactions as opposed to ionic or free radical initiation are used to initiate polymerization. This may result in much more stable (in terms of shelf-life) reactive mesogen materials than in methacrylate-based systems, while at the same time maintaining low UV crosslinking fluences. In these mixtures at least one of the reactive mesogen materials is substituted with electron-rich crosslinking groups while at least one other component reactive mesogen material is substituted with electron-deficient

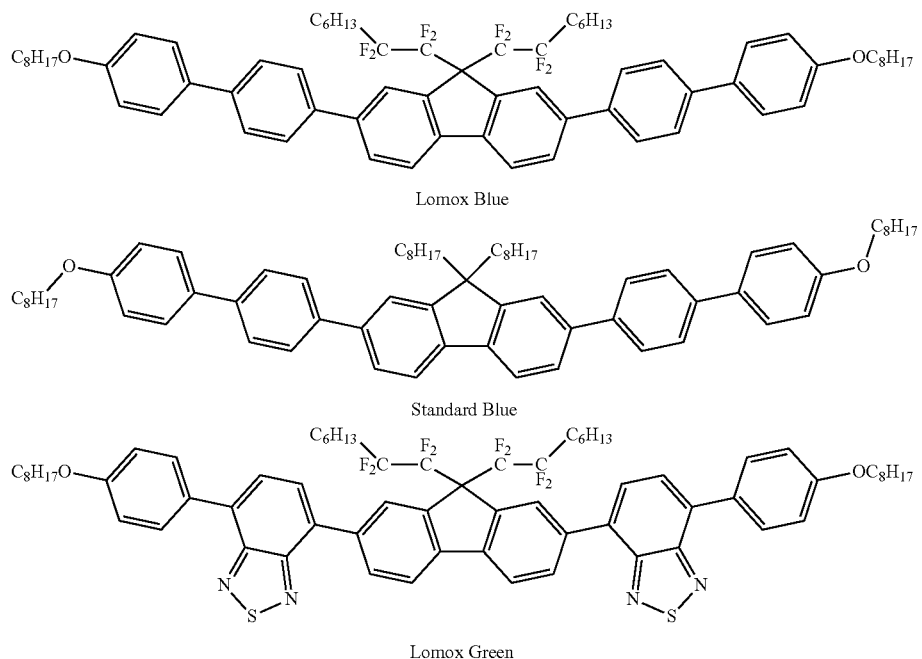

Lomox Blue

Standard Blue

Lomox Green crosslinking groups. Ultraviolet radiation incident on the material promotes the electron deficient crosslinking groups on some reactive mesogen molecules into electronically excited states. The excited state, electron-deficient crosslinking groups then abstract electrons from the electron-rich (electron donor) crosslinking groups on other reactive mesogen molecules initiating the copolymerization crosslinking reaction. Descriptions of this mode of photopolymerization may be found in, for example, "Photoinitiated radical polymerization of vinyl ether-maleate systems", Polymer 38, (9) pp. 2229-37 (1997); and "Co-Polymerization of Maleimides and Vinyl Ethers: A Structural Study", Macromolecules 1998, (31) pp. 5681-89.

Electron-deficient crosslinking groups include maleimides, maleates, fumarates, and other unsaturated esters. Electron donor groups include vinyl ethers, propenyl ethers and other similar alkenyl ethers. Mixtures like these are advantageous in that the individual components are thermally and photochemically stable with excellent shelf lives. However, when the materials are combined, the mixture has high photochemical sensitivity and requires only a relatively small UV dose for crosslinking.

Crosslinkable materials according to the present invention have been used as the emissive layer in OLED devices. Measurements of the devices demonstrate that the light emitted originates from the crosslinked Lomox layer.

The structure of the devices was ITO (150 nm)/PEDOT: PSS (50 nm)/PVK (30 nm)/Lomox emitter materials (65 nm unrinsed)/TPBI (30 nm)/LiF (1 nm)/Al (70 nm). Two devices (each of 4 pixels of area 4×4 mm) were fabricated with this architecture.

The emitter layer consisted of a blue host doped with a green emitter in the ratio blue:green 90:10. This final ratio was achieved with a mixture of (A, compound 43) blue fluorophore with maleimide crosslinker unit and (B, compound 41) blue fluorophore with vinyl ether crosslinker unit as the host material, doped with (C, compound 58) green fluorophore with vinyl ether crosslinkers blended in the ratio 50:40:10 A:B:C.

The solution processable PEDOT:PSS, PVK and emitter layers were deposited on a pre-patterned glass/ITO substrate by spin coating. Spin coating the Lomox emitter materials from 20 mg/ml toluene solution at 2500 rpm for 60 seconds results in good quality uniform films with a thickness of 65 nm.

After spin coating, the emitter layer was exposed to a metal halide lamp with broad emission from 280-450 nm (Dymax BlueWave 200) at a power density of 5 W/cm2 for 15 seconds in an argon atmosphere to crosslink the material. This broad spectrum light source covers the 350-380 nm range of excitation wavelengths at which the crosslinking process was found to be fastest for the Lomox materials used in these devices. After crosslinking, one device was spin rinsed with toluene in order to remove any uncrosslinked material, and one device was left unrinsed for comparison. The TPBI electron transport layer and cathode layers were subsequently deposited by thermal evaporation.

Figure 5:
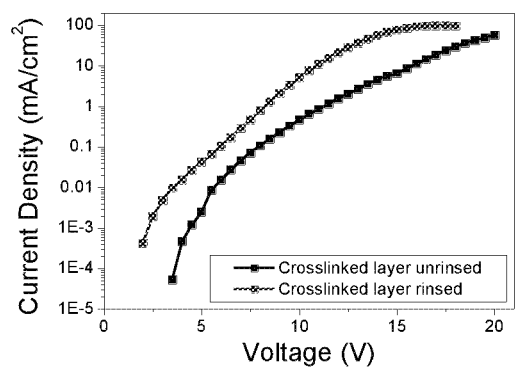
FIG. 5 depicts plots of current density vs voltage J-V (left) and L-V (right) data of devices with an emissive layer consisting of compounds of the present invention.
Figure 5:
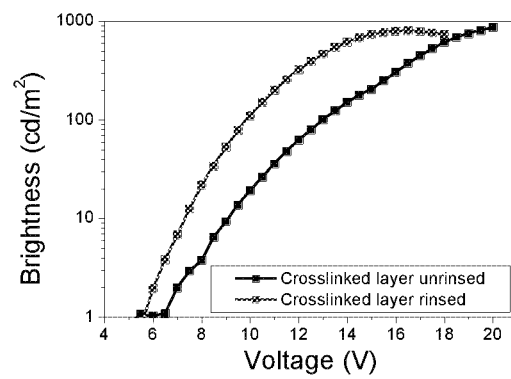

Current voltage and luminance data for these simple unoptimised devices are shown in FIG. 5. The device with a crosslinked and rinsed layer has a turn on voltage of 7.5 V, above which the device emits with a luminance in excess of 10 cd/m$^2$, and reaches a peak luminance of 804 cd/m$^2$ at 16.5 V. This demonstrates that crosslinking of these materials results in an insoluble, emissive film suitable for application in OLED devices. The current and brightness are higher for the rinsed devices as the rinsed layer is thinner.

Figure 6:
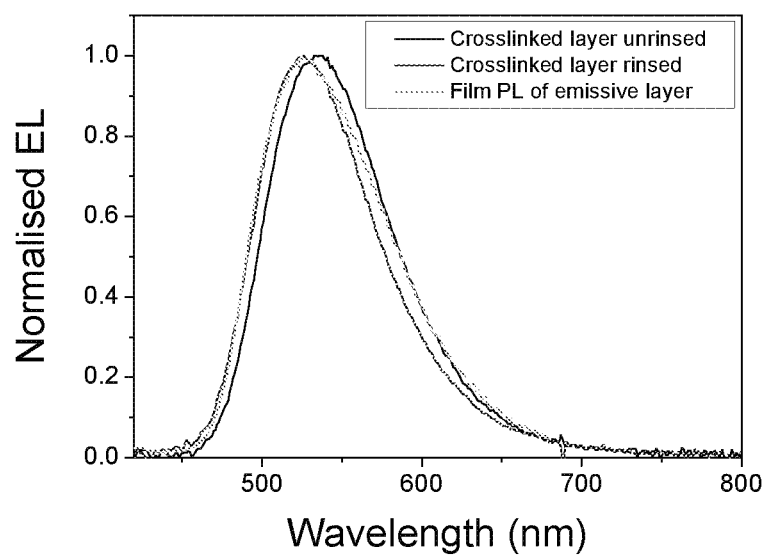
FIG. 6 is an electroluminescence spectra graph.

Electroluminescence spectra from these devices are shown in FIG. 6, along with the photoluminescence spectrum of the green material doped in the blue host in a crosslinked thin film. These spectra clearly show that the emission is green, and is therefore arising from the green Lomox emitter in the emissive layer. The spectral shift in emission on rinsing is likely to be an optical effect as the rinsed layer is thinner.

The stability of the 9,9'-(tetrafluoroalkyl) substituted fluorene emitter core relative to the corresponding 9,9'-alkyl fluorene core was evaluated by exposing a solution of each compound ("Lomox Blue" and "Standard Blue" as presented above) to irradiation with a 150 W xenon light source and measuring the reduction of fluorescence intensity over time. The results of this study (FIGS. 7 and 8) showed that the half life of the 9,9'-(tetrafluoroalkyl) substituted fluorene emitter was approximately 5 times longer than that of the corresponding 9,9'-alkyl fluorene. It is thus evident that the 9,9'-(tetrafluoroalkyl) substitution provides enhanced stability.

Further studies established that the absorption and emission properties of the 9,9'-(tetrafluoroalkyl) substituted fluorene emitter core and the corresponding 9,9'-alkyl fluorene core were similar and that the fluoro-alkyl chains at the fluorene 9-position do not have a detrimental effect on the fluorescence efficiency of the respective fluorophore in solution.

The fluorescence quantum yield ($\Phi_F$) is the ratio of photons absorbed to photons emitted through fluorescence. It reflects the probability of the excited state being deactivated by fluorescence rather than a non-radiative mechanism. In general, the higher the QF the better, as it results in a more efficient OLED device. It is thought that short fluorescence lifetimes may be more desirable for OLEDs due to the shorter time period that the molecule stays in the excited state and, thus, less chance of the molecule undergoing unwanted non-radiative decay and a decrease in fluorescence efficiency. The Lomox Blue compound proved to have a fluorescence lifetime in toluene solution of 15 ns which is significantly shorter than that observed for the Standard Blue that displayed a fluorescence lifetime in toluene solution of 75 ns suggesting the fluoroalkyl fluorene systems have further advantages in this respect.

TABLE 1

Comparison of the $\Phi_F$ in the solid-state of Standard Blue and Lomox Blue

| Compound | Excitation λ | Slit Width | $\Phi_F$ |
| --- | --- | --- | --- |
| Standard Blue | 350 nm | 2.5 | 0.84 |
| Lomox Blue | m | | 0.95 |

The compounds of the invention exhibit high $\Phi_F$ in solution and solid state (an integrating sphere was used for the solid-state $\Phi_F$ measurements) and also displayed efficient electrochemical stability and reversibility in DCM solution when studied by cyclic voltametry.

FIG. 1 demonstrates that compounds according to the invention can be liquid crystalline in nature. This polarising optical microscopy image of compound 23 at 110° C. shows Schlieren with thread-like textures and indicates that the molecule adopts a nematic mesophase.

FIG. 2 which shows in the first graph: J-V (left) and in the second L-V (right) data of devices incorporating the emitters of the present invention as dopants in a PVK host.

FIG. 3 shows a normalised electroluminescence spectra of devices incorporating the Lomox emitters as dopants in a PVK host. The spectrum of a plain PVK device is included for comparison.

FIG. 4 shows a normalised electroluminescence spectrum of device incorporating the Lomox green emitter as dopant and the Lomox blue emitter as host material.

FIG. 5 shows plots of current density vs voltage J-V (left) and L-V (right) data of devices with an emissive layer consisting of crosslinked materials according to the present invention.

FIG. 6 shows a normalised electroluminescence spectra of devices with an emissive layer consisting of crosslinked Lomox materials, as well as the photoluminescence spectrum of the Lomox green emitter doped in the Lomox blue host in a crosslinked thin film for comparison.

Figure 7:
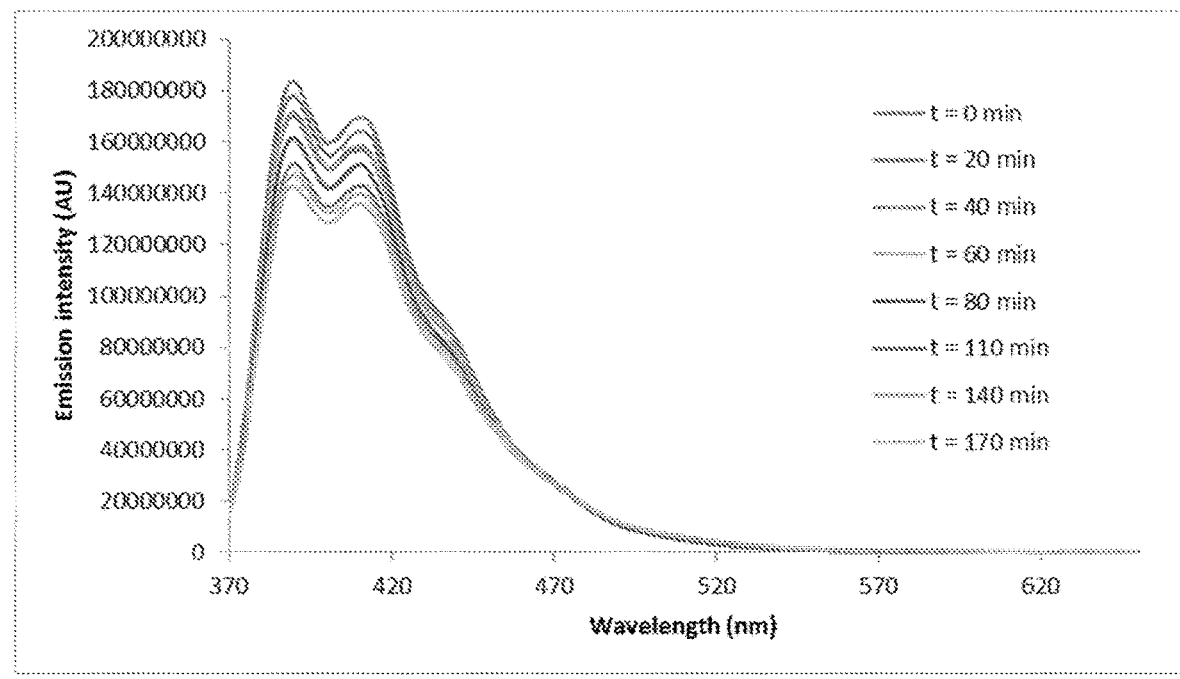
FIGS. 7 and 8 depict fluorescence spectra.
Figure 7:
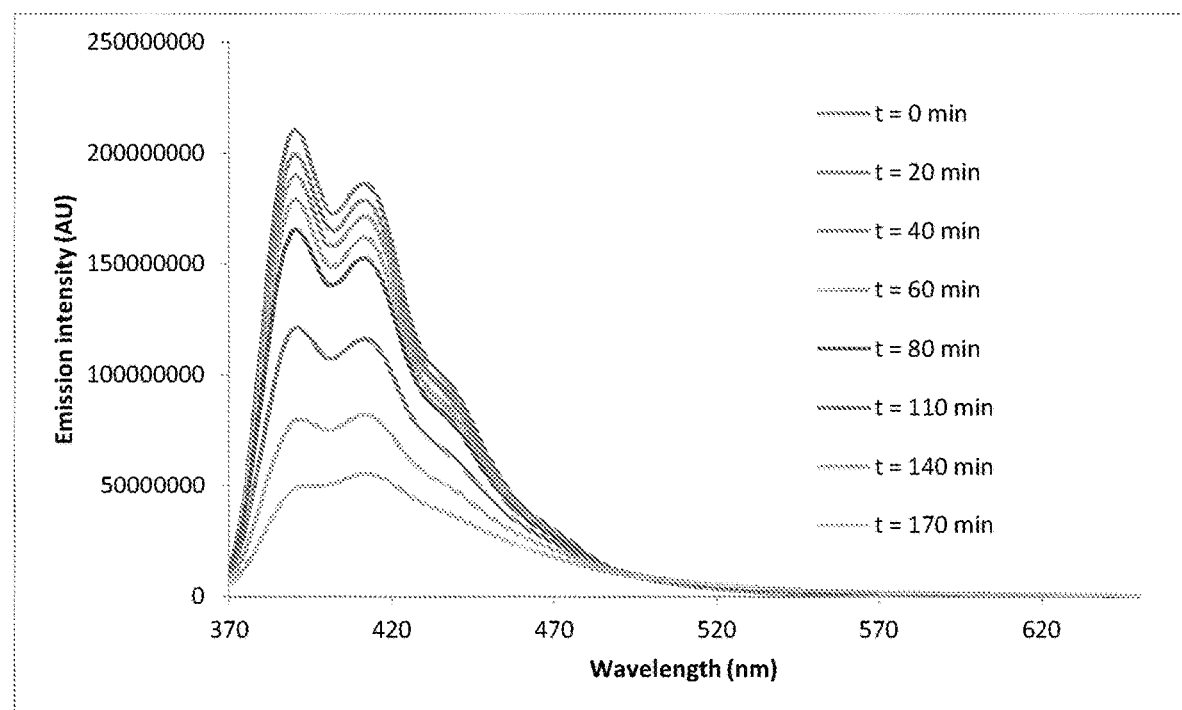

FIG. 7 shows fluorescence spectra for Lomox Blue/compound 1 (FIG. 7A) and Standard Blue/compound 2 (FIG. 7B) in toluene solution after varying lengths of exposure to light from a 150 W xenon light source.

Figure 8:
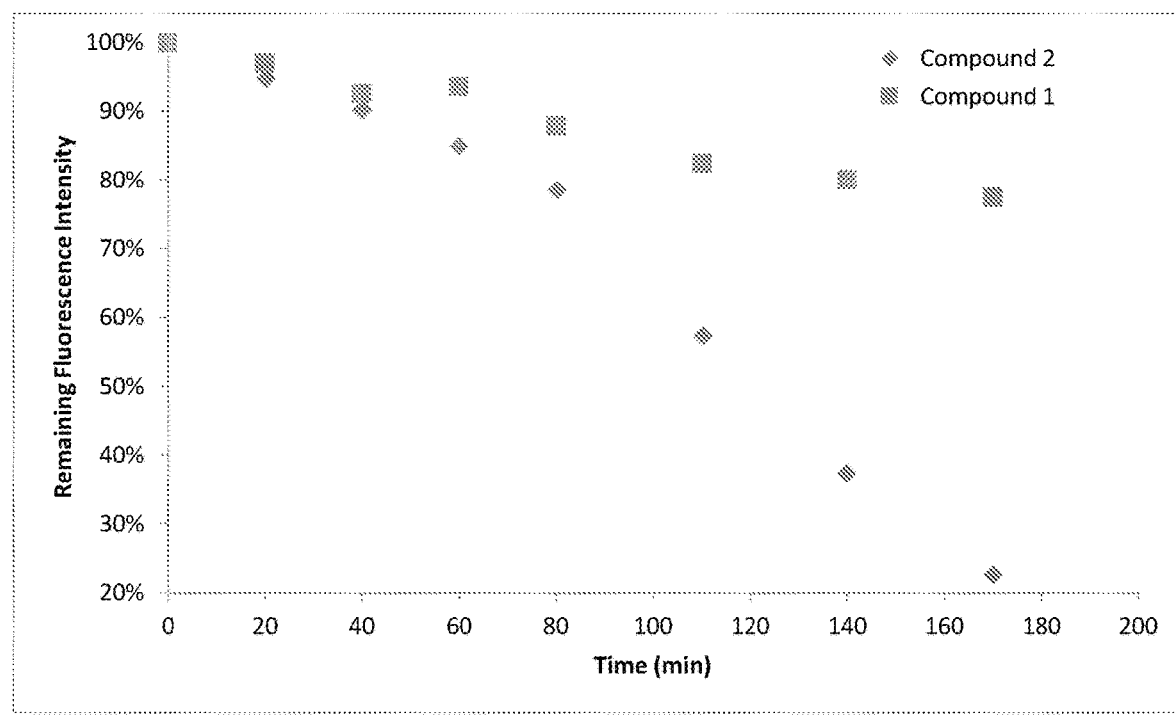

FIG. 8 shows remaining fluorescence intensity of the fluorescence peak at 391 nm for Lomox Blue/compound 1 (orange) and Standard Blue/compound 2 (blue) in toluene solution relative to time irradiated by a 150 W xenon light source.

Synthetic Examples

The compounds of the present invention may be synthesised by common techniques in organic synthesis well known to those of ordinary skill in the art. Illustrative examples of how these compounds can be synthesised are presented below. As can be appreciated, the nature of these materials allows a modular approach to synthesis to be adopted and the fluoroalkyl fluorene core can be integrated into a range of materials by standard chemical techniques. In this manner the nature of all components of materials, for example the core A, the various flexible linker/spacer groups ($S^1$, $S^{1a}$, $S^2$, $S^{2a}$ and $S^3$) and the various cross linkers and cross linker containing structures (D, $B^1$, $B^2$ and $B^3$) can be readily adjusted to fine tune properties of the bulk materials such as melting point, liquid crystallinity and light emissive properties. The examples provided below are by way of example only and in no way limit the scope of the invention.

Scheme 1 Synthesis of 9,9-difluoroalkylfluorene-2,7-biphenyl derivatives

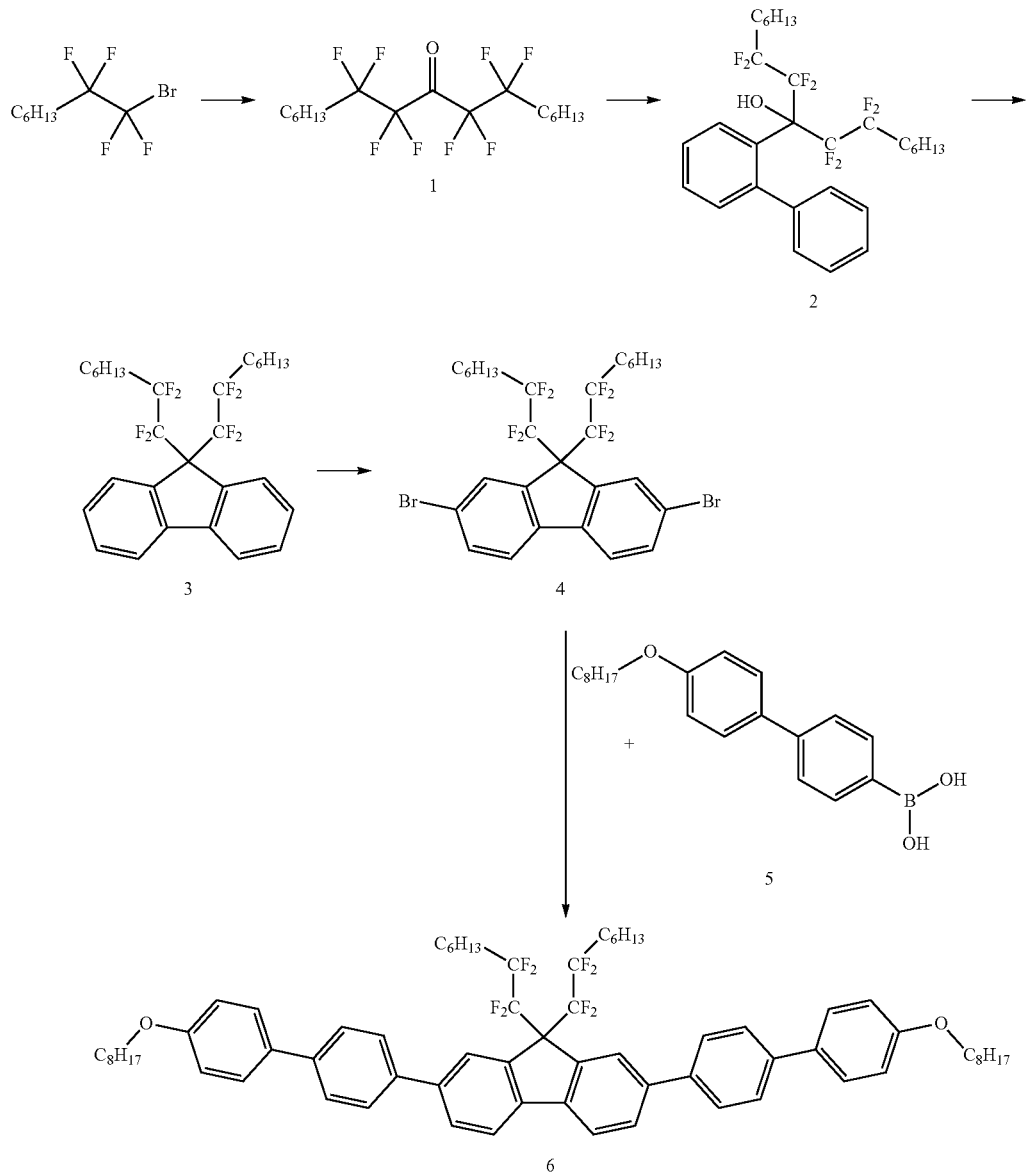

Octafluorinated Ketone 1

Methyllithium lithium bromide complex (6.6 mL, 9.9 mmol, 1.5 mM in diethyl ether) was added dropwise over 10 min to a stirred solution of diethyl carbonate (1.0 mL, 8.3 mmol) and 1-bromo-1,1,2,2-tetrafluorooctane (3.2 mL, 20.5 mmol) in dry diethyl ether (150 mL) under argon at −78° C. The reaction mixture was stirred at −78° C. for 10 min, after which another aliquot of methyllithium lithium bromide complex (6.6 mL, 9.9 mmol, 1.5 mM in diethyl ether) was added dropwise over 10 min at −78° C. The reaction mixture was left to stir at −78° C. for a further hour. The reaction was then quenched with concentrated HCl (6 mL) at −78° C. and the mixture was allowed to warm to room temperature. The solution was washed with 2 M HCl (100 mL) and the aqueous layer was extracted with diethyl ether (2×50 mL). The combined organics were dried (MgSO$_4$), filtered and the solvent was evaporated under reduced pressure. The crude product mixture was purified by vacuum distillation. The desired product 1 was obtained as a colourless oil (160° C., 1.3 mbar, 2.0 g, 5.0 mmol, 61%). $^1$H NMR (400 MHz, CDCl$_3$), δ=0.90 (6H, t, J=7 Hz, CH$_3$), 1.29-1.41 (12H, m, CH$_2$), 1.54-1.62 (4H, m, CH$_2$), 1.98-2.11 (4H, m, CH$_2$); $^{13}$C NMR (100 MHz, CDCl$_3$), δ=14.1 (CH$_3$), 20.3 (t, J=3.3 Hz, CH$_2$), 22.6 (CH$_2$), 29.0 (CH$_2$), 30.6 (t, J=22.3 Hz, CH$_2$), 31.5 (CH$_2$), 110.6 (t, J=38.5 Hz, CF$_2$), 113.3 (t, J=38.5 Hz, CF$_2$), 184.5 (m, C=O); $^{19}$F NMR (376 MHz, CDCl$_3$), δ=−118.3 (CF$_2$), −113.2 (CF$_2$).

Octafluorinated Tertiary Alcohol 2 n-BuLi (520 μL, 1.30 mmol, 2.5 M in hexanes) was added dropwise over 30 min to a stirred solution of 2-iodobiphenyl (0.18 mL, 1.00 mmol) in dry hexane (10 mL) under argon at −78° C. The mixture was stirred at −78° C. for 30 min and then allowed to warm to room temperature. The mixture was then stirred at room temperature for 30 min before being cooled to −78° C. The octafluoronated ketone (0.50 g, 1.26 mmol) was dissolved in dry hexane (10 mL) and then added to the reaction mixture at −78° C. The reaction mixture was allowed to warm to room temperature and stirred for 16 h. In the morning the reaction mixture was quenched with 5% HCl (30 mL), the layers were separated and the aqueous layer was extracted with diethyl ether (2×30 mL). The combined organics were washed with 5% HCl (30 mL) and water (30 mL). They were then dried (MgSO$_4$), filtered and the solvent was evaporated under reduced pressure. The crude product was purified by flash chromatography (hexane to 5% EtOAc in hexane), which yielded the product 2 as a colourless oil (0.48 g, 0.87 mmol, 87%). $^1$H NMR (400 MHz, CDCl$_3$), δ=0.90 (6H, t, J=7 Hz, CH$_3$), 1.26-1.33 (12H, m, CH$_2$), 1.43-1.51 (4H, m, CH$_2$), 1.90-2.03 (4H, m, CH$_2$), 3.20 (1H, s, OH), 7.09-7.12 (1H, m, Ar—H), 7.33-7.36 (2H, m, Ar—H), 7.39-7.42 (5H, m, Ar—H), 7.80 (1H, br s, Ar—H); $^{19}$F NMR (376 MHz, CDCl$_3$), δ=−114.9 (2F, d, J=286 Hz, CF$_2$), −113.8 (2F, d, J=284 Hz, CF$_2$), —110.8 (2F, d, J=260 Hz, CF$_2$), −108.8 (2F, d, J=260 Hz, CF$_2$), MS (ASAP+): 535.2 (100, [M−H$_2$O+H]$^+$), 553.3 (30, [M+H]$^+$).

9,9-bis(1,1,2,2-tetrafluorooctane) fluorene 3

The octafluoronated tertiary alcohol (2.0 g, 3.62 mmol) was dissolved in a mixture of thionyl chloride (7.9 mL, 109 mmol) and pyridine (1.6 mL, 19.5 mmol). The reaction mixture was stirred under argon at 100° C. for 3 days, after which the reaction mixture was allowed to cool to room temperature and was added dropwise to ice cold water (200 mL). The product was then extracted with diethyl ether (3×100 mL). The combined organics were dried (MgSO$_4$), filtered and the solvent was evaporated under reduced pressure. The crude product was purified by flash chromatography (hexane to 5% EtOAc in hexane), which yielded the product 3 as a colourless oil (0.3 g, 0.56 mmol, 15%). $^1$H NMR (400 MHz, CDCl$_3$), δ=0.80 (6H, t, J=7 Hz, CH$_3$), 1.06-1.30 (16H, m, CH$_2$), 1.46-1.58 (4H, m, CH$_2$), 7.33 (2H, td, J=7.7 Hz, 1.2 Hz, Ar—H), 7.50 (2H, td, J=7.5 Hz, 1.0 Hz, Ar—H), 7.75 (2H, br d, J=7.5 Hz, Ar—H), 7.79 (2H, br d, J=7.8 Hz, Ar—H); $^{19}$F NMR (376 MHz, CDCl$_3$), −109.7 (CF$_2$), −107.9 (CF$_2$).

2,7-dibromo-9,9-bis(1,1,2,2-tetrafluorooctane) fluorene 4

N-Bromosuccinimide (0.23 g, 1.31 mmol) was added to a stirred solution of 9,9-bis(1,1,2,2-tetrafluorooctyl) fluorene (0.35 g, 0.66 mmol) in 12 mL of a 5:1 acetic acid, concentrated sulphuric acid solution. The reaction mixture was stirred for 16 h at 65° C. After cooling to room temperature the reaction mixture was poured into a 10% NaOH solution (100 mL) and the product was extracted from the aqueous solution with diethyl ether (3×50 mL). The combined organics were washed with 10% NaOH solution (50 mL) and water (50 mL). The organic layer was then dried (MgSO$_4$), filtered and the solvent was removed under reduced pressure. The crude product mixture was purified by flash chromatography (hexane). This yielded the product 4 as a white crystalline solid (0.22 g, 0.32 mmol, 48%). $^1$H NMR (400 MHz, CDCl$_3$), δ=0.83 (6H, t, J=7.0 Hz, CH$_3$), 1.13-1.26 (16H, m, CH$_2$), 1.62-1.76 (4H, m, CH$_2$), 7.57 (2H, d, J=8.2 Hz, Ar—H), 7.62 (2H, dd, J=8.2, 1.7 Hz, Ar—H), 7.88 (2H, br d, J=1.7 Hz, Ar—H); $^{19}$F NMR (376 MHz, CDCl$_3$), δ=−109.1 (4F, t, J=19 Hz, CF$_2$), −107.2 (4F, s, CF$_2$).

4'-octyloxybiphenyl-4-boronic acid 5

Potassium carbonate (9.43 g, 68.3 mmol) was added portionwise to a stirred solution of 4-bromo-4'-hydroxybiphenyl (10.0 g, 40.1 mmol) and 1-bromooctane (9.0 mL, 52.2 mmol) in butanone (100 mL). The reaction mixture was stirred at reflux for 16 h. In the morning the reaction mixture was allowed to cool to room temperature and the white solid was removed by filtration. The mother liquor was evaporated to dryness under reduced pressure and the crude product was purified by recrystalisation from ethanol. This yielded the product as a white solid (11.6 g, 32.2 mmol, 80%). The 4-bromo-4'-octyloxybiphenyl (4.0 g, 11.1 mmol) was dissolved in dry THF (100 mL) and cooled to −78° C. n-BuLi (5.3 mL, 13.3 mmol, 2.5 M in hexanes) was added dropwise to this solution and the reaction mixture was stirred under argon at −78° C. for 1 h. Trimethyl borate (2.47 mL, 22.1 mmol) was then added dropwise at −78° C. The reaction mixture was then allowed to warm to room temperature and was stirred for 18 h. In the morning a 2 M HCl solution (10 mL) was added and the mixture was stirred for 1 h. The product was extracted with diethyl ether (2×30 mL) and the combined organics were dried (MgSO$_4$), filtered and the solvent was removed under reduced pressure. The crude product was triturated under hexanes to yield the product 5 as a white solid (1.88 g, 5.8 mmol, 52%). $^1$H NMR (400 MHz, SO(CD$_3$)$_2$), δ=0.86 (3H, t, J=7.0 Hz, CH$_3$), 1.26-1.45 (10H, m, CH$_2$), 1.72 (2H, quin, J=6.6 Hz, CH$_2$), 3.99 (2H, t, J=6.5 Hz, CH$_2$), 7.00 (2H, dt, J=8.9, 2.1 Hz, Ar—H), 7.57-7.62 (4H, m, Ar—H), 7.84 (2H, d, J=8.3 Hz, Ar—H), 8.03 (2H, br s, OH).

Compound 6

Tetrakis(triphenylphosphine)palladium (37 mg, 10 mol %) was added to a stirred solution of 2,7-dibromo-9,9-bis(tetrafluorooctyl)fluorene (0.22 g, 0.32 mmol) and 4'-octyloxybiphenyl-4-boronic acid (0.26 g, 0.79 mmol) in degassed 1,2-dimethoxyethane (15 mL) and a degassed 20% solution of $Na_2CO_3$ in water (8 mL). The reaction mixture was stirred under argon at reflux for 18 h. After completion the mixture was allowed to cool to room temperature and the 1,2-dimethoxyethane was removed under reduce pressure. The aqueous layer was diluted with water (100 mL) and was then extracted with dichloromethane (100 mL, 2×50 mL). The combined organics were washed with brine (70 mL), dried ($MgSO_4$), filtered and evaporated to dryness under reduced pressure. The crude product mixture was purified by flash chromatography (20% dichloromethane in hexane) and then recrystalised from dichloromethane and ethanol to yield the product 6 as a white microcrystalline solid (0.25 g, 0.23 mmol, 72%). $^1$H NMR (400 MHz, $CDCl_3$), δ=0.78 (3H, t, J=7.0 Hz, $CH_3$), 0.90 (3H, t, J=7.0 Hz, $CH_3$), 1.06-1.53 (36H, m, $CH_2$), 1.56-1.65 (4H, m, $CH_2$), 1.82 (4H, quin, J=6.8 Hz, $CH_2$), 4.02 (4H, t, J=6.5 Hz, $CH_2$), 7.01 (4H, dt, J=8.8, 2.1 Hz, Ar—H), 7.58 (4H, dt, J=8.8, 2.1 Hz, Ar—H), 7.67 (4H, d, J=8.6 Hz, Ar—H), 7.72 (4H, d, 8.6 Hz, Ar—H), 7.79 (2H, dd, J=8.0, 1.6 Hz, Ar—H), 7.84 (2H, d, J=8 Hz, Ar—H), 8.08 (2H, br s, Ar—H); $^{13}$C NMR (100 MHz, $CDCl_3$), δ=14.1 ($CH_3$), 14.3 ($CH_3$), 20.3, 22.5 ($CH_2$), 22.8 ($CH_2$), 26.2 ($CH_2$), 28.8 (CH2), 29.4 ($CH_2$), 29.5 (2×$CH_2$), 31.4 ($CH_2$), 32.0 ($CH_2$), 68.3 ($CH_2$), 115.0, 120.3, 127.3, 127.6, 128.2, 128.7, 133.1, 139.1, 140.1, 140.3, 141.1, 159.0; $^{19}$F NMR (376 MHz, $CDCl_3$), δ=−109.4 ($CF_2$), −107.7 ($CF_2$); HRMS (ASAP+): m/z calculated for $[M+H]^+$=1095.6266, found 1095.6240.

0.0041 mol), $K_2CO_3$ (1.12 g, 0.0082 mol), toluene (30 ml) and water (15 ml) were all added to a 3-neck round bottomed flask and the system was evacuated, with the aid of a vacuum pump, and filled with nitrogen 3 times. Subsequently, $Pd(PPh_3)_4$ (0.24 g, 0.20 mmol) was added and the reaction mixture was heated to 90° C. overnight. The reaction mixture was poured into a separating funnel, in which water (10 ml) and more toluene (10 ml) was added. The organic layer was concentrated under reduced pressure with subsequent azeotropic drying using toluene. The crude product was purified by gravity column chromatography (silica gel) using gradient elution (30% $CH_2Cl_2$ in hexanes to 50% $CH_2Cl_2$ in hexanes) to yield 8 as a yellow powder (0.65 g, 38%). $^1$H NMR (400 MHz, $CDCl_3$): δ (ppm) 0.89 (t, 3H), 1.26-1.52 (m, 10H), 1.82 (quint, 2H), 4.04 (t, 2H), 7.05 (d, 2H), 7.53 (d, 1H), 7.85 (d, 2H), 7.90 (d, 1H).

4-(4-(Octyloxy)phenyl)-7-(4,4,5,5-tetramethyl-1,3,2-dioxaborolan-2-yl)-2,1,3-benzothiadiazole 9

Compound 8 (0.60 g, 0.0014 mol), bis(pinacolato)diboron (0.40 g, 0.0016 mol), potassium acetate (0.42 g, 0.0043 mol) and $PdCl_2$(dppf) (0.06 g, 0.07 mmol) were added to a round bottomed flask and purged with nitrogen. De-gassed dry dioxane (15 ml) was added by syringe and the reaction mixture heated to 80° C. for 14 hours. The reaction mixture was filtered and the dioxane was removed using a rotary evaporator. The crude product was purified by gravity column chromatography (silica gel) using gradient elution ($CH_2Cl_2$ and 5% ethyl acetate in $CH_2Cl_2$) to yield 9 a yellow-brown solid (0.34 g, 51%). $^1$H NMR (400 MHz, $CDCl_3$): δ (ppm) 0.92 (t, 3H), 1.28-1.54 (m, 10H), 1.48 (s, 12H), 1.85 (quint, 2H), 4.06 (t, 2H), 7.08 (d, 2H), 7.68 (d, 1H), 7.94 (d, 2H), 8.26 (d, 1H).

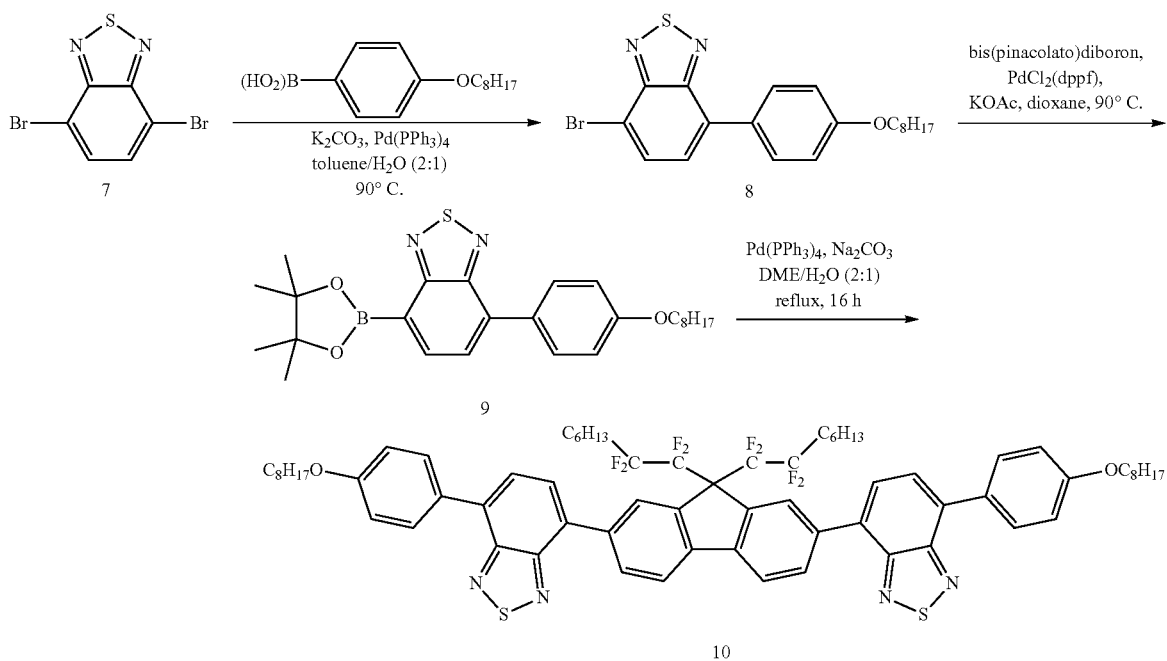

Scheme 2 Synthesis of 9,9-difluoroalkylfluorene-2,7-benzo[c]-1,2,5-thiadiazole derivatives

4-Bromo-7-(4-octyloxyphenyl)-2,1,3-benzothiadiazole 8

4-Octyloxyphenylboronic acid (1.02 g, 0.0041 mol), 4,7-dibromobenzo[c]-1,2,5-thiadiazole (compound 7, 1.20 g,

Compound 10

Tetrakis(triphenylphosphine) palladium (10 mg, 8.7 μmol) was added to a stirred solution of 2,7-dibromo-9,9-(1'1'2'2'-tetrafluorooctyl)fluorene (61 mg, 87.7 μmol) and compound 9 (90 mg, 0.19 mmol) in degassed 1,2-dimethoxyethane (15 mL) and degassed 20% $Na_2CO_3$ solution (8 mL). The reaction mixture was stirred under argon at reflux overnight. After completion the mixture was allowed to cool to room temperature and the 1,2-dimethoxyethane was removed under reduced pressure. The aqueous layer was then extracted with dichloromethane (100 mL, 2×50 mL) and the combined organics were washed with brine (70 mL), dried ($MgSO_4$), filtered and evaporated under reduced pressure. The crude product mixture was purified by flash chromatography (30% dichloromethane in hexane) and then recrystalised from a dichloromethane ethanol mixture. This yielded the product 10 as a crystalline yellow solid (69 mg, 57.0 μmol) m.p. 120° C. $^1$H NMR (400 MHz, $CDCl_3$): δ (ppm) 0.75 (t, J=7.0 Hz, 6H), 0.91 (t, J=6.9 Hz, 6H), 1.06-1.16 (m, 12H), 1.20-1.27 (m, 4H), 1.29-1.41 (m, 16H), 1.51 (quin, J=7.2 Hz, 4H), 1.58-1.69 (m, 4H), 1.85 (quin, J=7.0 Hz, 4H), 4.07 (t, J=6.6 Hz, 4H), 7.10 (td, J=8.8, 2.5 Hz, 4H), 7.79 (d, J=7.4 Hz, 2H), 7.87 (d, J=7.4 Hz, 2H), 7.95 (td, J=8.8, 2.4 Hz, 4H), 7.98 (d, J=8.0 Hz, 2H), 8.28 (dd, J=8.0, 1.5 Hz, 2H) 8.40 (br s, 2H); Mass (MALDI)=1210.5 ($M^+$).

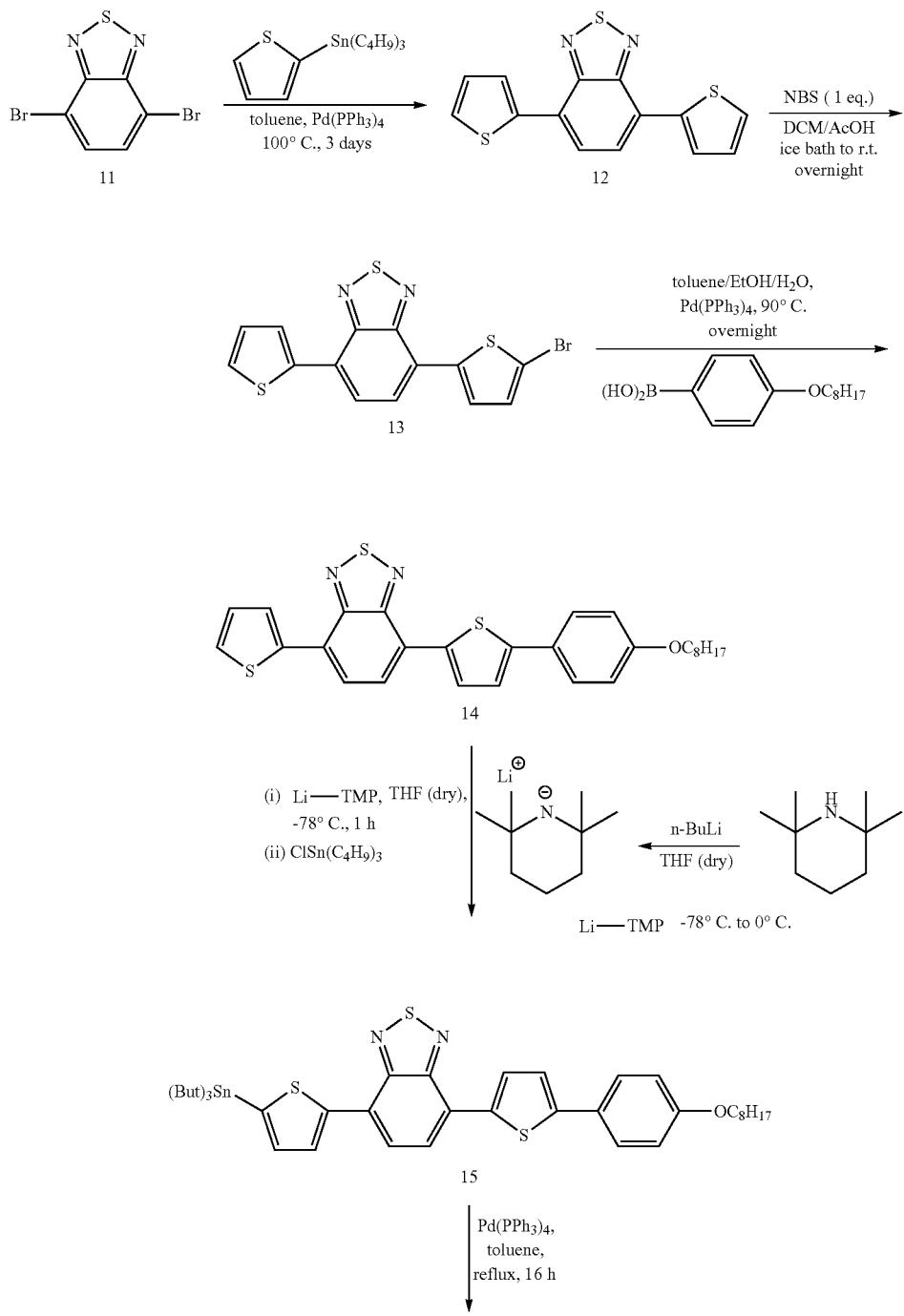

Scheme 3 Synthesis of 9,9-difluoroalkylfluorene-2,7-thiophene/benzo[c]-1,2,5-thiadiazole derivatives

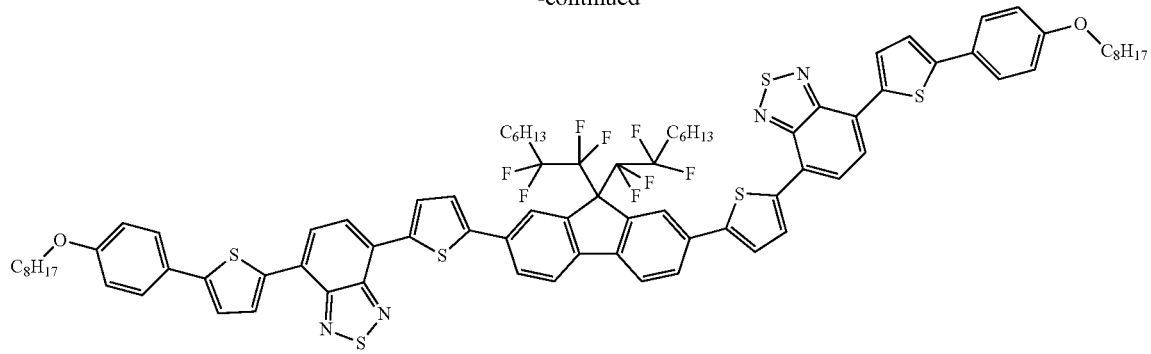

16

4,7-Di-2-thienyl-2,1,3-benzothiadiazole 12

A solution with reaction mixture of 4,7-dibromobenzo[c]-1,2,5-thiadiazole (compound 11, 2.00 g, 0.0068 mol), 2-(tributylstannyl)thiophene (5.59 g, 0.0150 mol) and toluene (30 ml) was bubbled through with nitrogen to deoxygenate the solvent. Under a nitrogen atmosphere Pd(PPh$_3$)$_4$ (0.50 g, 0.43 mmol) was added and heated at 90° C. with stirring for 3 days. The toluene was removed under reduced pressure and the crude product purified by gravity column chromatography (silica gel) using eluent 30% CH$_2$Cl$_2$ in hexanes followed by 2× recrystallisation from hexane to yield 12 as bright red crystals (1.21 g, 59%). $^1$H NMR (400 MHz, CDCl$_3$): δ (ppm) 7.20 (dd, 2H), 7.45 (dd, 2H), 7.88 (s, 2H), 8.12 (dd, 2H).

4-(5-Bromo-2-thienyl)-7-(2-thienyl)-2,1,3-benzothiadiazole 13

N-Bromosuccinimide (recrystallised from water, 0.59 g, 3.3 mmol) was slowly added to a solution of compound 12 (1.00 g, 3.3 mmol) in dry DCM (40 ml) and acetic acid (20 ml) in an ice-water bath with stirring. The resulting reaction mixture was stirred overnight at room temperature. The reaction mixture was added to DCM (500 ml) and a saturated aqueous NaHCO$_3$ solution (100 ml) was added. The organic layer was washed with water (2×200 ml), dried (MgSO4), filtered and concentrated under reduced pressure. The crude product was purified by gravity column chromatography (silica gel) using 20% CH$_2$Cl$_2$ in hexanes to yield 13 as a red powder (0.75 g, 60%). $^1$H NMR (400 MHz, CDCl$_3$): δ (ppm) 7.16 (d, 1H), 7.22 (dd, 1H), 7.47 (dd, 1H), 7.79-7.82 (m, 2H), 7.87 (d, 1H), 8.13 (dd, 1H).

4-(5-(4-Octyloxyphenyl-2-thienyl)-7-(2-thienyl)-2,1,3-benzothiadiazole 14

4-Octyloxyphenylboronic acid (0.69 g, 2.77 mmol), compound 13 (0.70 g, 1.85 mmol), K$_2$CO$_3$ (1.27 g, 9.23 mmol), toluene (40 ml), ethanol (5 ml) and water (20 ml) were all added to a 3-neck round bottomed flask and the system was evacuated, with the aid of a vacuum pump, and filled with nitrogen 3 times. Subsequently, Pd(PPh$_3$)$_4$ (0.10 g, 0.09 mmol) was added and the reaction mixture was heated to 90° C. overnight. The reaction mixture was poured into a separating funnel, in which water (10 ml) and more toluene (10 ml) was added. The organic layer was concentrated under reduced pressure with subsequent azeotropic drying. The crude product was purified by flash column chromatography (silica gel) using 30% CH$_2$Cl$_2$ in hexanes as the eluent to yield 14 as a red powder (0.55 g, 59%). $^1$H NMR (400 MHz, CDCl$_3$): δ (ppm) 0.92 (t, 3H), 1.28-1.40 (m, 8H), 1.48 (quint, 2H), 1.83 (quint., 2H), 4.03 (t, 2H), 6.97 (d, 2H), 7.24 (dd, 1H), 7.33 (d, 1H), 7.48 (dd, 1H), 7.65 (d, 2H), 7.90 (d, 2H), 8.12 (d, 1H), 8.15 (dd, 1H).

4-(5-(4-Octyloxyphenyl-2-thienyl)-7-(5-(tributylstannyl)-2-thienyl)-2,1,3-benzothiadiazole 15

All glassware were placed in a hot oven overnight prior to use and cooled to room temperature under nitrogen atmosphere. n-BuLi (2.5M in hexanes, 0.17 ml, 0.41 mmol) was slowly added dropwise to a solution of 2,2,6,6-tetramethylpiperidine (0.07 g, 0.50 mmol) in dry THF (5 ml) at −78° C. and stirred for 15 minutes. The reaction mixture was warmed to room temperature by removing the dry ice/acetone bath and stirred at room temperature for 15 minutes, and again cooled back down to −78° C. A solution of compound 14 (0.20 g, 0.40 mmol) in dry THF (15 ml) was added dropwise to the lithium salt and stirred for 1 hour at −78° C. Finally, the reaction was quenched with tributyltin chloride (0.15 g, 0.13 ml, 0.46 mmol) and stirred overnight at room temperature. Water was added and a work-up was carried out using CH$_2$Cl$_2$, dried (K$_2$CO$_3$), filtered and concentrated under reduced pressure. The crude product 15 was used in the next step without further purification or characterisation.

Compound 16

Tetrakis(triphenylphosphine) palladium (5 mg, 10 mol %) was added to a stirred solution of 2,7-dibromo-9,9-bis (1'1'2'2'-tetrafluorooctyl)fluorene (35 mg, 50 μmop and compound 15 (100 mg, 0.13 mmol) in degassed toluene (5 mL). The reaction mixture was stirred at reflux overnight. In the morning the reaction mixture was allowed to cool to room temperature and then washed with water (20 mL) and the aqueous layer was washed with dichloromethane (2×20 mL). The combined organics were dried (MgSO4), filtered and the solvent was removed under reduced pressure. The crude product was purified by flash chromatography (5%-40% dichloromethane in hexane) which yielded the product 16 as a dark red solid (34 mg, 44%). $^1$H NMR (400 MHz, CDCl$_3$): δ (ppm) 0.78 (t, J=7.0 Hz, 6H), 0.90 (t, J=6.9 Hz, 6H), 1.09-1.40 (m, 32H), 1.44-1.52 (m, 4H), 1.62-1.75 (m, 4H), 1.81 (quin, J=7.0 Hz, 4H), 4.00 (t, J=6.6 Hz, 4H), 6.95 (td, J=8.8, 2.5 Hz, 4H), 7.31 (d, J=3.9 Hz, 2H), 7.52 (d, J=3.9 Hz, 2H), 7.63 (td, J=8.8, 2.5 Hz, 4H), 7.77 (d, J=8.1 Hz, 2H), 7.84-7.93 (m, 6H), 8.11-8.16 (m, 6H); Liquid crystalline transitions (° C.): [Cr glass N 170 I]. Mass (MALDI)= 1538.4 (M+).

(50 ml) and the combined organic layers washed with water (100 ml) and dried (MgSO$_4$). After filtering off the MgSO$_4$ the crude product was purified by gravity column chroma-

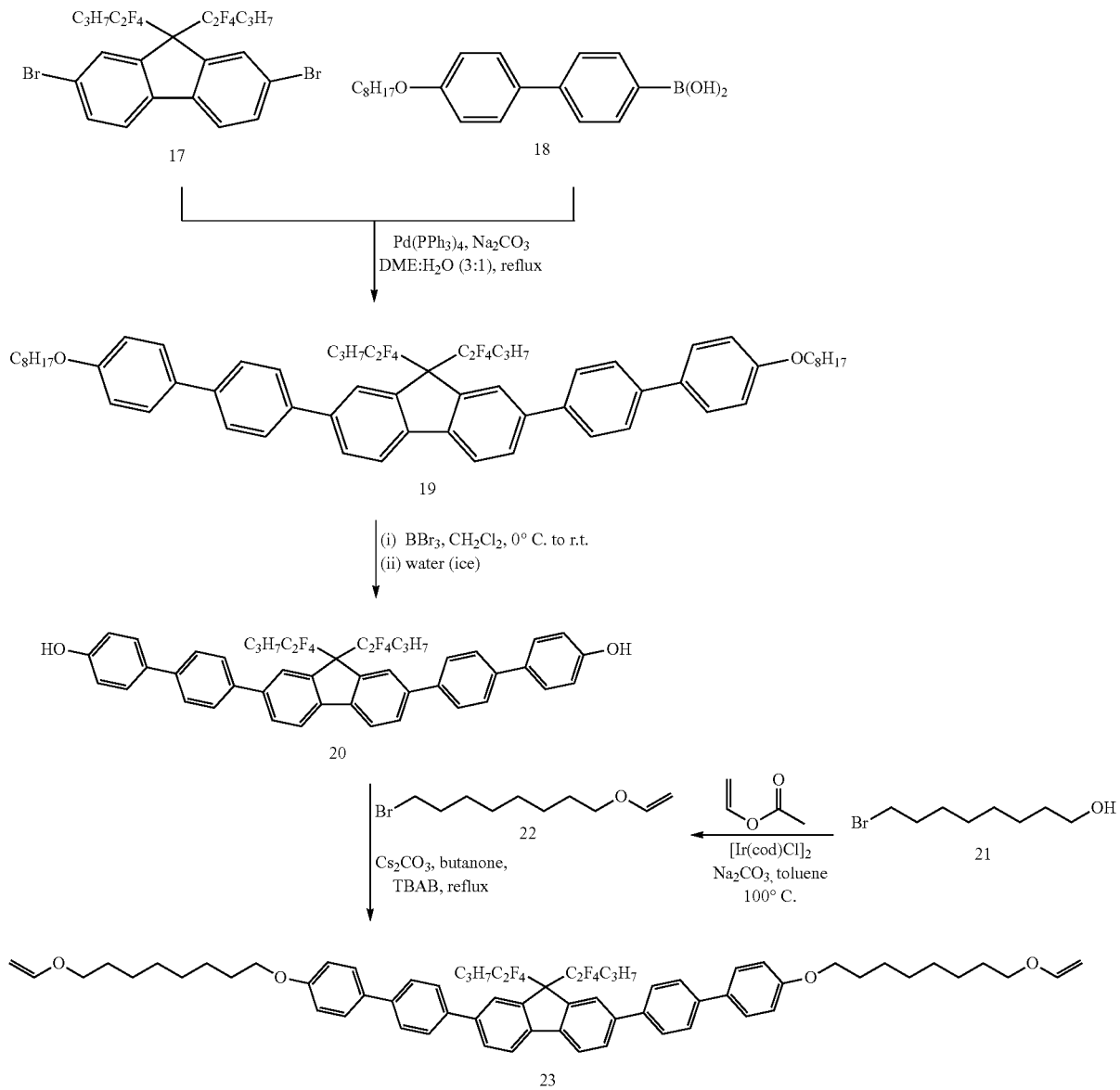

Scheme 4 Synthesis of fluoroalkylfluorene derivative 23 with electron rich cross linker 2,7-Bis(4-octyloxybiphenyl-4'-yl)-9-9-di(1,1,2,2 tetrafluoropentane)fluorene 19

4-Octyloxybiphenyl-4'-yl boronic acid (compound 18, 0.52 g, 1.59 mmol), 2,7-dibromo-9,9-di(1,1,2,2 tetrafluoropentane)fluorene (compound 17, 0.42 g, 0.69 mmol), K$_2$CO$_3$ (0.48 g, 3.45 mmol), DME (15 ml) and water (5 ml) were all added to a 3-neck round bottomed flask and the system was evacuated, with the aid of a vacuum pump, and filled with nitrogen 3 times. Subsequently, Pd(PPh$_3$)$_4$ (0.08 g, 0.07 mmol) was added and the reaction mixture was stirred under reflux overnight. The reaction mixture was poured into a separating funnel, in which water (100 ml) and CH$_2$Cl$_2$ (100 ml) were both added, the water layer washed with CH$_2$Cl$_2$ tography (silica gel) using gradient elution (20% CH$_2$Cl$_2$ in hexanes to 50% CH$_2$Cl$_2$ in hexanes) to yield 19 a white powder (0.45 g, 64%). Liquid crystalline transitions (° C.): [Cr 151 (N 144)I]. $^1$H NMR (400 MHz, CDCl$_3$): δ (ppm) 0.77 (trip., 6H), 0.92 (trip., 6H), 1.24-1.55 (m, 24H), 1.64 (quint., 4H), 1.85 (quint., 4H), 4.04 (trip., 4H), 7.03 (d, 4H), 7.61 (d, 4H), 7.68-7.87 (m, 12H), 8.10 (s, 2H). Liquid crystalline transitions (° C.): [Cr 151 (N 144) I].

2,7-Bis(4-hydroxybiphenyl-4'-yl)-9-9-di(1,1,2,2 tetrafluoropentane)fluorene 20

Boron tribromide (0.50 g, 0.19 ml, 1.98 mmol) was slowly added to a solution of compound 19 (0.40 g, 0.40 mmol) in dry CH$_2$Cl$_2$ (10 ml) in an ice/salt/water bath. The reaction mixture was warmed to room temperature and stirred overnight. After TLC indicated total de-alkylation the reaction mixture was poured into an ice-water mixture (50 ml) and stirred for a further one hour. The aqueous layer was washed with more CH$_2$Cl$_2$ (2×50 ml) and the combined organic extracts washed with water, dried (MgSO$_4$) and filtered. After concentration under reduced pressure 20 was afforded as an off-white powder (0.25 g, 80.6%). $^1$H NMR (400 MHz, CDCl$_3$): δ (ppm) 0.77 (t, 6H), 1.29 (quint., 8H), 4.85 (s, 2H), 6.97 (d, 4H), 7.57 (d, 4H), 7.67-7.87 (m, 12H), 8.10 (s, 2H).

8-Bromo-1-vinyloxy octane 22

A one-neck round bottomed flask equipped with a water condenser was dried under vacuum using a heat gun. After cooling down to room temperature 8-bromo-1-octanol (compound 21), vinyl acetate (dried and distilled), Na$_2$CO$_3$ (dried at 80° C. under vacuum for 5 hours) and dry toluene (20 ml) were added and purged with nitrogen gas. The catalyst [Ir(cod)Cl]$_2$ was added and the reaction mixture was stirred at 100° C. for 2 hours. The reaction mixture was cooled to 50° C. and the toluene was removed under high vacuum (oil pump) and the crude product was purified by a short silica gel plug using 20% DCM in hexanes as the solvent to yield a yellow oil (1.50 g, 60%). $^1$H NMR (400 MHz, CDCl$_3$): δ (ppm) 1.30-1.45 (m, 8H), 1.65 (quint., 2H), 1.85 (quint., 2H), 3.40 (t, 2H), 3.67 (t, 2H), 3.97 (dd, 1H), 4.16 (dd, 1H), 6.46 (dd, 1H).

Compound 23

Compound 20 (0.25 g, 0.32 mmol), compound 22 (0.19 g, 0.79 mmol), Cs$_2$CO$_3$ (0.52 g, 1.59 mol) and tetrabutylammonium bromide (spatula tip) in butanone (10 ml) were stirred at reflux overnight under a nitrogen atmosphere. The salts were filtered off, butanone removed under reduced pressure and the crude product was left over a one week period to crystallize out. The resulting solid was washed with ethanol and filtered to yield 23 as a white powder (0.18 g, 51.4%). Liquid crystalline transitions (° C.): [Cr 85 N 121 I]. $^1$H NMR (400 MHz, CDCl$_3$): δ (ppm) 0.77 (trip., 6H), 1.30 (quint., 8H), 1.35-1.55 (m, 16H), 1.69 (quint., 4H), 1.85 (quint., 4H), 3.71 (trip., 4H), 4.00 (dd, 2H), 4.04 (trip., 4H), 4.20 (dd, 2H), 6.50 (dd, 2H), 7.03 (d, 4H), 7.61 (d, 4H), 7.68-7.87 (m, 12H), 8.10 (s, 2H).

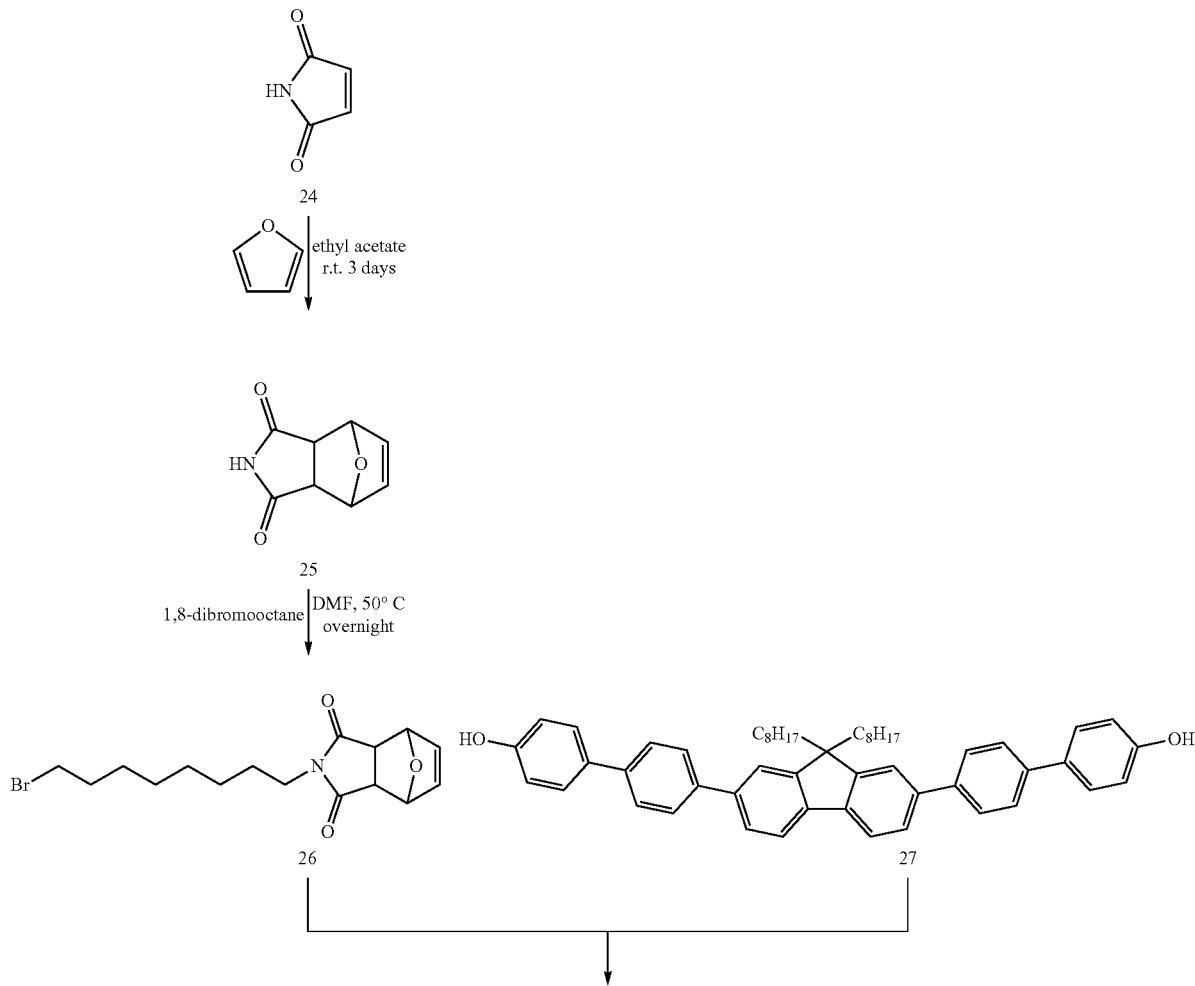

Scheme 5 Synthesis of cross linkable fluorene derivative with maleimide (electron poor) cross linkers -continued

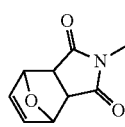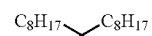

28

toluene, reflux
Yield = 95%

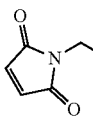

29

3,6-endo, exo-oxo-Δ⁴-tetrahydrophthalimide 25

A solution of maleimide (24, 2.50 g, 0.0258 mol) and furan (10 ml) in ethyl acetate (20 ml) was stirred at room temperature for 3 days. The resulting precipitate was filtered and dried under vacuum to yield a white powder (3.00 g, 71%). The product 25 was obtained as a mixture of endo- and exo-adducts (1.6:1). $^1$H NMR (400 MHz, CDCl$_3$): δ (ppm) endo product: 3.6 (s, 2H), 5.35 (s, 2H), 6.6 (s, 2H), exo product: 2.9 (s, 2H), 5.35 (s, 2H), 6.6 (s, 2H).

8-(3,6-exo-oxo-Δ⁴-tetrahydrophthalimide)bromooctane 26

Compound 25 (0.76 g, 0.0046 mol), 1,8-dibromooctane (5.00 g, 0.0184 mol), K$_2$CO$_3$ (3.18 g, 0.0230 mol) and DMF (10 ml) was stirred at 55° C. under a nitrogen atmosphere overnight. The DMF was removed under reduced pressure and DCM was added and the salts filtered off. The crude product was purified by column chromatography (silica gel, 30% ethylacetate in hexane to 50% ethylacetate in hexane) to yield 26 as viscous liquid that crystallised overnight (0.40 g, 24%). $^1$H NMR (400 MHz, CDCl$_3$): δ (ppm) exo product: 1.20-1.60 (m, 10H), 1.85 (quint., 2H), 2.9 (s, 2H), 3.40 (trip., 2H), 3.50 (trip., 2H), 5.35 (s, 2H), 6.6 (s, 2H).

Compound 28

Compound 26 (0.30 g, 0.83 mmol), compound 27 (0.20 g, 0.28 mmol), TBAB (spatula tip) and Cs$_2$CO$_3$ (0.45 g, 1.38 mmol) in butanone (20 ml) were stirred at room temperature for 3 days and then 50° C. for 5 hours under a nitrogen atmosphere. The salts were filtered off, butanone removed under reduced pressure and the crude product was subjected to column chromatography (silica gel, 50% ethylacetate in hexane to 100% ethylacetate) to yield 28 as a viscous liquid (0.25 g, 71%). $^1$H NMR (400 MHz, CDCl$_3$): δ (ppm) exo product: 0.70-0.85 (m, 10H), 1.10-1.60 (m, 40H), 1.85 (quint., 4H), 2.10 (m, 4H), 2.85 (s, 4H), 3.50 (trip., 4H), 4.00 (trip., 4H), 5.35 (s, 4H), 6.6 (s, 4H), 7.00 (d, 4H), 7.60-7.90 (m, 18H).

Compound 29

Compound 5 (0.30 g, 0.23 mmol) was refluxed in toluene (10 ml) overnight to fully eliminate furan. The toluene was removed under reduced pressure to yield a viscous liquid that slowly crystallizes (0.27 g, 100%). $^1$H NMR (400 MHz, CDCl$_3$): δ (ppm) 0.71-0.84 (m, 10H), 1.04-1.65 (m, 40H), 1.83 (quint., 4H), 2.08 (m, 4H), 3.55 (trip., 4H), 4.04 (trip., 4H), 6.71 (s, 4H), 7.02 (d, 4H), 7.59-7.82 (m, 18H). Liquid crystalline transitions C): [Cr 74 N 102 I]. Mass (MALDI)= 1140.6 (M⁺).

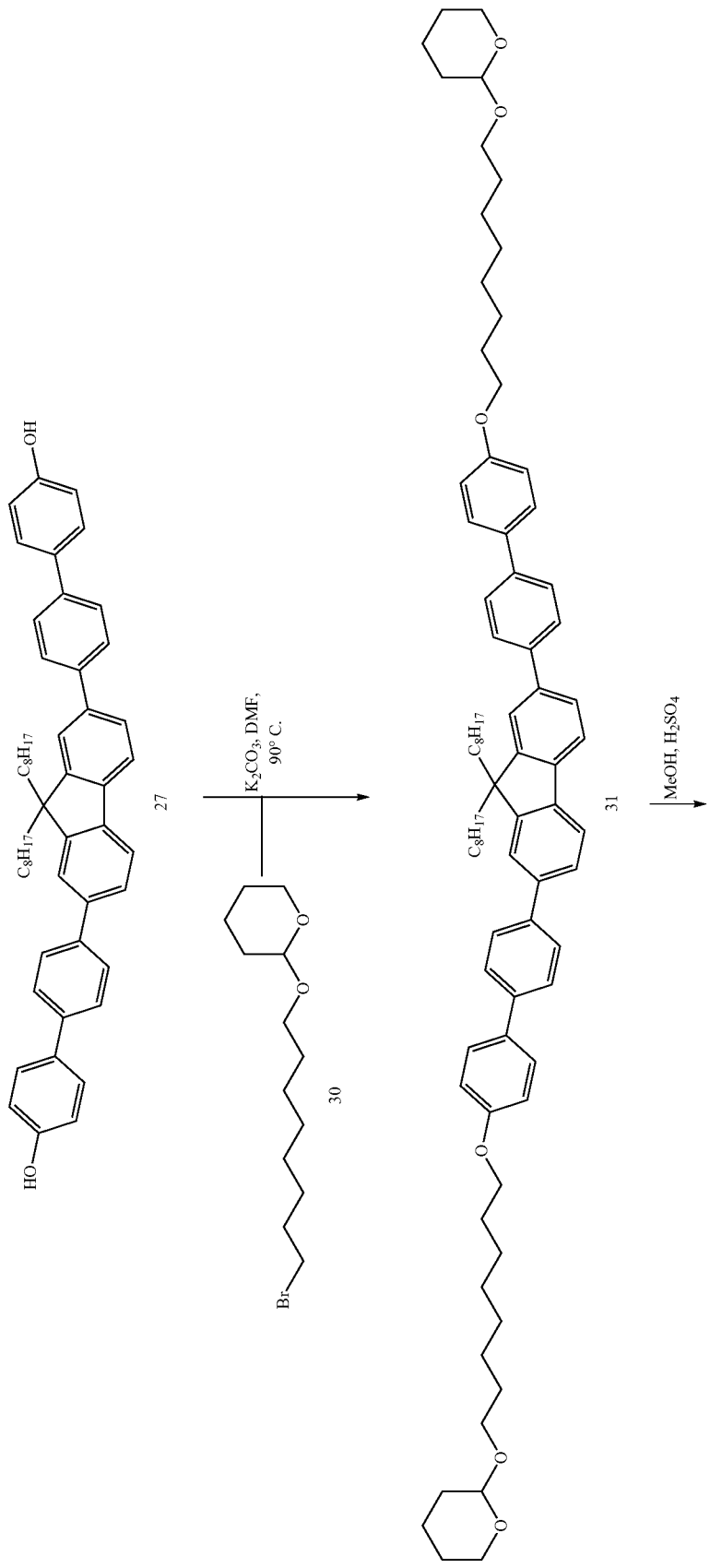

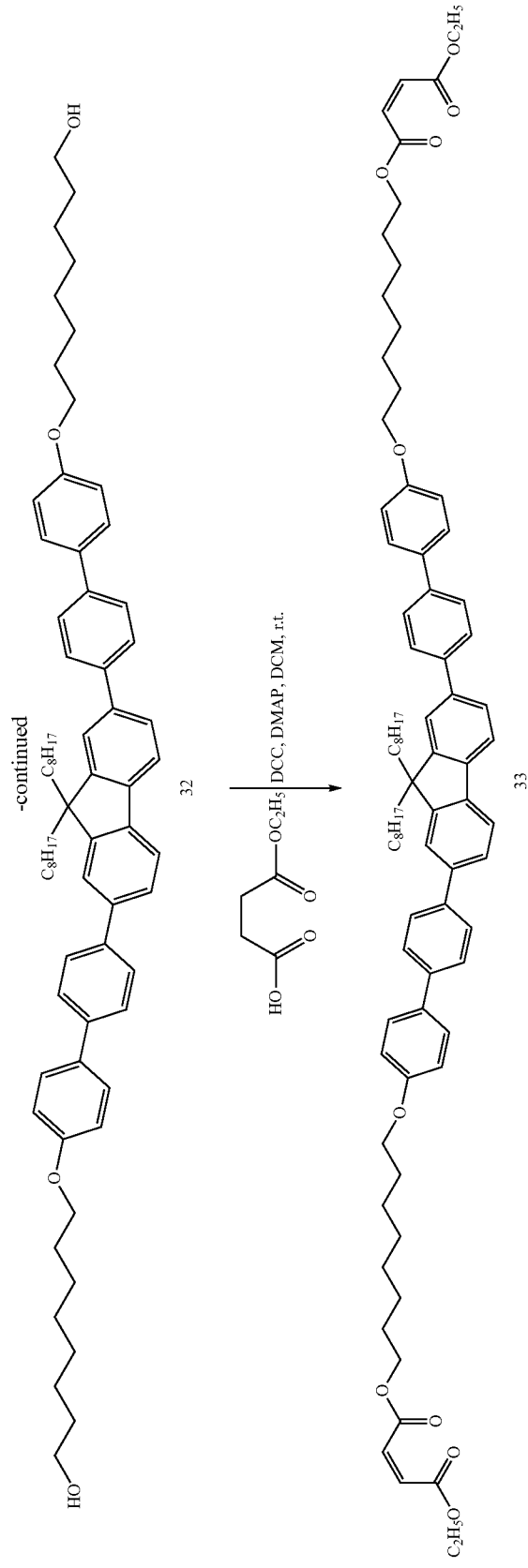

Compound 32

A reaction mixture of 2-(8-bromooctyloxy)tetrahydro-2H-pyran (compound 30, 0.97 g, 3.30 mmol), compound 27 (0.80 g, 1.10 mol) and $K_2CO_3$ (0.76 g, 5.50 mol) in dry DMF (10 ml) was stirred at 100° C. overnight. The reaction was cooled to room temperature and DMF was removed under reduced pressure. The crude product was dissolved in DCM and the salts were filtered off After removal of the DCM the crude product (compound 31) was dissolved in methanol (20 ml) and refluxed with conc. sulphuric acid (1 ml). After one hour the reaction mixture was cooled to room temperature and the formed precipitate was filtered and washed with copious amounts of water. After drying under vacuum the desired product 32 was a white powder (0.80 g, 74%, over two steps). $^1$H NMR (400 MHz, $CDCl_3$): δ (ppm) 0.71-0.84 (m, 10H), 1.06-1.74 (m, 40H), 1.85 (quint., 4H), 2.08 (m, 4H), 3.69 (trip., 4H), 4.05 (trip., 4H), 7.02 (d, 4H), 7.60-7.82 (m, 18H), —OH protons not detected.

Compound 33

DCC (0.24 g, 1.16 mmol) was added portionwise to a cooled (0° C.) solution of compound 32 (0.20 g, 0.20 mmol), mono-ethyl maleate (0.37 g, 2.8 mmol) and DMAP (0.10 g, 0.82 mmol) in dry $CH_2Cl_2$ (6 ml) under a nitrogen atmosphere. The reaction mixture was stirred for 20 h and the formed DCU was filtered and $CH_2Cl_2$ was removed under reduced pressure. The resulting residue was purified by column chromatography (silica gel) gradient elution (10% ethylacetate in hexanes to 20% ethylacetate in hexanes) to yield a viscous oil which slowly crystallised to a white low melting solid (0.10 g, 40%). $^1$H NMR (400 MHz, $CDCl_3$): δ (ppm) 0.70-0.83 (m, 10H), 1.05-1.56 (m, 42H), 1.72 (quint., 4H), 1.85 (quint., 4H), 2.08 (m, 4H), 4.04 (t, 4H), 4.22 (t, 4H), 4.28 (quint., 4H), 6.26 (s, 4H) 7.02 (d, 4H), 7.60-7.82 (m, 18H). Liquid crystalline transitions (° C.): [Cr 43 N 78 L]. Mass (MALDI)=1234.7 ($M^+$)

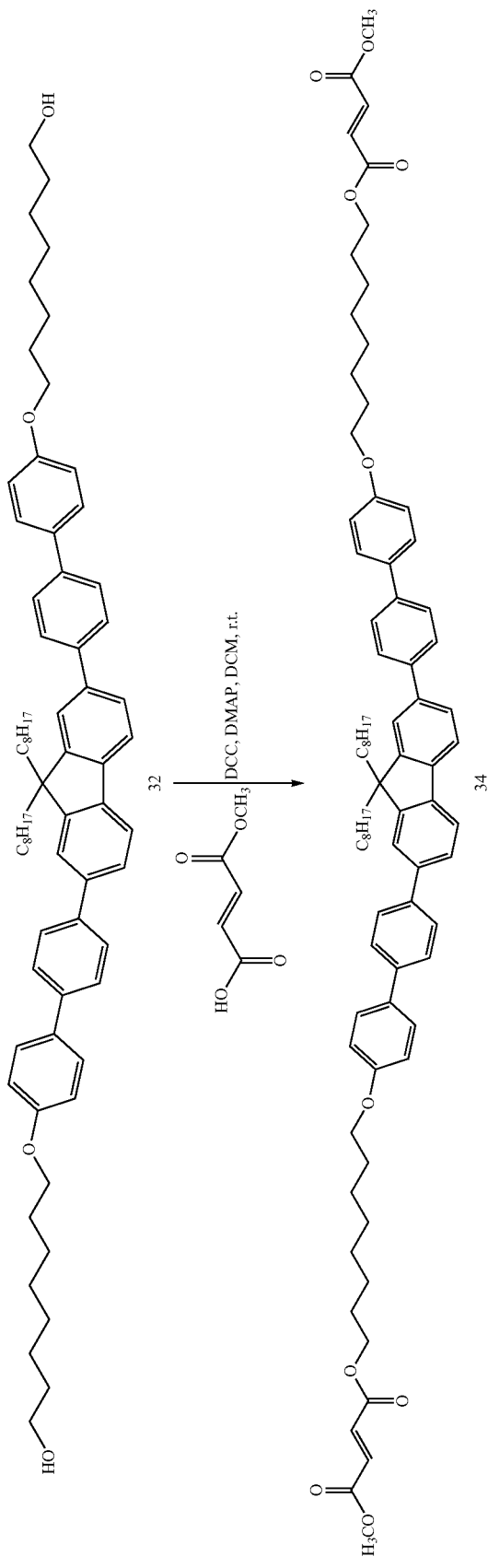

Compound 34

DCC (0.24 g, 1.16 mmol) was added portionwise to a cooled (0° C.) solution of compound 32 (0.20 g, 0.20 mmol), mono-methyl fumarate (0.26 g, 2.03 mmol) and DMAP (0.10 g, 0.82 mmol) in dry DCM (6 ml) under a nitrogen atmosphere. The reaction mixture was stirred overnight and the formed DCU was filtered and DCM was removed under reduced pressure. The resulting residue was purified by column chromatography gradient elution (silica gel, 10% ethylacetate in hexanes to 20% ethylacetate in hexanes) to yield a viscous oil that slowly crystallised over a few days. Then the product was triturated with hexane and filtered to yield 34 as a white powder (0.15 g, 60%). $^1$H NMR (400 MHz, CDCl$_3$): δ (ppm) 0.72-0.84 (m, 10H), 1.06-1.56 (m, 36H), 1.72 (quint., 4H), 1.85 (quint., 4H), 2.08 (m, 4H), 3.84 (s, 6H), 4.05 (t, 4H), 4.24 (t, 4H), 6.89 (s, 4H) 7.03 (d, 4H), 7.59-7.83 (m, 18H). Mass (MALDI)=1206.7 (M$^+$). Liquid crystalline transitions (° C.): [Cr 76 N 107 I].

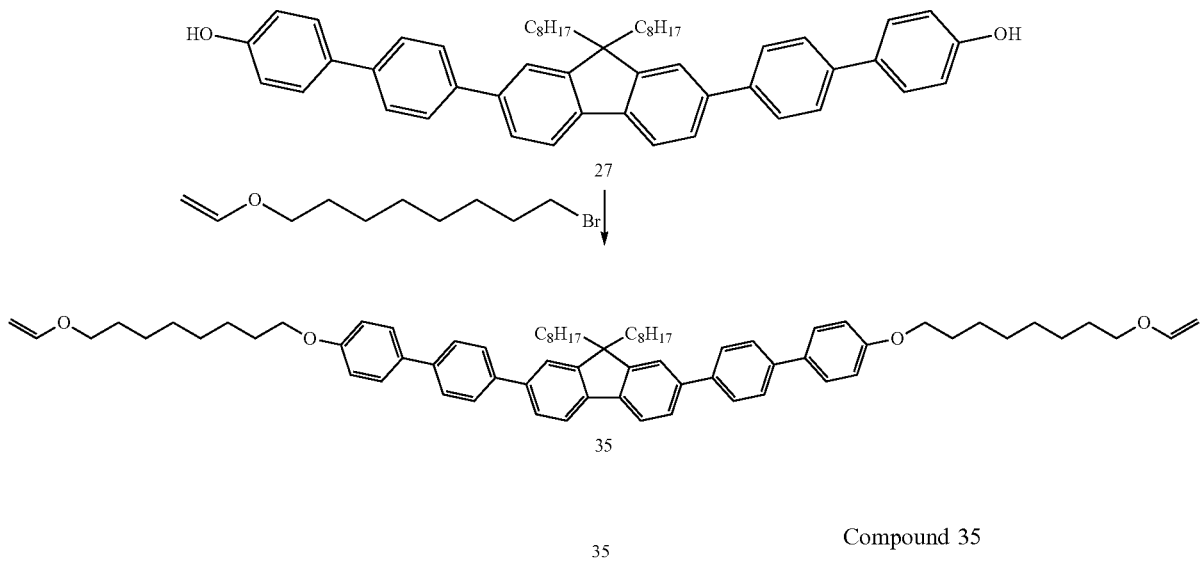

Scheme 7 Synthesis of cross linkable fluorene derivative 35 with vinyl ether (electron rich) cross linkers

Compound 35

Compound 27 (0.21 g, 0.29 mmol), 2-(8-bromooctyloxy) vinyl ether (0.16 g, 0.66 mmol) and K$_2$CO$_3$ (0.20 g, 1.44 mmol) in DMF (10 ml) were stirred at 90° C. overnight under a nitrogen atmosphere. The salts were filtered off, DMF removed under reduced pressure and the crude product was subjected to column chromatography (silica gel, 20% DCM in hexanes) to yield 35 as a white powder (0.05 g, 16.6%). $^1$H NMR (400 MHz, CDCl$_3$): δ (ppm) 0.74-0.84 (m, 10H), 1.07-1.56 (m, 36H), 1.71 (quint., 4H), 1.85 (quint., 4H), 2.08 (m, 4H), 3.72 (t, 4H), 4.00 (dd, 2H), 4.04 (t, 4H), 4.20 (dd, 2H), 6.50 (dd, 2H), 7.02 (d, 4H), 7.60-7.82 (m, 18H). Mass (MALDI)=1034.7 (M$^+$); Liquid crystalline transitions (° C.): [Cr 82 N 155 I].

Synthesis of Cross Linkable Fluoroalkylfluorene Derivatives with Vinyl Ether and Maleimide Cross Linking Groups

Compound 36

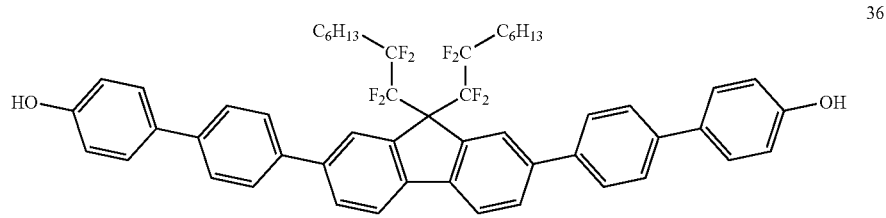

Synthesis of C8-diol (Compound 36)

Boron tribromide (1.3 mL, 13.5 mmol), was added dropwise to a stirred solution of C8-8 (compound 6, 2.94 g, 2.68 mmol), in dry dichloromethane (50 mL) at 0° C. The reaction mixture was allowed to warm to room temperature and then stirred for 16 h under argon. Ice water (50 mL) was then added to the reaction mixture and it was stirred for an additional hour, after which the layers were separated and the aqueous layer was extracted with dichloromethane (2×100 mL). The combined organics were dried (MgSO$_4$), filtered and the solvent was removed under reduced pressure. The residue was purified by trituration under hexane which yielded the product 36 as a white solid (2.01 g, 2.31 mmol, 86%). $^1$H NMR (400 MHz, CDCl$_3$), δ=0.78 (6H, t, J=7.0 Hz, CH$_3$), 1.06-1.24 (14H, m, CH$_2$), 1.52-1.65 (4H, m, CH$_2$), 4.77 (2H, s, OH), 6.95 (4H, dt, J=8.7, 2.1 Hz, Ar—H), 7.55 (4H, dt, J=8.6, 2.1 Hz, Ar—H), 7.66 (4H, d, J=8.4 Hz, Ar—H), 7.73 (4H, d, J=8.4 Hz, Ar—H), 7.80 (2H, dd, J=8.0, 1.5 Hz, Ar—H), 7.84 (2H, d, J=8.0 Hz, Ar—H), 8.07 (2H, br s, Ar—H); $^{19}$F NMR (376 MHz, CDCl$_3$), δ=−109.0 (CF$_2$), −107.2 (CF$_2$).

t, J=7.0 Hz, CH$_3$), 0.90 (3H, t, J=7.0 Hz, CH$_3$), 1.05-1.66 (30H, m, CH$_2$), 1.83 (2H, quin, J=6.8 Hz, CH$_2$), 4.02 (2H, t, J=6.6 Hz, CH$_2$), 4.84 (1H, s, OH), 6.95 (2H, dt, J=8.6, 2.1 Hz, Ar—H), 7.01 (2H, dt, J=8.8, 2.1 Hz, Ar—H), 7.56 (2H, dt, J=8.6, 2.1 Hz, Ar—H), 7.59 (2H, dt, J=8.8, 2.1 Hz, Ar—H), 7.65-7.68 (4H, m, Ar—H), 7.72-7.74 (4H, m, Ar—H), 7.78-7.81 (2H, m, Ar—H), 7.84 (2H, d, J=8.0 Hz, Ar—H), 8.08 (2H, br s, Ar—H); $^{19}$F NMR (376 MHz, CDCl$_3$), δ=−108.9 (CF$_2$), −107.2 (CF$_2$).

Compound 38

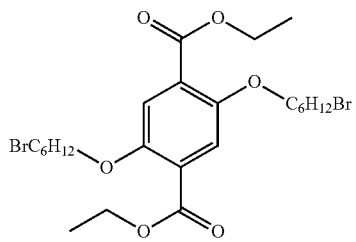

38

Compound 37

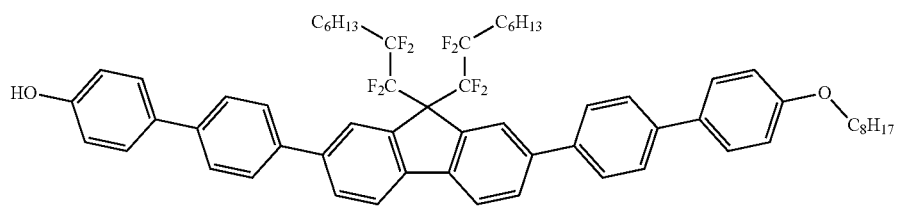

37

Synthesis of C8-mono octane (Compound 37)

K$_2$CO$_3$ (0.64 g, 4.60 mmol) was added portionwise to a stirred solution of C8-diol (2.00 g, 2.30 mmol) and 1-bromooctane (0.44 g, 2.30 mmol) in 2-butanone (100 mL). The reaction mixture was stirred at reflux for 18 h. The reaction mixture was then allowed to cool to room temperature and the remaining K$_2$CO$_3$ and salt were filtered off and washed with dichloromethane (50 mL). The filtrate was evaporated to dryness under reduced pressure and the crude product mixture was purified by flash chromatography (15-30% ethyl acetate in hexane). This yielded the product 37 as a white solid (0.86 g, 0.87 mmol, 38%) and the starting material 36 as an off white solid (1.09 g, 1.25 mmol, 54%). The reaction was run again using the recovered starting material 36 which brought the overall yield of 37 to 1.41 g, 1.43 mmol, 62%. $^1$H NMR (400 MHz, CDCl$_3$), δ=0.79 (6H,

Synthesis of diethyl-2,5-di(bromohexyl)oxyterephthalate (Compound 38)

K$_2$CO$_3$ (3.26 g, 23.6 mmol) was added portionwise to a stirred solution of diethyl-2,5-dihydroxyterephthalate (1.00 g, 3.93 mmol) and 1,6-dibromohexane (6.1 mL, 39.3 mmol) in 2-butanone (20 mL). The reaction mixture was stirred at reflux for 16 h, after which the K$_2$CO$_3$ and salt were filtered off and washed with dichloromethane (20 mL). The filtrate was then evaporated to dryness under reduced pressure and the crude product was purified by flash chromatography (10% ethyl acetate in hexane). This yielded the product 38 as a white solid (1.91 g, 3.29 mmol, 84%). $^1$H NMR (400 MHz, CDCl$_3$), δ=1.39 (6H, t, J=7.1 Hz, CH$_3$), 1.50-1.52 (8H, m, CH$_2$), 1.79-1.93 (8H, m, CH$_2$), 3.42 (4H, t, J=6.8 Hz, CH$_2$), 4.01 (4H, t, J=6.4 Hz, CH$_2$), 4.37 (4H, q, J=7.1 Hz, CH$_2$), 7.34 (2H, s, Ar—H).

Compound 39

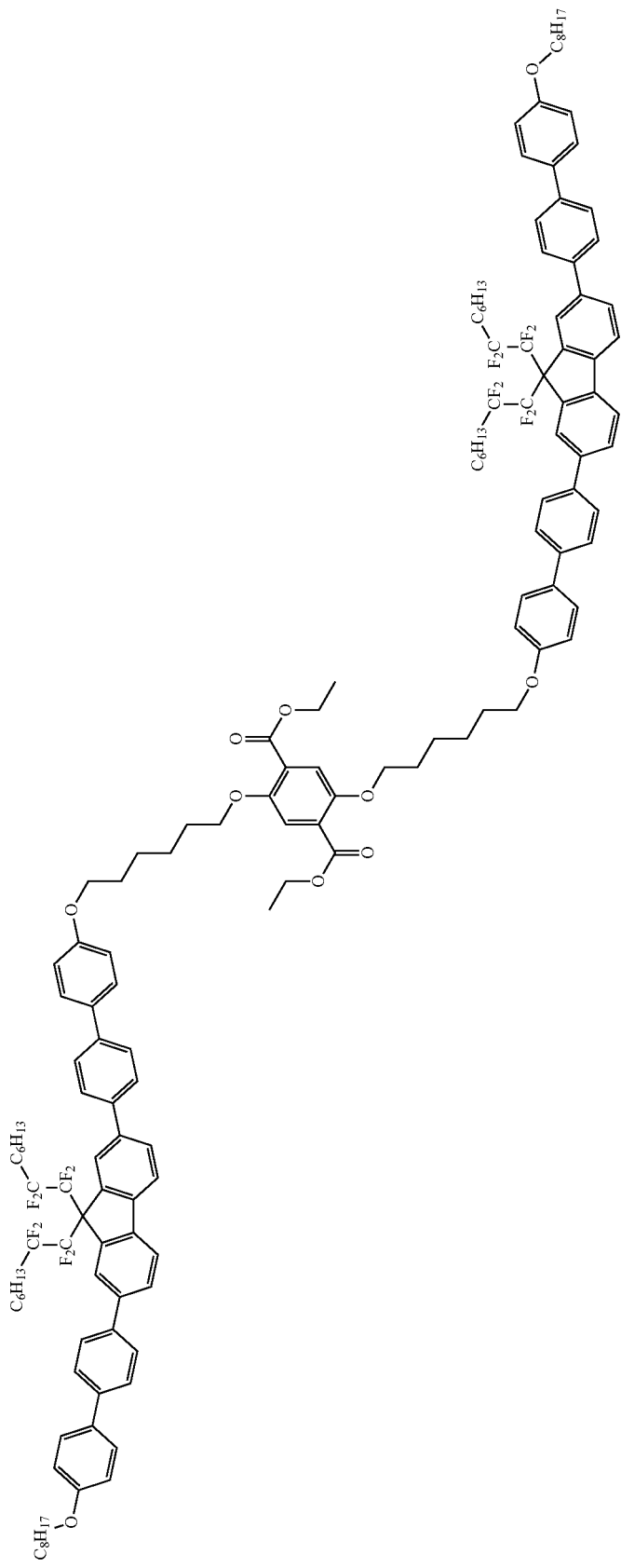

Synthesis of G8-8-diethylester (Compound 39)

$Cs_2CO_3$ (1.26 g, 3.88 mmol) was added portionwise to a stirred solution of diethyl-2,5-di(bromohexyl)oxyterephthalate 38 (0.38 g, 0.65 mmol) and C8-mono octane 37 (1.40 g, 1.42 mmol) in dry DMF (25 mL). The reaction mixture was stirred under argon at 90° C. for 18 h, after which the reaction mixture was allowed to cool to room temperature. The $Cs_2CO_3$ and salt were then filtered off and washed with dichloromethane (50 mL). The filtrate was evaporated under reduced pressure and the residue was purified by flash chromatography (dichloromethane). This yielded the product 39 as a white solid (1.15 g, 0.49 mmol, 75%). $^1$H NMR (400 MHz, $CDCl_3$), δ=0.78 (12H, t, J=7.0 Hz, $CH_3$), 0.90 (6H, t, J=6.9 Hz, $CH_3$), 1.06-1.66 (74H, m, $CH_2$+$CH_3$), 1.79-1.90 (12H, m, $CH_2$), 4.00-4.06 (12H, m, $CH_2$), 4.38 (4H, q, J=7.1 Hz, $CH_2$), 6.99-7.01 (8H, m, Ar—H), 7.36 (2H, s, Ar—H), 7.57-7.59 (8H, m, Ar—H), 7.66-7.68 (8H, m, Ar—H), 7.71-7.73 (8H, m, Ar—H), 7.78-7.84 (8H, m, Ar—H), 8.07 (4H, br s, Ar—H); $^{19}$F NMR (376 MHz, $CDCl_3$), δ=−108.84 ($CF_2$), −107.21 ($CF_2$); MS (MALDI+): m/z calculated for $[M+H]^+$=2384.2, found=2384.5.

Compound 40

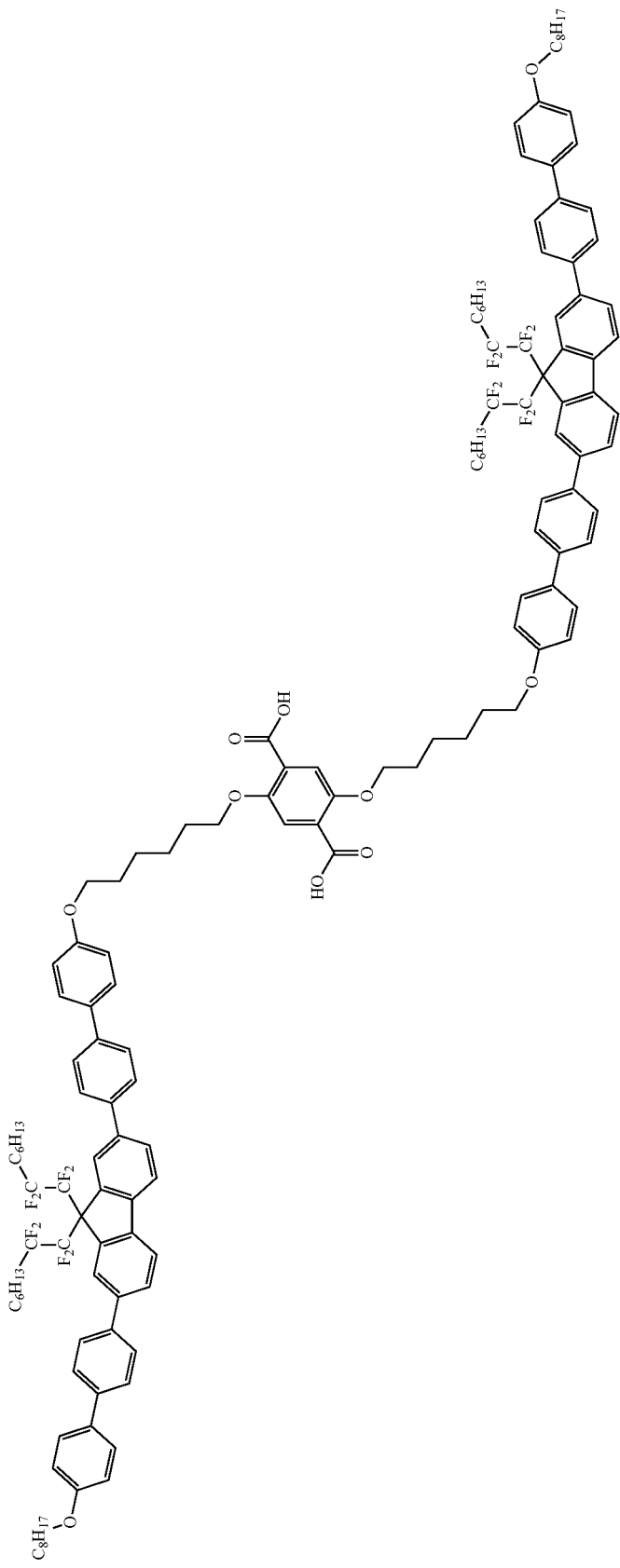

Synthesis of G8-8-diacid (Compound 40)

An aqueous 1 M solution of NaOH (10 mL) was added to a stirred solution of G8-8-diethylester 39 (1.15 g, 0.49 mmol) in tetrahydrofuran (12 mL). The reaction mixture was stirred at 50° C. for 3 days. On completion the solution was acidified with 2 M HCl and then extracted with dichloromethane (3×50 mL). The combined organic were dried ($MgSO_4$), filtered and the solvent was removed under reduced pressure to give the desired product 40 as an off white solid (1.04 g, 0.45 mmol, 91%). $^1$H NMR (400 MHz, $CDCl_3$), δ=0.78 (12H, t, J=7.0 Hz, $CH_3$), 0.90 (6H, t, J=6.9 Hz, $CH_3$), 1.06-1.66 (68H, m, $CH_2$), 1.79-2.02 (12H, m, $CH_2$), 4.00-4.06 (8H, m, $CH_2$), 4.33 (4H, t, J=6.6 Hz, $CH_2$), 6.98-7.01 (8H, m, Ar—H), 7.57-7.59 (8H, m, Ar—H), 7.66-7.73 (16H, m, Ar—H), 7.78-7.84 (8H, m, Ar—H), 7.89 (2H, s, Ar—H), 8.08 (4H, br s, Ar—H), 11.09 (2H, br s, OH); $^{19}$F NMR (376 MHz, $CDCl_3$), δ=−108.93 ($CF_2$), −107.20 ($CF_2$).

Compound 41

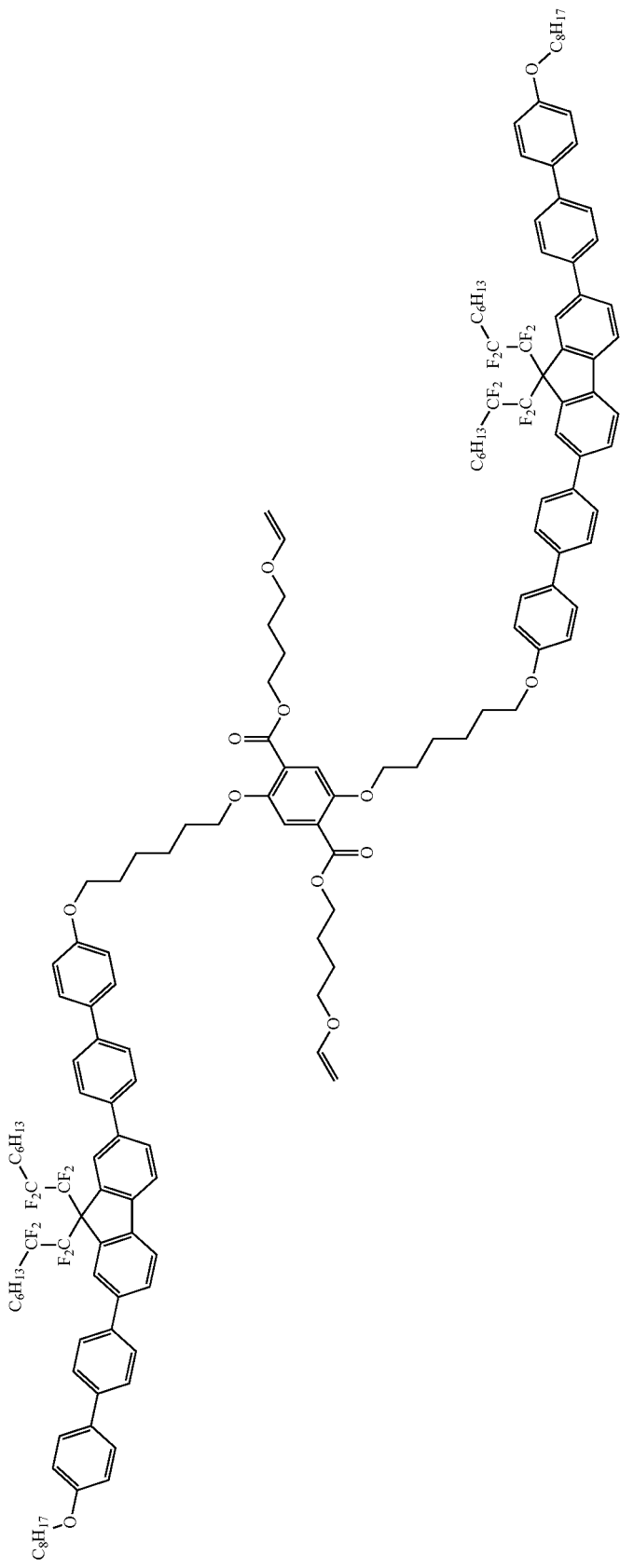

Synthesis of G8-8-VE (Compound 41)

N,N'-Dicyclohexylcarbodiimide (0.16 g, 0.76 mmol), was added to a stirred solution of G8-8-diacid 40 (0.45 g, 0.19 mmol) and 4-dimethylaminopyridine (9.3 mg, 0.076 mmol) in dry dichloromethane (7 mL) at 0° C. The mixture was then stirred under argon at 0° C. for 1 h, after which the 1,4-butanediol vinyl ether (0.089 g, 0.76 mmol) in dry dichloromethane (3 mL) was added and the reaction mixture was allowed to warm to room temperature and left to stir under argon for 18 h. After which the solution was diluted with dichloromethane (60 mL) and then washed with saturated NaHCO$_3$ (2×50 mL) and water (50 mL). The organic layer was then dried (MgSO$_4$), filtered and the solvent was removed under reduced pressure. The crude product was purified by flash chromatography (dichloromethane). This yielded the desired product 41 as a white solid (0.25 g, 0.098 mmol, 51%). $^1$H NMR (400 MHz, CDCl$_3$), δ=0.78 (12H, t, J=7.0 Hz, CH$_3$), 0.90 (6H, t, J=6.9 Hz, CH$_3$), 1.06-1.65 (68H, m, CH$_2$), 1.79-1.92 (20H, m, CH$_2$), 3.74 (3H, t, J=6.0 Hz, CH$_2$), 3.98-4.05 (14H, m, CH$_2$+=CH$_2$), 4.18 (2H, dd, J=14.4, 2.0 Hz, =CH$_2$), 4.36 (4H, t, J=6.2 Hz, CH$_2$), 6.47 (2H, dd, J=14.4, 6.8 Hz, =CH), 6.99-7.01 (8H, m, Ar—H), 7.37 (2H, s, Ar—H), 7.57-7.59 (8H, m, Ar—H), 7.65-7.73 (16H, m, Ar—H), 7.78-7.84 (8H, m, Ar—H), 8.07 (4H, br s, Ar—H); $^{19}$F NMR (376 MHz, CDCl$_3$), δ=−108.93 (CF$_2$), −107.21 (CF$_2$); MS (MALDI+): m/z calculated for [M+H]$^+$=2524.3, found=2524.8.

Compound 42

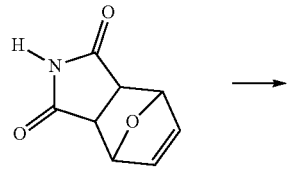

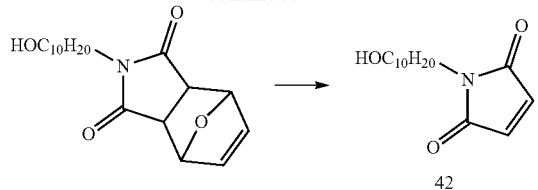

Synthesis of N-decanol-maleimide (Compound 42)

A solution of 10-bromo-1-decanol (2.9 g, 12.4 mmol) in dry DMF (10 mL) was added to a stirred suspension of furan protected maleimide (2.1 g, 12.4 mmol, as a mixture of endo and exo isomers) and K$_2$CO$_3$ (1.7 g, 12.4 mmol) in dry DMF (40 mL) under argon. The reaction mixture was then stirred at 50° C. under argon for 16 h (reaction turned dark red in colour overnight). After which the reaction mixture was poured into water (100 mL) and was extracted with ethyl acetate (3×50 mL). The combined organics were washed with water (100 mL) and brine (2×50 mL). The organic layer was then dried (MgSO$_4$), filtered and the solvent was removed under reduced pressure. The oily residue was triturated with the aid of sonication under hexane which was then decanted off. This process was repeated twice to remove any unreacted bromo-decanol. The oily residue was then dissolved in diethyl ether and filtered. The filtrate was evaporated to dryness under reduced pressure to yield the product as a colourless oil which solidified on standing overnight at room temperature (2.3 g, 7.2 mmol, 58%).

The mixture of endo/exo N-decanol-furan protected maleimide (1.2 g, 3.6 mmol) was heated to reflux in toluene (20 mL) and stirred at reflux for 18 h. After which the solvent was removed under reduced pressure and the crude product was purified by flash chromatography (30-50% ethyl acetate in hexane). This yielded the product 42 as a white solid (0.52 g, 2.1 mmol, 58%). $^1$H NMR (400 MHz, CDCl$_3$), δ=1.22-1.35 (12H, m, CH$_2$), 1.54-1.61 (4H, m, CH$_2$), 3.48-3.52 (2H, m, CH$_2$), 3.63 (2H, t, J=6.6 Hz, CH$_2$), 6.68 (2H, s, =CH).

Compound 43

43
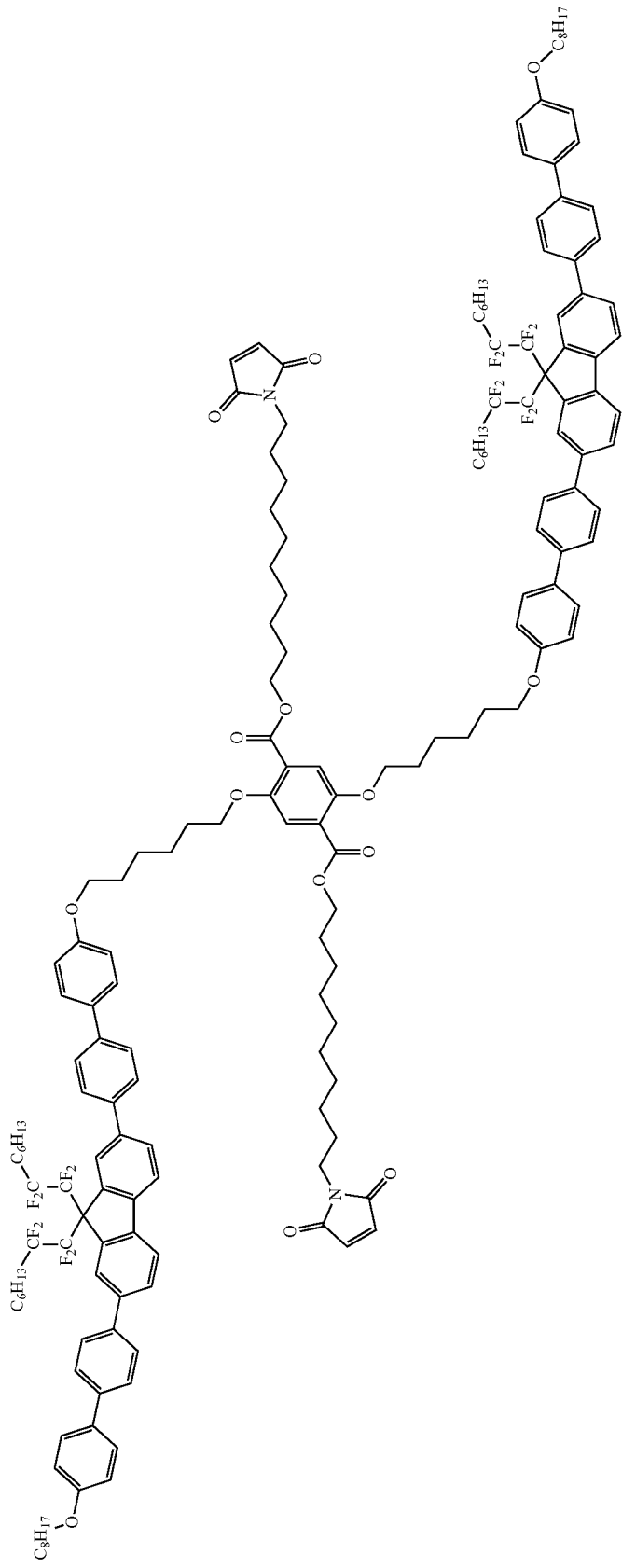

Synthesis of G8-8-MI (Compound 43)

N,N'-Dicyclohexylcarbodiimide (0.13 g, 0.64 mmol), was added to a stirred solution of G8-8-diacid 40 (0.60 g, 0.26 mmol) and 4-dimethylaminopyridine (3 mg, 0.026 mmol) in dry dicholoromethane (7 mL) at 0° C. The mixture was then stirred under argon at 0° C. for 1 h, after which the N-decanol-maleimide 42 (0.26 g, 1.0 mmol) in dry dichloromethane (3 mL) was added and the reaction mixture was allowed to warm to room temperature and left to stir under argon for 18 h. The solution was then diluted with dichloromethane (60 mL) and then washed with saturated $NaHCO_3$ (2×50 mL) and water (50 mL). The organic layer was then dried ($MgSO_4$), filtered and the solvent was removed under reduced pressure. The crude product was purified by flash chromatography (2% ethyl acetate in dichloromethane) which yielded the product 43 as yellow viscous oil (0.33 g, 0.12 mmol, 46%). $^1$H NMR (400 MHz, $CDCl_3$), δ=0.78 (12H, t, J=7.1 Hz, $CH_3$), 0.90 (6H, t, J=6.9 Hz, $CH_3$), 1.06-1.65 (96H, m, $CH_2$), 1.72-1.89 (16H, m, $CH_2$), 3.47-3.50 (4H, m, $CH_2$), 4.00-4.05 (12H, m, $CH_2$), 4.31 (4H, t, J=6.7 Hz, $CH_2$), 6.65 (4H, s, =CH), 6.99-7.01 (8H, m, Ar—H), 7.37 (2H, s, Ar—H), 7.57-7.59 (8H, m, Ar—H), 7.65-7.73 (16H, m, Ar—H), 7.78-7.84 (8H, m, Ar—H), 8.07 (4H, br s, Ar—H); $^{19}$F NMR (376 MHz, $CDCl_3$), δ=−108.93 ($CF_2$), −107.21 ($CF_2$); MS (MALDI+): m/z calculated for $[M+H]^+$=2799.5, found=2799.1.

Scheme 8 Synthesis of OLED Materials with Further Cross Linker Structures

The chemistry described above can be used to prepare alternative OLED materials of related structures owing to the modular nature of the synthesis. For example, compound 50 comprising a type 3 cross linker of structure can be made from 48. The protected $S^3$ spacer unit 48, and other similar structures are useful intermediates for the synthesis of materials for use in OLEDs. Exemplary regents are provided below. This chemistry can be equally applied to generate the other cross linking structures disclosed herein.

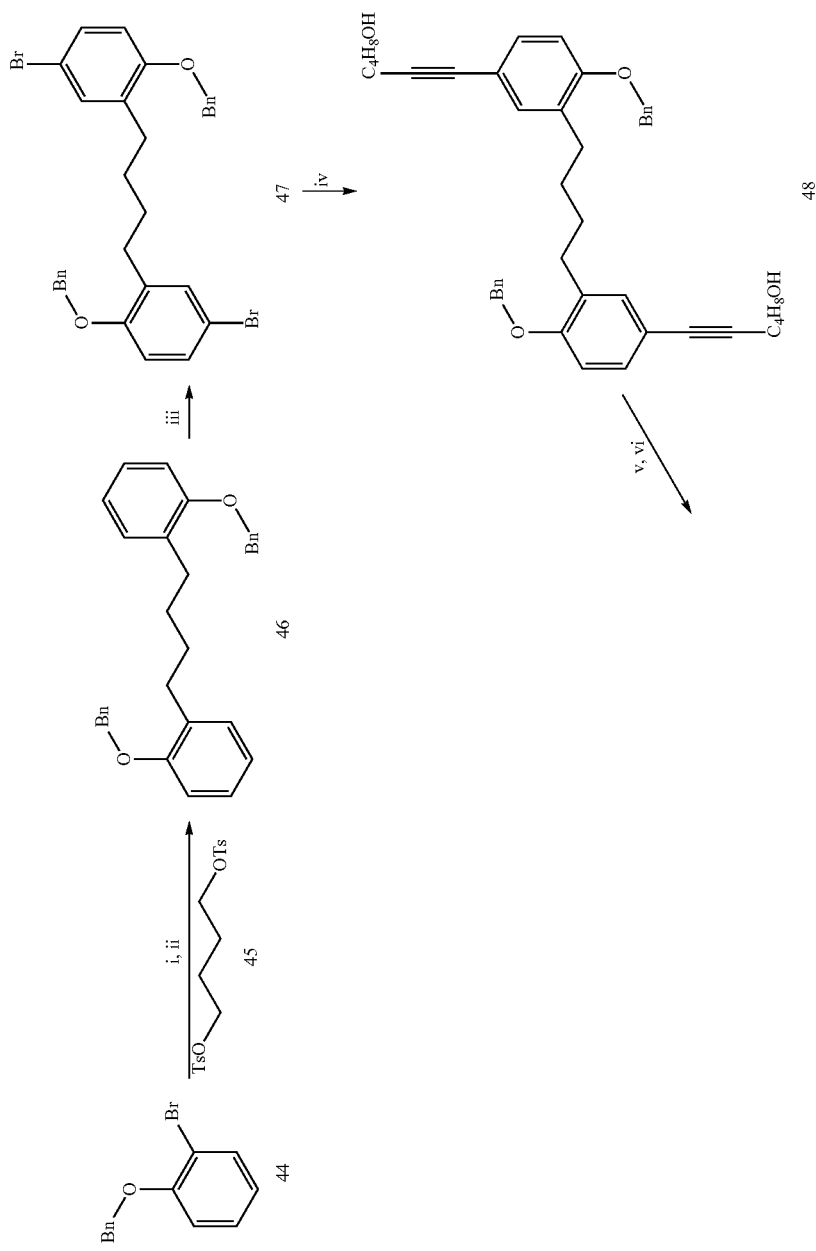

-continued
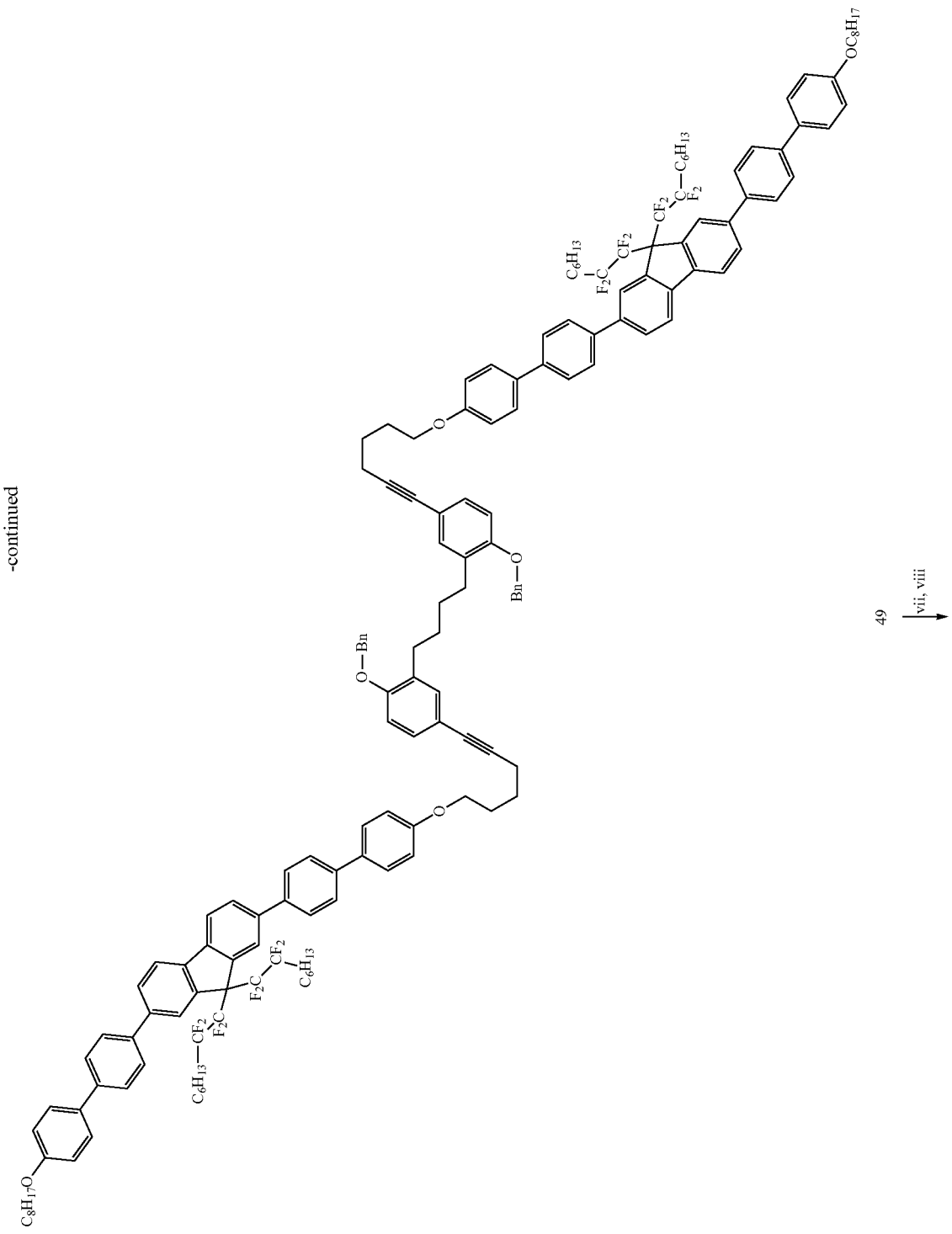
$\xrightarrow{\text{vii, viii}}$ 49

-continued
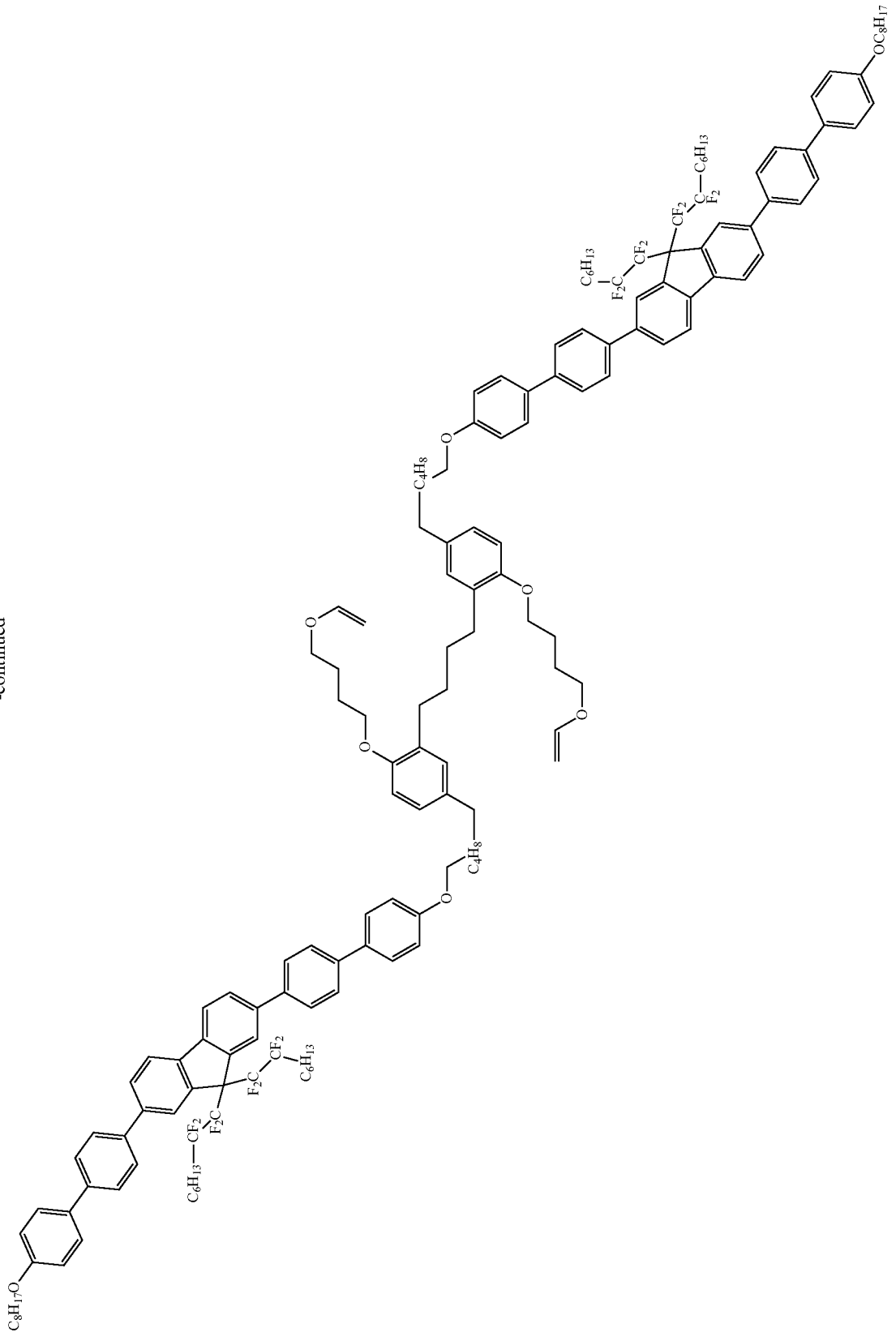
50

Reagents and Conditions:

i) Mg, THF, reflux, 1.5 h; ii) $Li_2[CuCl_4]$, THF, −78° C.-rt, 90 h; iii) $Br_2$, $CH_3CO_2H$, rt, 1 h; iv) 5-hexyn-1-ol, $PdCl_2(PPh_3)_2$, NH(iPr)$_2$, CuI, THF, rt, 16 h; v) TsCl, $C_2H_5N$, 0° C.-rt, 16 h; vi) $Cs_2CO_3$, DMF, 90° C., 18 h; vii) Pd/C, $H_2$, rt, 20 h; viii) 4-bromo-butanol vinyl ether, $K_2CO_3$, butanone, reflux, 16 h.

Scheme 9 Synthesis of cross linkable fluoroalkyl fluorene derivative 58 with Type 3 S³ spacer unit
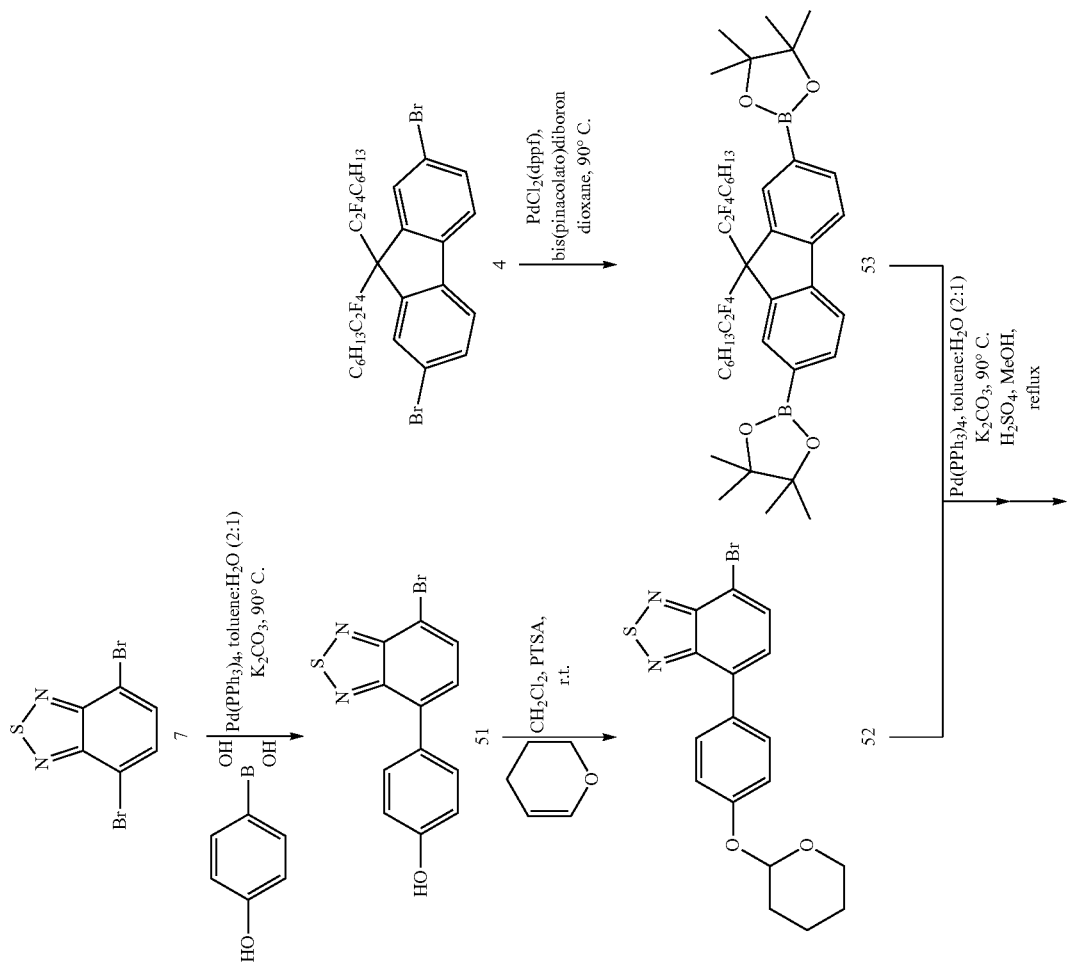

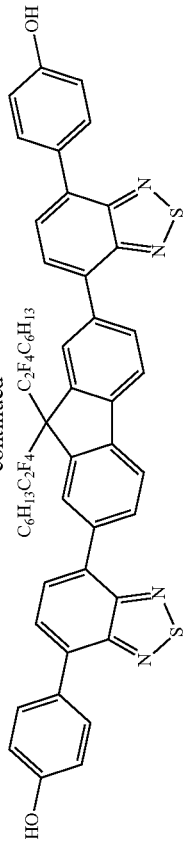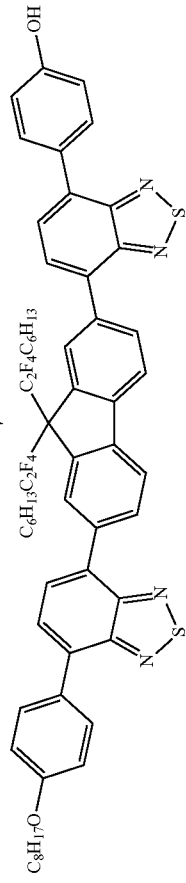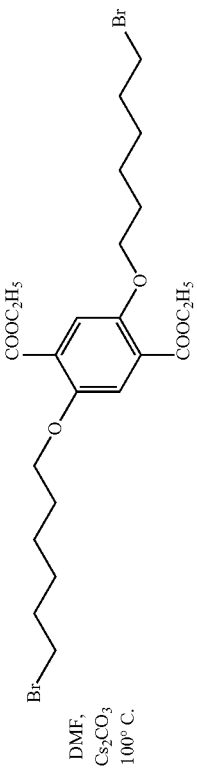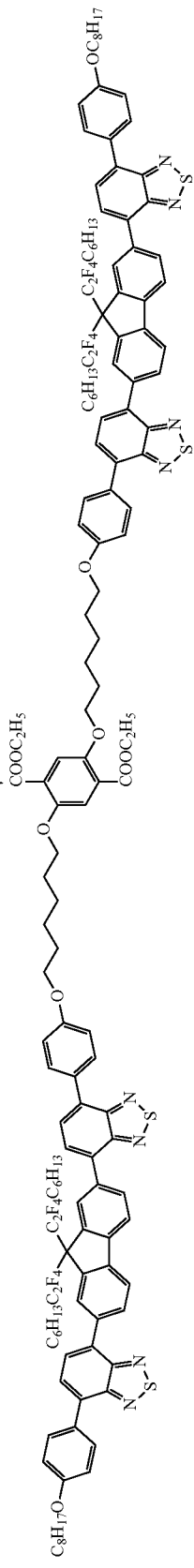

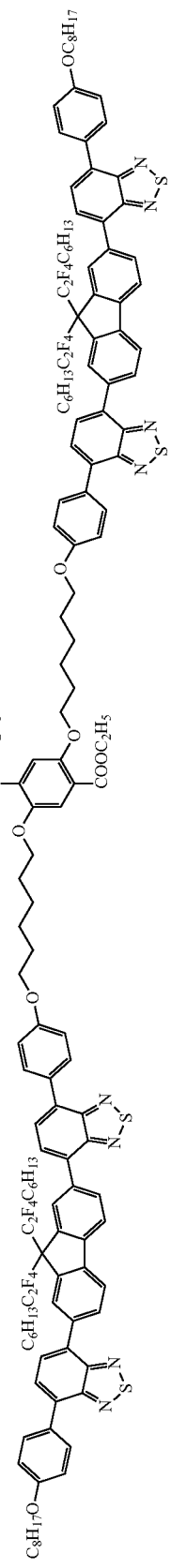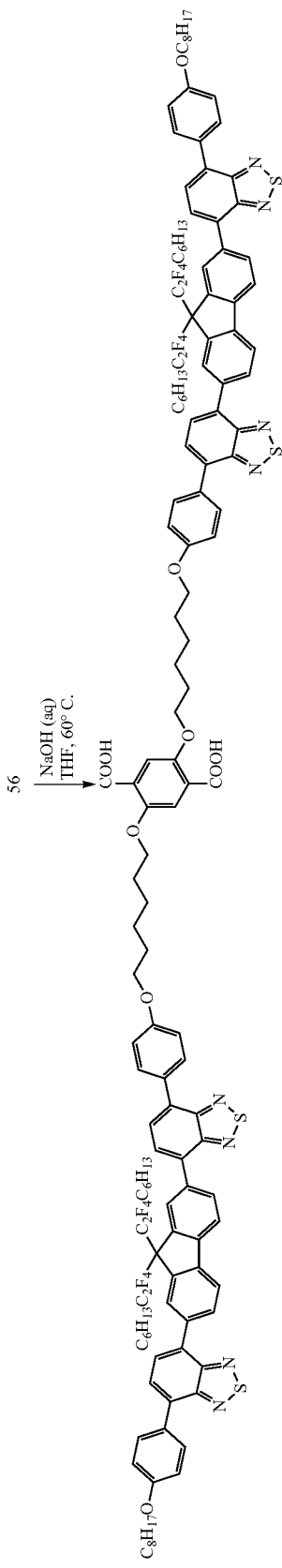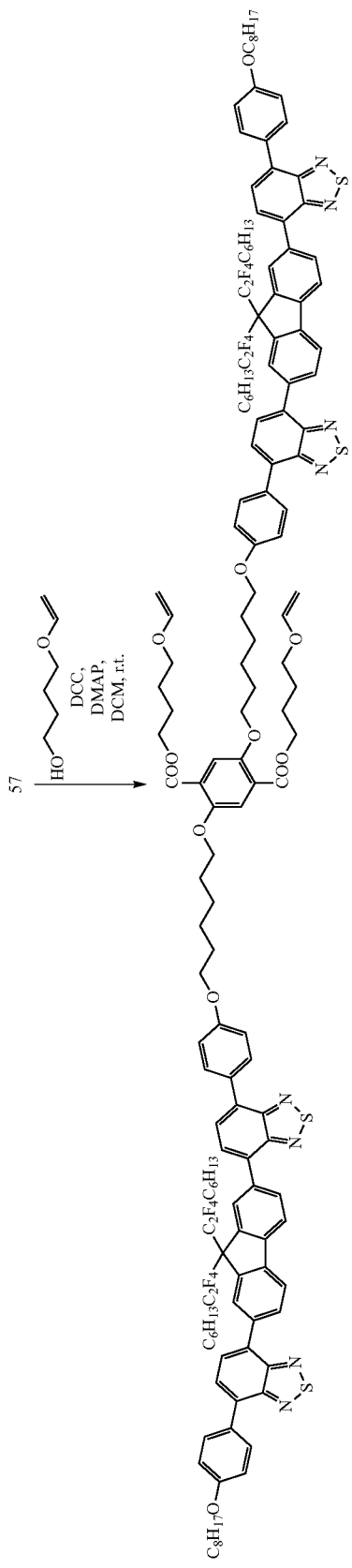

4-(7-bromo-2,1,3-benzothiadiazol-4-yl)-phenol 51

4-Hydroxyphenylboronic acid (3.50 g, 0.0254 mol), 4,7-dibromobenzo[c]-1,2,5-thiadiazole (compound 7, 10.0 g, 0.0340 mol), K$_2$CO$_3$ (10.5 g, 0.0761 mol), dioxane (150 ml) and water (30 ml) were all added to a 3-neck round bottomed flask and three freeze-thaw-pump cycles were carried out. Subsequently, Pd(PPh$_3$)$_4$ (1.47 g, 1.27 mmol) was added and the reaction mixture was stirred at 90° C. for 2 days. The reaction mixture was acidified using 10% v/v dilute hydrochloric acid and extracted into CH$_2$Cl$_2$ (2×200 ml). The combined organic layers were washed with water (2×200 ml), dried (MgSO$_4$), filtered and the crude product was purified by gravity column chromatography (silica gel) using gradient elution (10% ethyl acetate in hexanes to 20% ethyl acetate in hexanes) to yield 51 as a yellow powder (2.70 g, 35%). $^1$H NMR (400 MHz, CDCl$_3$): δ (ppm) 5.19 (br. s, 1H), 6.99 (d, 2H), 7.52 (d, 1H), 7.81 (d, 2H), 7.90 (d, 1H).

4-(7-bromo-2,1,3-benzothiadiazol-4-yl)-THP phenol 52

Compound 51, 3,4-dihydro-2H-pyran, p-toluenesulphonic acid and dry CH$_2$Cl$_2$ was stirred at room temperature overnight (14 h). A few drops of trimethylamine was added and the CH$_2$Cl$_2$ removed using a rotary evaporator. The crude product was purified by flash column chromatography (silica gel) using gradient elution (30% CH$_2$Cl$_2$ in hexanes to 50% CH$_2$Cl$_2$ in hexanes to 100% CH$_2$Cl$_2$) to yield 52 a yellow powder (1.50 g, 39%). $^1$H NMR (400 MHz, CDCl$_3$): δ (ppm) 1.59-1.78 (m, 3H), 1.88-1.93 (m, 2H), 1.99-2.09 (m, 1H), 3.61-3.66 (m, 1H), 3.90-3.96 (m, 1H), 5.52 (t, 1H), 7.21 (d, 2H), 7.52 (d, 1H), 7.84 (d, 2H), 7.89 (d, 1H).

2,7-Bis(4,4,5,5-tetramethyl-1,3,2-dioxaborolan-2-yl)-9,9-di(1,1,2,2-tetrafluorooctyl) fluorene 53

2,7-Dibromo-9,9-di(1,1,2,2 tetrafluorooctane)fluorene (compound 4, 1.50 g, 2.12 mmol), bis(pinacolato)diboron (1.24 g, 4.87 mmol), potassium acetate (1.25 g, 12.7 mmol), PdCl$_2$(dppf) (0.17 g, 0.21 mmol) and dry dioxane (50 ml) were added to a round bottomed flask. Three freeze-thaw-pump cycles were carried out and the reaction mixture heated to 90° C. for 2 days. The reaction mixture was filtered and the dioxane was removed using a rotary evaporator. The crude product was purified by flash column chromatography (silica gel) using 10% ethyl acetate in hexanes as the eluent to yield 53 as a white powder (0.73 g, 43%). $^1$H NMR (400 MHz, CDCl$_3$): δ (ppm) 0.80 (t, 6H), 1.02-1.21 (m, 20H), 1.36 (s, 24H), 7.76 (d, 2H), 7.95 (dd, 2H), 8.19 (s, 2H).

Compound 54

Compound 52 (0.75 g, 1.92 mmol), compound 53 (0.70 g, 0.87 mmol), K$_2$CO$_3$ (0.60 g, 4.36 mmol), toluene (20 ml) and water (10 ml) were all added to a 3-neck round bottomed flask and three freeze-thaw-pump cycles were carried out. Subsequently, Pd(PPh$_3$)$_4$ (0.10 g, 0.09 mmol) was added and the reaction mixture was stirred at 90° C. for 24 h. The reaction mixture was poured into a separating funnel, in which water (10 ml) and more toluene (10 ml) was added. The organic layer was concentrated under reduced pressure with subsequent azeotropic drying using toluene. The crude product was purified by gravity column chromatography (silica gel) using gradient elution (50% CH$_2$Cl$_2$ in hexanes to 100% CH$_2$Cl$_2$) to yield a yellow powder (0.80 g, 91%). After the Suzuki cross-coupling the doubly THP-protected compound was deprotected immediately, without structural characterisation, by refluxing in MeOH (50 ml) and concentrated H$_2$SO$_4$ (5 ml) for 2 h to yield 54 as a yellow powder (0.75 g, 96%). $^1$H NMR (400 MHz, CDCl$_3$): δ (ppm) 0.75 (t, 6H), 1.04-1.27 (m, 20H), 5.25 (br. s, 2H), 7.03 (d, 4H), 7.77 (d, 2H), 7.87 (d, 2H), 7.91 (d, 4H), 7.98 (d, 2H), 8.28 (dd, 2H), 8.40 (s, 2H).

Compound 55

Potassium carbonate (0.20 g, 1.46 mmol) was added to a solution of compound 54 (0.72 g, 0.73 mmol) and 1-bromooctane (0.14 g, 0.73 mmol) in butanone (50 ml) and stirred at reflux overnight (oil bath temperature=80° C., 20 h) under a nitrogen atmosphere. The salts were filtered off, butanone removed under reduced pressure and the crude product was purified by gravity column chromatography (silica gel) using 20% ethyl acetate in hexanes to yield 55 as a yellow powder (0.30 g, 38%). $^1$H NMR (400 MHz, CDCl$_3$): δ (ppm) 0.75 (t, 6H), 0.91 (t, 3H), 1.05-1.69 (m, 30H), 1.85 (quint., 2H), 4.07 (t, 2H), 5.01 (br. s, 1H), 7.03 (d, 2H), 7.09 (d, 2H), 7.77 (d, 1H), 7.79 (d, 1H), 7.87 (d, 2H), 7.90-7.99 (m, 6H), 8.28 (dd, 2H), 8.40 (s, 2H).

Compound 56

Cesium carbonate (0.20 g, 0.62 mmol) was added to a solution of compound 7 (0.25 g, 0.23 mmol) and diethyl 2,5-bis((6-bromohexyl)oxy)terephthalate (0.06 g, 0.10 mmol) in dry DMF (10 ml) and stirred at 100° C. for 24 h under a nitrogen atmosphere. The salts were filtered off, DMF removed under high vacuum (oil pump) and the crude product was purified by gravity column chromatography (silica gel) using 30% ethyl acetate in hexanes to yield 56 as a yellow powder (0.25 g, 93%). $^1$H NMR (400 MHz, CDCl$_3$): δ (ppm) 0.75 (t, 12H), 0.91 (t, 6H), 1.06-1.89 (m, 86H), 4.06 (overlapping triplets, 12H), 4.39 (quint., 4H), 7.09 (d, 8H), 7.37 (s, 2H), 7.78 (d, 4H), 7.87 (d, 4H), 7.93-7.99 (m, 12H), 8.28 (dd, 4H), 8.40 (s, 4H).

Compound 57

An aqueous sodium hydroxide solution (1 g in 10 ml H$_2$O) was added to a solution of compound 56 (0.20 g, 0.08 mmol) in THF (10 ml) and stirred at 60° C. for 48 h. The reaction mixture was acidified using 10% v/v dilute hydrochloric acid (10 ml) and extracted into CH$_2$Cl$_2$ (2×50 ml). The combined organic layers were washed with water (2×50 ml), dried (MgSO$_4$), filtered and the solvent removed using a rotary evaporator to yield 57 as a yellow glassy solid (0.20 g, 100%). $^1$H NMR (400 MHz, CDCl$_3$): δ (ppm) 0.75 (t, 12H), 0.90 (t, 6H), 1.06-2.03 (m, 80H), 4.08 (overlapping triplets, 8H), 4.34 (t, 4H), 7.09 (d, 8H), 7.77 (d, 2H), 7.79 (d, 2H), 7.87 (dd, 4H), 7.90-7.98 (m, 14H), 8.28 (dd, 4H), 8.40 (s, 4H), 11.1 (br. s, 2H).

Compound 58

DCC (0.08 g, 1.16 mmol) was added at one time to a solution of compound 57 (0.20 g, 0.08 mmol), 1,4-butanediol vinylether (0.09 g, 0.80 mmol) and DMAP (4 mg, 0.03 mmol) in dry CH$_2$Cl$_2$ (10 ml) under a nitrogen atmosphere at room temperature. The reaction mixture was stirred for 20 h at room temperature and the CH$_2$Cl$_2$ was removed under reduced pressure. The resulting residue was purified by flash column chromatography (silica gel) by gradient elution (10% ethylacetate in hexanes to 20% ethylacetate in hexanes) to yield 58 as a glassy green solid (0.10 g, 46%). $^1$H NMR (400 MHz, CDCl$_3$): δ (ppm) 0.75 (t, 12H), 0.91 (t, 6H), 1.06-1.89 (m, 88H), 3.75 (t, 4H), 3.99 (dd, 2H), 4.06 (overlapping triplets, 12H), 4.18 (dd, 2H), 4.37 (t, 4H), 6.47 (dd, 2H), 7.09 (d, 8H), 7.38 (s, 2H), 7.78 (d, 4H), 7.86 (d, 4H), 7.93-7.99 (m, 12H), 8.28 (dd, 4H), 8.40 (s, 4H). Mass (MALDI)=2755.6 (M$^+$).

The invention claimed is:

1. A device comprising a polymer comprising 2,7-disubstituted 9,9-fluoroalkyl fluorene repeat units, wherein the device has a plurality of charge transport layers and/or emissive layers that contain 2,7-disubstituted 9,9-fluoroalkyl fluorene diradicals of the formula

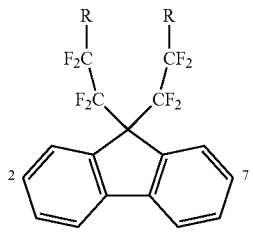

wherein R represents a straight chain or branched achiral C$_1$-C$_{14}$ alkyl, C$_1$-C$_{14}$ haloalkyl or C$_2$-C$_{14}$ alkenyl group, optionally wherein 1, 2, 3, 4 or 5 of the methylene groups of R are replaced by an oxygen atom provided that no acetal, ketal, peroxide or vinyl ether is present, and partially or fully fluorinated derivatives of these groups.

2. The device of claim 1 in the form of an OLED device.

3. The device of claim 1 comprising an interface between a hole transporting layer and an electron transporting layer wherein at least one of said layers contains said 2,7-disubstituted 9,9-fluoroalkyl fluorene diradicals, optionally wherein the device is a photovoltaic device or a thin film transistor (TFT) device.

4. The device according to claim 3 in the form of an OLED device.

5. A device according to claim 1 that contains two or more patterned structures, said structures being comprised of materials that are electroluminescent in nature, wherein the wavelength of electroluminescence emitted by one patterned structure is different from the wavelength of electroluminescence emitted by at least one other patterned structure.

6. A device according to claim 1 that contains a compound of Formula (I)

  D-S$^1$-A-S$^2$—B$^1$,   Formula (I)

wherein:
A represents —Ar$^1$—(FL-Ar$^2$)$_n$— and comprises from 1 to 8 FL groups;
Ar$^1$ and Ar$^2$ in each occurrence are independently selected from the group comprising Ar$^a$ and a bond;
Ar$^a$ represents a diradical comprising 1 aromatic, heteroaromatic or FL moiety, or 2, 3, 4 or 5 aromatic, heteroaromatic and/or FL moieties mutually connected by a single bond;
n is an integer from 1 to 8;
FL is the 2,7-disubstituted 9,9-fluoroalkyl fluorene diradical of the structure

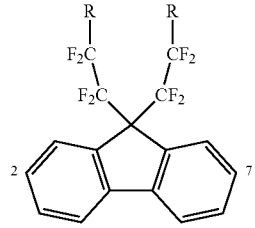

incorporated into the chain through covalent bonds at C-2 and C-7;
the R groups of each FL moiety are identical;
D represents a cross linkable group or, when B represents a hydrogen, D represents —B$^2$—S$^3$—B$^3$—S$^{1a}$-A-S$^{2a}$-B$^{1a}$, —S$^3$(B$^2$)—B$^3$—S$^{1a}$-A-S$^{2a}$-B$^{1a}$, 3(B$^2$)(B$^3$)—S$^{1a}$-A-S$^{2a}$-B$^{1a}$, —S$^3$(B$^2$)(B$^3$), or a cross linkable group wherein the dash at the left-hand end of the chain represents the point of attachment to S$^1$;
B$^1$ represents a cross linkable group or a hydrogen atom;
B$^{1a}$ represents a cross linkable group or a hydrogen atom;
B$^2$ and B$^3$ each represents a cross linkable group;
S$^1$, S$^2$, S$^{1a}$ and S$^{2a}$ are flexible linker groups; and
S$^3$ is a spacer group.

7. A device according to claim 6 wherein Ar$^a$ represents a diradical comprising a C$_6$-C$_{16}$ aromatic, C$_4$-C$_{12}$ heteroaromatic or FL moiety, or 2 or 3 C$_6$-C$_{16}$ aromatic, C$_4$-C$_{12}$ heteroaromatic and/or FL moieties mutually connected by a single bond.

8. A device according to claim 6, wherein S$^1$, S$^{1a}$, S$^2$ and S$^{2a}$ in each occurrence are independently selected from straight chain or branched achiral C$_5$-C$_{14}$ alkyl groups, optionally wherein 1, 2, 3, 4 or 5 methylene groups are substituted for an oxygen atom provided that no acetal, ketal or peroxide is present, that is connected to A through either a bond or an ether, ester, carbonate, thioether, amine or amide linkage and that is connected through either a bond or an ether, ester, carbonate, thioether, amine or amide linkage to D, B$^1$, B$^2$, B$^3$ or S$^3$ as determined by the nature of D.

9. A device according to claim 6 wherein S$^3$ represents a C$_1$-C$_{20}$ alkyl group, C$_1$-C$_{20}$ haloalkyl group, a C$_3$-C$_8$ cycloalkyl group, a C$_6$-C$_{16}$ aryl group or a C$_4$-C$_{15}$ heteroaryl group or a chain consisting of 1, 2, 3, 4 or 5 C$_1$-C$_{20}$ alkyl, C$_1$-C$_{20}$ haloalkyl, C$_3$-C$_8$ cycloalkyl, C$_6$-C$_{16}$ aryl and/or C$_4$-C$_{15}$ heteroaryl moieties each independently connected by a bond, an ether linkage or an ester linkage.

10. A device according to claim 6 wherein B$^1$, B$^2$, B$^3$ and D when it represents a crosslinking group in each occurrence independently represents a radiation activated cross linking group, optionally wherein said radiation is ultraviolet light.

11. A device according to claim 6 wherein the compound of Formula (I) is in liquid crystalline form or in solidified glass form.

12. A device according to claim 6 wherein the compound of Formula (I) is in the form of a network polymer formed by exposure of the compound to radiation.

13. A device according to claim 6 wherein R is an alkenyl group.

14. A device according to claim 13 wherein the alkenyl group includes only one carbon-carbon double bond.

15. A device according to claim 14 wherein the carbon-carbon double bond is terminal.

16. A device according to claim 6 wherein the R groups are as shown below:

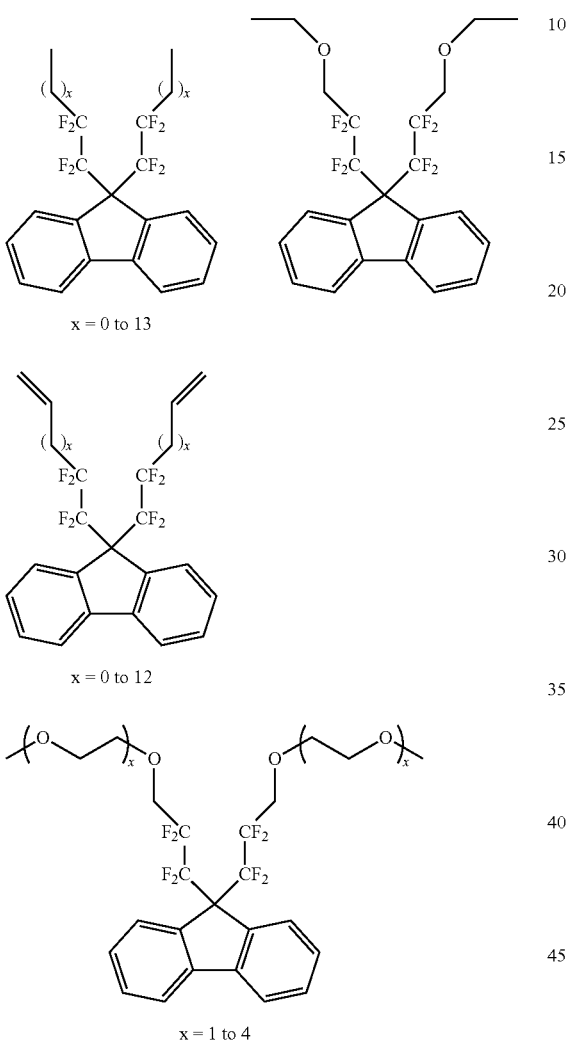

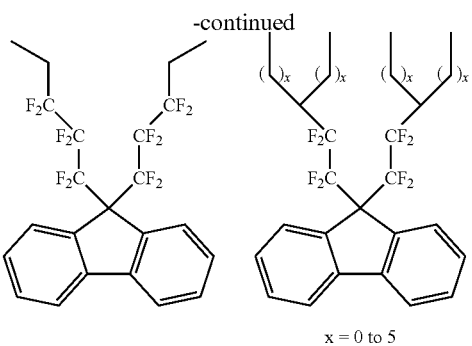

x = 0 to 5

17. The device of claim 6 comprising an interface between a hole transporting layer and an electron transporting layer wherein at least one of said layers contains said 2,7-disubstituted 9,9-fluoroalkyl fluorene diradicals, optionally wherein the device is a photovoltaic device or a thin film transistor (TFT) device.

18. The device of claim 17 that contains two or more patterned structures, said structures being comprised of materials that are electroluminescent in nature, wherein the wavelength of electroluminescence emitted by one patterned structure is different from the wavelength of electroluminescence emitted by at least one other patterned structure.

19. The device of claim 18 in the form of an OLED device.

20. A device comprising:
   a polymer comprising 2,7-disubstituted 9,9-fluoroalkyl fluorene repeat units wherein R represents a straight chain or branched achiral $C_1$-$C_{14}$ alkyl, $C_1$-$C_{14}$ haloalkyl or $C_2$-$C_{14}$ alkenyl group, optionally wherein 1, 2, 3, 4 or 5 of the methylene groups of R are replaced by an oxygen atom provided that no acetal, ketal, peroxide or vinyl ether is present, and partially or fully fluorinated derivatives of these groups;
   an interface between a hole transporting layer and an electron transporting layer wherein at least one of said layers contains said 2,7-disubstituted 9,9-fluoroalkyl fluorene diradicals, optionally wherein the device is a photovoltaic device or a thin film transistor (TFT) device; and
   two or more patterned structures, said structures being comprised of materials that are electroluminescent in nature, wherein the wavelength of electroluminescence emitted by one patterned structure is different from the wavelength of electroluminescence emitted by at least one other patterned structure.

\* \* \* \* \*